United States Patent
Hayoz

(10) Patent No.: US 9,293,718 B2
(45) Date of Patent: Mar. 22, 2016

(54) DIKETOPYRROLOPYRROLE POLYMERS AND SMALL MOLECULES

(71) Applicant: BASF SE, Ludwigshafen (DE)

(72) Inventor: Pascal Hayoz, Hofstetten (CH)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 14/386,123

(22) PCT Filed: Apr. 2, 2013

(86) PCT No.: PCT/EP2013/056903
§ 371 (c)(1),
(2) Date: Sep. 18, 2014

(87) PCT Pub. No.: WO2013/150005
PCT Pub. Date: Oct. 10, 2013

(65) Prior Publication Data
US 2015/0132886 A1    May 14, 2015

Related U.S. Application Data

(60) Provisional application No. 61/619,943, filed on Apr. 4, 2012, provisional application No. 61/623,080, filed on Apr. 12, 2012.

(30) Foreign Application Priority Data

Apr. 4, 2012   (EP) .................................... 12163088
Apr. 12, 2012  (EP) .................................... 12163887

(51) Int. Cl.
| | |
|---|---|
| C08G 75/00 | (2006.01) |
| H01L 51/00 | (2006.01) |
| C09K 11/06 | (2006.01) |
| C08G 73/06 | (2006.01) |
| C08G 61/12 | (2006.01) |
| C07D 487/04 | (2006.01) |
| C09B 57/00 | (2006.01) |
| C09B 67/22 | (2006.01) |
| C09B 69/00 | (2006.01) |
| C09B 69/10 | (2006.01) |

(Continued)

(52) U.S. Cl.
CPC .......... *H01L 51/0094* (2013.01); *C07D 487/04* (2013.01); *C07F 7/083* (2013.01); *C07F 7/0812* (2013.01); *C07F 7/0856* (2013.01); *C07F 7/0881* (2013.01); *C08G 61/12* (2013.01); *C08G 61/124* (2013.01); *C08G 61/126* (2013.01); *C08G 73/0672* (2013.01); *C09B 57/004* (2013.01); *C09B 67/0033* (2013.01); *C09B 69/008* (2013.01); *C09B 69/109* (2013.01);

(Continued)

(58) Field of Classification Search
CPC .................................................... C09B 57/004
USPC ........... 257/40, E51.012; 427/331; 528/367.8
See application file for complete search history.

(56) References Cited

U.S. PATENT DOCUMENTS

| | | |
|---|---|---|
| 6,451,459 B1 | 9/2002 | Tieke et al. |
| 6,690,029 B1 | 2/2004 | Anthony et al. |

(Continued)

FOREIGN PATENT DOCUMENTS

| | | |
|---|---|---|
| EP | 2 034 537 A2 | 3/2009 |
| WO | WO 03/052841 A1 | 6/2003 |

(Continued)

OTHER PUBLICATIONS

U.S. Appl. No. 14/385,696, filed Sep. 16, 2014, Welker, et al.

(Continued)

*Primary Examiner* — Shane Fang
(74) *Attorney, Agent, or Firm* — Oblon, McClelland, Maier & Neustadt, L.L.P.

(57) ABSTRACT

The present invention relates to polymers, comprising a repeating unit of the formula (I), and compounds of formula (II), wherein Y, $Y^{15}$, $Y^{16}$ and $Y^{17}$ are independently of each other a group of formula (a) characterized in that the polymers and compounds comprise silicon-containing solubilizing side chains and their use as organic semiconductor in organic devices, especially in organic photovoltaics and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics and photodiodes.

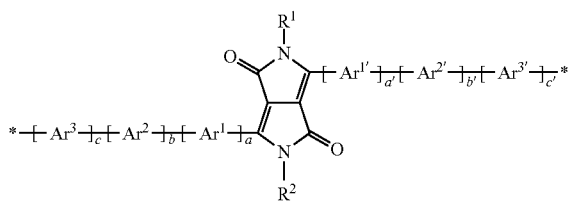

(I)

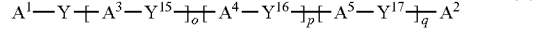

(II)

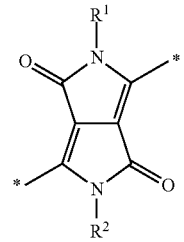

(a)

23 Claims, No Drawings

(51) Int. Cl.
  *H05B 33/10* (2006.01)
  *C07F 7/08* (2006.01)
  *H01L 51/05* (2006.01)
  *H01L 51/42* (2006.01)
  *H01L 51/50* (2006.01)

(52) U.S. Cl.
  CPC .............. *C09K 11/06* (2013.01); *H01L 51/00* (2013.01); *H01L 51/0003* (2013.01); *H01L 51/0035* (2013.01); *H01L 51/0036* (2013.01); *H01L 51/0043* (2013.01); *H01L 51/05* (2013.01); *H01L 51/42* (2013.01); *H05B 33/10* (2013.01); *C08G 2261/124* (2013.01); *C08G 2261/144* (2013.01); *C08G 2261/1412* (2013.01); *C08G 2261/3222* (2013.01); *C08G 2261/3223* (2013.01); *C08G 2261/3243* (2013.01); *C08G 2261/3327* (2013.01); *C08G 2261/344* (2013.01); *C08G 2261/364* (2013.01); *C08G 2261/411* (2013.01); *C08G 2261/91* (2013.01); *C08G 2261/92* (2013.01); *C08G 2261/95* (2013.01); *C09K 2211/1007* (2013.01); *C09K 2211/1011* (2013.01); *C09K 2211/1029* (2013.01); *C09K 2211/1092* (2013.01); *C09K 2211/1416* (2013.01); *C09K 2211/1425* (2013.01); *C09K 2211/1458* (2013.01); *C09K 2211/1466* (2013.01); *C09K 2211/1491* (2013.01); *H01L 51/0055* (2013.01); *H01L 51/0074* (2013.01); *H01L 51/0558* (2013.01); *H01L 51/4253* (2013.01); *H01L 51/5012* (2013.01); *Y02E 10/549* (2013.01)

(56) References Cited

U.S. PATENT DOCUMENTS

| | | | |
|---|---|---|---|
| 7,939,818 | B2 | 5/2011 | Heim et al. |
| 8,404,864 | B2 | 3/2013 | Hao et al. |
| 8,629,238 | B2 | 1/2014 | Dueggeli et al. |
| 8,796,469 | B2 | 8/2014 | Hayoz et al. |
| 8,835,579 | B2 | 9/2014 | Lamatsch et al. |
| 2003/0021913 | A1 | 1/2003 | O'Neill et al. |
| 2006/0013549 | A1 | 1/2006 | Shtein et al. |
| 2007/0079867 | A1 | 4/2007 | Chittibabu et al. |
| 2009/0065878 | A1 | 3/2009 | Li |
| 2009/0302311 | A1 | 12/2009 | Turbiez et al. |
| 2011/0215313 | A1 | 9/2011 | Düggeli et al. |
| 2011/0240981 | A1 | 10/2011 | Düggeli et al. |
| 2011/0284826 | A1 | 11/2011 | Hayoz et al. |
| 2012/0074393 | A1 | 3/2012 | Würthner et al. |
| 2012/0095236 | A1 | 4/2012 | Hayoz et al. |
| 2012/0142872 | A1 | 6/2012 | Lamatsch et al. |
| 2014/0128618 | A1 | 5/2014 | Hayoz et al. |
| 2014/0217329 | A1 | 8/2014 | Hayoz et al. |
| 2014/0299871 | A1 | 10/2014 | Bujard et al. |
| 2014/0332730 | A1 | 11/2014 | Hayoz et al. |

FOREIGN PATENT DOCUMENTS

| | | |
|---|---|---|
| WO | WO 2004/101581 A2 | 11/2004 |
| WO | WO 2004/112161 A2 | 12/2004 |
| WO | WO 2005/049695 A1 | 6/2005 |
| WO | WO 2007/082584 A1 | 7/2007 |
| WO | WO 2008/000664 A1 | 1/2008 |
| WO | WO 2008/001123 A1 | 1/2008 |
| WO | WO 2008/107089 A1 | 9/2008 |
| WO | WO 2009/047104 A2 | 4/2009 |
| WO | WO 2010/049321 A1 | 5/2010 |
| WO | WO 2010/049323 A1 | 5/2010 |
| WO | WO 2010/108873 A1 | 9/2010 |
| WO | WO 2010/115767 A1 | 10/2010 |
| WO | WO 2010/136352 A1 | 12/2010 |
| WO | WO 2010/136353 A1 | 12/2010 |
| WO | WO 2011/144566 A2 | 11/2011 |
| WO | WO 2012/041849 A1 | 4/2012 |
| WO | WO 2012/175530 A1 | 12/2012 |
| WO | WO 2013/030325 A1 | 3/2013 |
| WO | WO 2013/083506 A1 | 6/2013 |
| WO | WO 2013/083507 A1 | 6/2013 |

OTHER PUBLICATIONS

International Search Report issued Sep. 12, 2013 in PCT/EP2013/056903.

DIKETOPYRROLOPYRROLE POLYMERS AND SMALL MOLECULES

The present invention relates to polymers, comprising a repeating unit of the formula (I), and compounds of formula (II), wherein Y, $Y^{15}$, $Y^{16}$ and $Y^{17}$ are independently of each other a group of formula

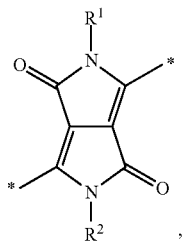

characterized in that the polymers and compounds comprise silicon-containing solubilizing side chains and their use as organic semiconductor in organic devices, especially in organic photovoltaics (solar cells) and photodiodes, or in a device containing a diode and/or an organic field effect transistor. The polymers and compounds according to the invention can have excellent solubility in organic solvents and excellent film-forming properties. In addition, high efficiency of energy conversion, excellent field-effect mobility, good on/off current ratios and/or excellent stability can be observed, when the polymers and compounds according to the invention are used in organic field effect transistors, organic photovoltaics and photodiodes.

It is one object of the present invention to provide polymers and small molecules, which show high efficiency of energy conversion, excellent field-effect mobility, good on/off current ratios and/or excellent stability, when used in organic field effect transistors, organic photovoltaics (solar cells) and photodiodes.

Said object has been solved by polymers, comprising a repeating unit of the formula

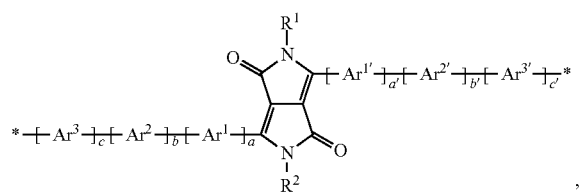

(I)

wherein a is 0, 1, 2, or 3; a' is 0, 1, 2, or 3; b is 0, 1, 2, or 3; b' is 0, 1, 2, or 3; c is 0, 1, 2, or 3; c' is 0, 1, 2, or 3;

$R^1$ and $R^2$ may be the same or different and are selected from a $C_1$-$C_{100}$alkyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —$NR^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$, a $C_2$-$C_{100}$alkenyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —$NR^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$, a $C_3$-$C_{100}$alkinyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —$NR^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$, a $C_3$-$C_{12}$cycoalkyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —$NR^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$, a $C_6$-$C_{24}$aryl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$;

a $C_2$-$C_{20}$heteroaryl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$;

—CO—$C_1$-$C_{18}$alkyl, —CO—$C_5$-$C_{12}$cycloalkyl, —COO—$C_1$-$C_{18}$alkyl which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —$NR^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$ $E^{Si}$ is —$SiR^{161}R^{162}R^{163}$ or —O—$SiR^{161}R^{162}R^{163}$;

$D^{Si}$ is —$SiR^{161}R^{162}$—, —$SiR^{161}R^{162}$—(O—$SiR^{161}R^{162}$)$_d$— or —O—$SiR^{161}R^{162}$—;

$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{164}R^{165}R^{166}$, —(O—$SiR^{164}R^{165}$)$_d$—$R^{166}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$alkyl, halogen, cyano or $C_1$-$C_{25}$alkoxy;

$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$SiR^{169}R^{170}R^{171}$, —(O—$SiR^{169}R^{170}$)$_d$—$R^{171}$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;

$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl; $C_1$-$C_{25}$haloalkyl, $C_2$-$C_{25}$alkenyl, —O—$Si(CH_3)_3$, $C_1$-$C_{25}$alkoxy, $C_3$-$C_{24}$(hetero)aryloxy, $NR^{167}R^{168}$, halogen, $C_1$-$C_{25}$acyloxy, phenyl, phenyl, which is substituted 1 to 3 times by $C_1$-$C_{24}$alkyl, halogen, cyano or $C_1$-$C_{25}$alkoxy;

$R^{167}$ and $R^{168}$ are independently of each other hydrogen, $C_6$-$C_{18}$ aryl; $C_6$-$C_{18}$ aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

d is an integer from 1 to 50;

$R^{39}$ is hydrogen, $C_1$-$C_{18}$alkyl, $C_1$-$C_{18}$haloalkyl, $C_7$-$C_{25}$arylalkyl, or $C_1$-$C_{18}$alkanoyl, $Ar^1$, $Ar^{1'}$, $Ar^2$, $Ar^{2'}$, $Ar^3$ and $Ar^{3'}$ are independently of each other

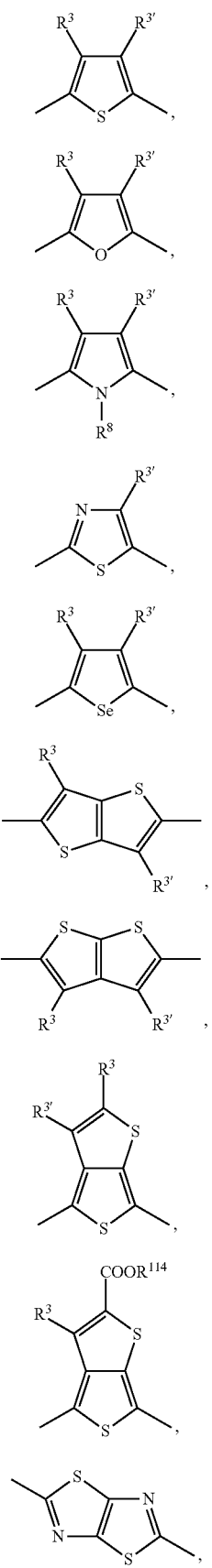

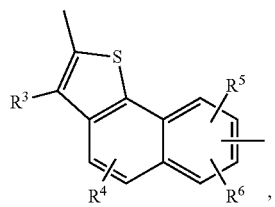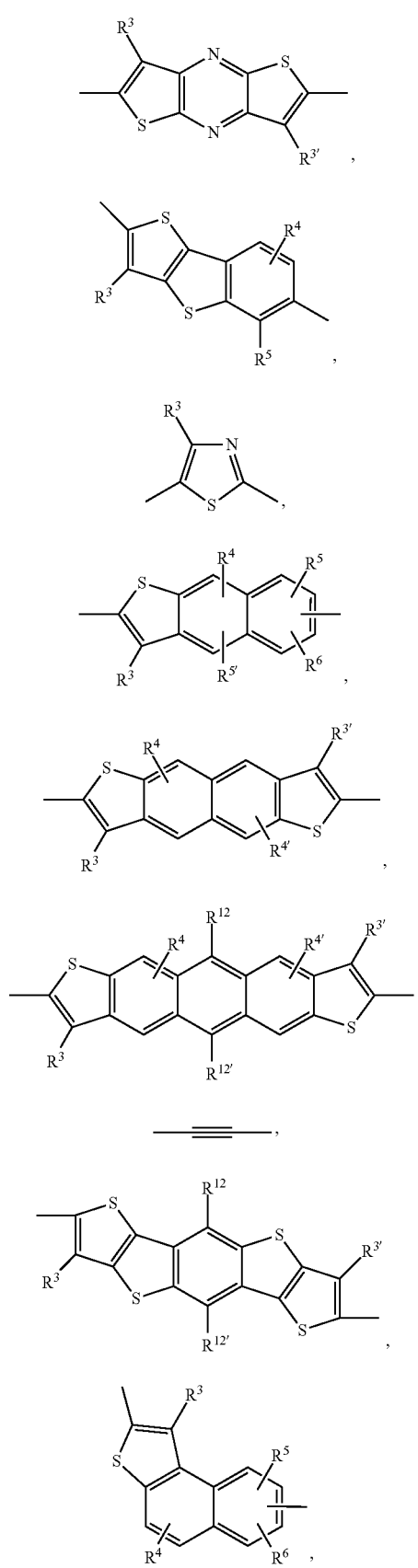

-continued
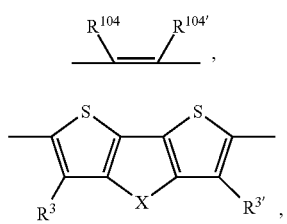
(XIII)
such as, for example
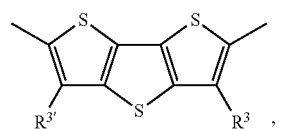
(XIIIa)
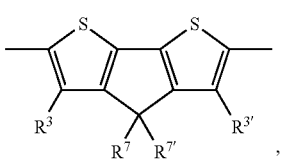
(XIIIb)
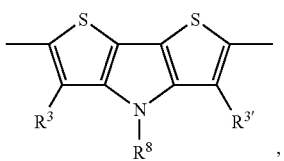
(XIIIc)
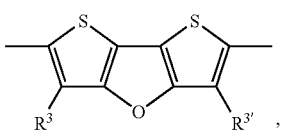
(XIIId)
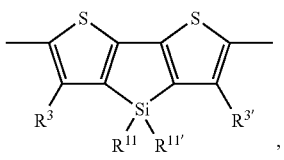
(XIIIe)
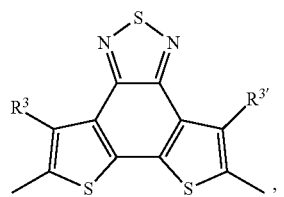
(XIIIf)
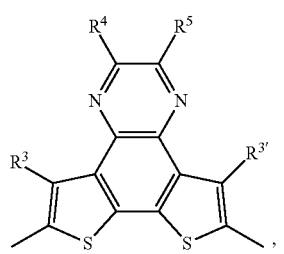
(XIIIg)
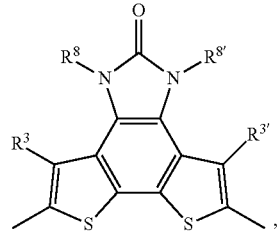
(XIIIh)
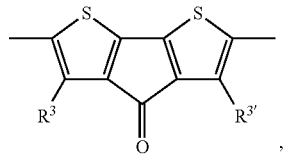
(XIIIi)
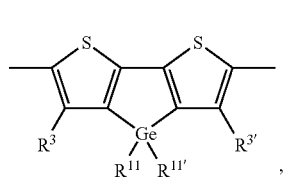
(XIIIj)
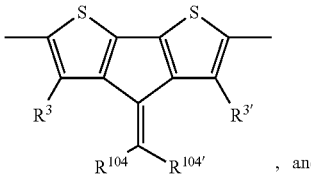
(XIIIk)
, and
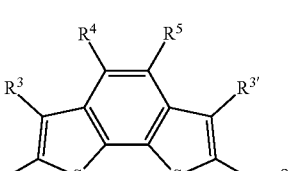
(XIIIl)
, or
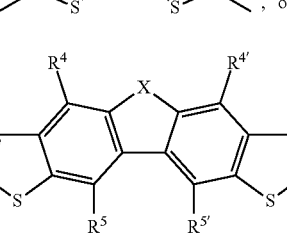
(XIV)
such as, for example,
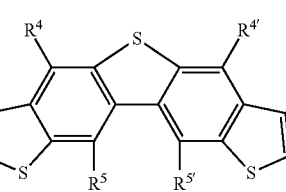
(XIVa)
wherein
X is —O—, —S—, —NR$^8$—, —Si(R$^{11}$)(R$^{11'}$)—, —Ge(R$^{11}$)(R$^{11'}$)—, —C(R$^7$)(R$^{7'}$)—, —C(=O)—, —C(=CR$^{104}$R$^{104'}$)—;

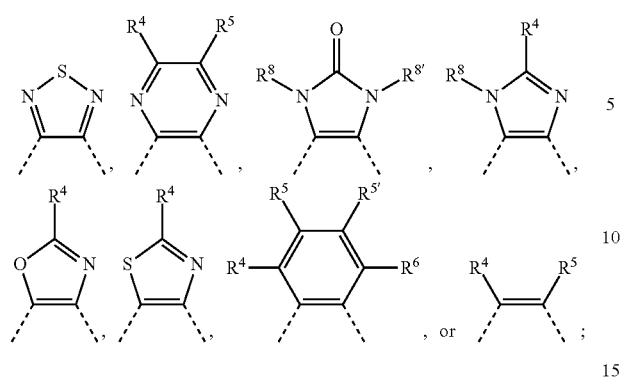

$R^3$ and $R^{3'}$ are independently of each other hydrogen, halogen, $E^{Si}$, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, $C_1$-$C_{25}$alkyl substituted with one or more $E^{Si}$, or $C_1$-$C_{25}$alkoxy;

$R^4$, $R^{4'}$, $R^5$, $R^{5'}$, $R^6$, and $R^{6'}$ are independently of each other hydrogen, halogen, $E^{Si}$, halogenated $C_1$-$C_2$alkyl, cyano, $C_1$-$C_2$alkyl, which may optionally be interrupted by one or more oxygen or sulphur atoms; $C_7$-$C_{25}$arylalkyl, $C_1$-$C_{25}$alkyl substituted with one or more $E^{Si}$, or $C_1$-$C_{25}$alkoxy;

$R^7$, $R^{7'}$, $R^9$ and $R^{9'}$ are independently of each other hydrogen, $C_1$-$C_{25}$alkyl, which may optionally be interrupted by one, or more oxygen, or sulphur atoms; $C_1$-$C_{25}$alkyl substituted with one or more $E^{Si}$, or $C_7$-$C_{25}$arylalkyl, or $R^7$ and $R^{7'}$, or $R^9$ and $R^{9'}$ are together $=CR^{104}R^{104'}$;

$R^8$ and $R^{8'}$ are independently of each other hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; $C_1$-$C_{25}$alkyl substituted with one or more $E^{Si}$, or $C_7$-$C_{25}$arylalkyl, $R^{11}$ and $R^{11'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{12}$ and $R^{12'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$ arylalkyl, or $=\!\!=\!\!=\!\!R^{13}$, wherein $R^{13}$ is a $C_1$-$C_{10}$alkyl group, or a tri($C_1$-$C_8$alkyl)silyl group; or $Ar^1$, $Ar^{1'}$ $Ar^2$, $Ar^{2'}$, $Ar^3$ and $Ar^{3'}$ are independently of each other

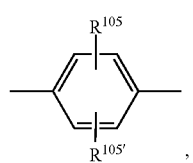

(XVa)

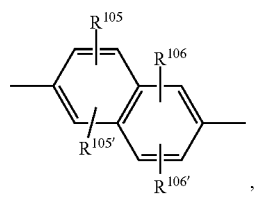

(XVb)

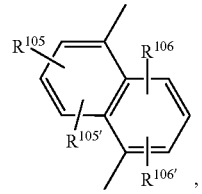

(XVc)

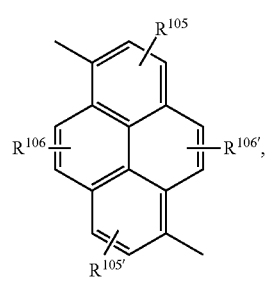

(XVd)

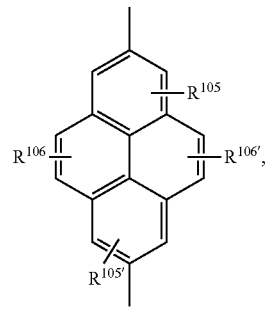

(XVe)

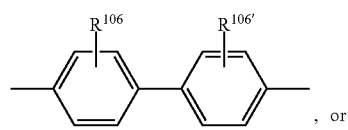

(XVf)

, or

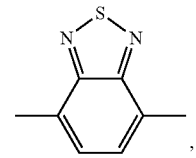

(XVg)

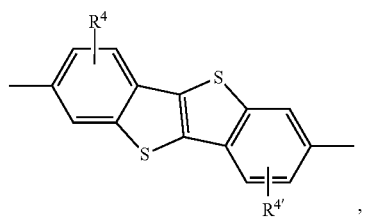

(XVh)

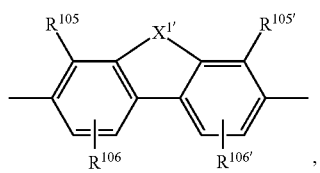

(XVI)

such as, for example

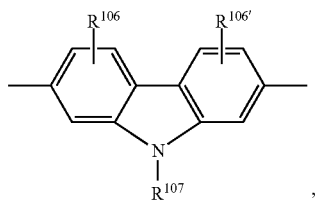

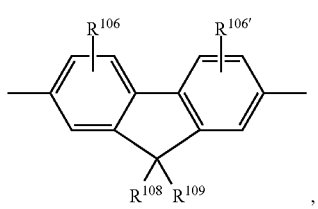

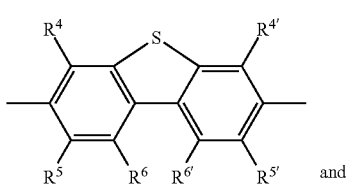

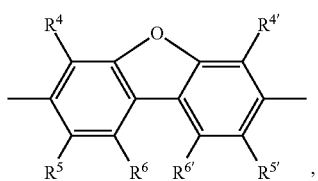

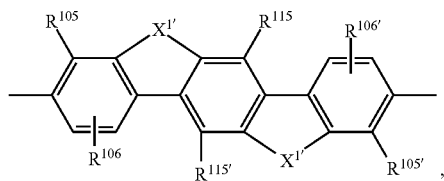

such as, for example,

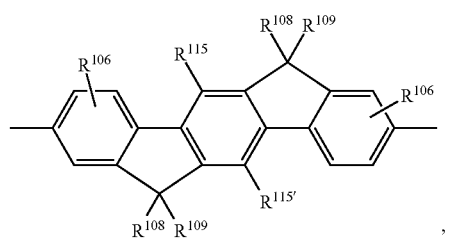

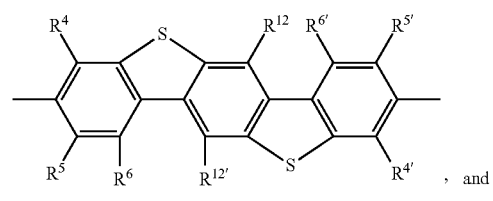

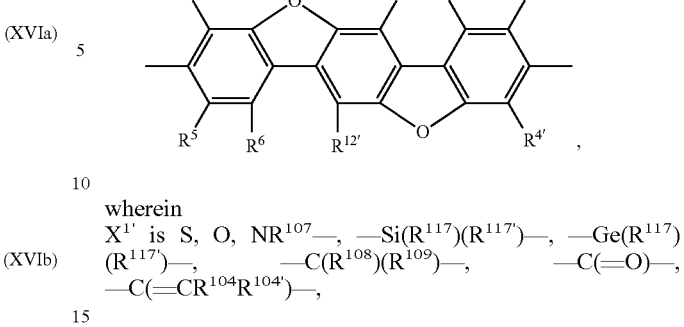

wherein
X$^{1'}$ is S, O, NR$^{107}$—, —Si(R$^{117}$)(R$^{117'}$)—, —Ge(R$^{117}$)(R$^{117'}$)—, —C(R$^{108}$)(R$^{109}$)—, —C(=O)—, —C(=CR$^{104}$R$^{104'}$)—,

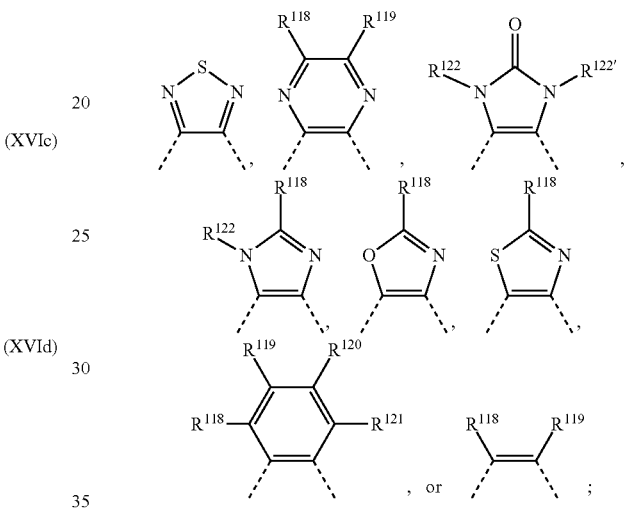

R$^{104}$ and R$^{104'}$ are independently of each other hydrogen, cyano, COOR$^{103}$, a C$_1$-C$_{25}$alkyl group, or C$_6$-C$_{24}$aryl or C$_2$-C$_{20}$heteroaryl;

R$^{103}$ is C$_1$-C$_{25}$alkyl, C$_1$-C$_{25}$alkyl, which may optionally be interrupted by one or more oxygen or sulphur atoms; or C$_7$-C$_{25}$arylalkyl;

R$^{105}$, R$^{105'}$, R$^{106}$ and R$^{106'}$ are independently of each other hydrogen, halogen, cyano, C$_1$-C$_{25}$alkyl, which may optionally be interrupted by one or more oxygen or sulphur atoms; C$_7$-C$_{25}$arylalkyl, or C$_1$-C$_{18}$alkoxy, R$^{107}$ is hydrogen, C$_7$-C$_{25}$arylalkyl, C$_6$-C$_{18}$aryl; C$_6$-C$_{18}$aryl which is substituted by C$_1$-C$_{18}$alkyl, or C$_1$-C$_{18}$alkoxy; C$_1$-C$_{18}$perfluoroalkyl; C$_1$-C$_{25}$alkyl; which may be interrupted by —O—, or —S—; or —COOR$^{103}$; R$^{103}$ is as defined above;

R$^{108}$ and R$^{109}$ are independently of each other H, C$_1$-C$_{25}$alkyl, C$_1$-C$_{25}$alkyl which is substituted by E and/or interrupted by D, C$_7$-C$_{25}$arylalkyl, C$_6$-C$_{24}$aryl, C$_6$-C$_{24}$aryl which is substituted by G, C$_2$-C$_{20}$heteroaryl, C$_2$-C$_{20}$heteroaryl which is substituted by G, C$_2$-C$_{18}$alkenyl, C$_2$-C$_{18}$alkynyl, C$_1$-C$_{18}$alkoxy, C$_1$-C$_{18}$alkoxy which is substituted by E and/or interrupted by D, or C$_7$-C$_{25}$aralkyl, or R$^{108}$ and R$^{109}$ together form a group of formula =CR$^{110}$R$^{111}$, wherein R$^{110}$ and R$^{111}$ are independently of each other H, C$_1$-C$_{18}$alkyl, C$_1$-C$_{18}$alkyl which is substituted by E and/or interrupted by D, C$_6$-C$_{24}$aryl, C$_6$-C$_{24}$aryl which is substituted by G, or C$_2$-C$_{20}$heteroaryl, or C$_2$-C$_{20}$heteroaryl which is substituted by G, or R$^{108}$ and R$^{109}$ together form a five or six membered ring, which optionally can be substituted by C$_1$-C$_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —$NR^{112}$, E is $C_1$-$C_8$thioalkoxy, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H; $C_6$-$C_{18}$aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—, $R^{114}$ is $C_1$-$C_{25}$alkyl, which may optionally be interrupted by one, or more oxygen, or sulphur atoms, $R^{115}$ and $R^{115'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or ═$R^{116}$, wherein $R^{116}$ is a $C_1$-$C_{10}$alkyl group, or a tri($C_1$-$C_8$alkyl)silyl group;

$R^{117}$ and $R^{117'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, cyano, $C_1$-$C_{25}$alkyl, which may optionally be interrupted by one or more oxygen or sulphur atoms; $C_7$-$C_{25}$arylalkyl, or $C_1$-$C_{25}$alkoxy;

$R^{122}$ and $R^{122'}$ are independently of each other hydrogen, $C_6$-$C_{18}$ aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_7$-$C_{25}$arylalkyl;

with the proviso that at least one of the groups $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^{8'}$, $R^9$ and $R^{9'}$ contains a group $E^{Si}$ and/or $D^{Si}$.

a and a' are preferably different from 0.

Advantageously, the polymer of the present invention, or an organic semiconductor material, layer or component, comprising the polymer of the present invention, can be used in organic photovoltaics (solar cells) and photodiodes, or in an organic field effect transistor (OFET).

The polymers of this invention preferably have a weight average molecular weight of 4,000 Daltons or greater, especially 4,000 to 2,000,000 Daltons, more preferably 10,000 to 1,000,000 and most preferably 10,000 to 100,000 Daltons. Molecular weights are determined according to high-temperature gel permeation chromatography (HT-GPC) using polystyrene standards. The polymers of this invention preferably have a polydispersity of 1.01 to 10, more preferably 1.1 to 3.0, most preferred 1.5 to 2.5. The polymers of the present invention are preferably conjugated.

The oligomers (small molecules) of the present invention preferably have a weight average molecular weight below 4,000 Daltons.

In an embodiment of the present invention the polymer is a polymer of formula $$\left[ \begin{array}{c} \phantom{x} \\ *\!\!-\!\!(Ar^3)_{c}\!\!-\!\!(Ar^2)_{b}\!\!-\!\!(Ar^1)_{a}\!\!-\!\!\underset{\underset{R^2}{|}}{\overset{\overset{R^1}{|}}{N}}\!\!-\!\!(Ar^1)_{a'}\!\!-\!\!(Ar^{2'})_{b'}\!\!-\!\!(Ar^{3'})_{c'}\!\!-\!\!* \end{array} \right]_n$$

wherein n is usually in the range of 4 to 1000, especially 4 to 200, very especially 5 to 150.

$R^1$ and $R^2$ may be the same or different and are preferably selected from a $C_1$-$C_{100}$alkyl group, which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl; and/or can optionally be interrupted by $D^{Si}$, —O—, —S—, —COO— or —OCO—;

a $C_2$-$C_{100}$alkenyl group, which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl; and/or can optionally be interrupted by $D^{Si}$, —O—, —S—, —COO— or —OCO—;

a $C_3$-$C_{100}$alkinyl group, which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl;

and/or can optionally be interrupted by $D^{Si}$, —O—, —S—, —COO— or —OCO—;

a $C_6$-$C_{12}$ cycloalkyl group, which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl; and/or can optionally be interrupted by $D^{Si}$, —O—, —S—, —COO— or —OCO—;

a $C_6$-$C_{24}$aryl group which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl; a $C_2$-$C_{20}$heteroaryl group, which can optionally be substituted one or more times with $E^{Si}$, $C_1$-$C_{12}$alkyl, $C_1$-$C_{12}$alkoxy, halogen, $C_5$-$C_{12}$cycloalkyl, cyano, $C_6$-$C_{24}$aryl, or $C_2$-$C_{20}$heteroaryl, —CO—$C_1$-$C_{18}$alkyl, —CO—$C_5$-$C_{12}$cycloalkyl, and —COO—$C_1$-$C_{18}$alkyl.

More preferably $R^1$ and $R^2$ are selected from $C_1$-$C_{50}$alkyl, especially $C_1$-$C_{25}$alkyl, which is substituted one or more times with $E^{Si}$ and/or interrupted one or more times with $D^{Si}$; $C_1$-$C_{50}$haloalkyl, especially $C_1$-$C_{25}$haloalkyl, which is substituted one or more times with $E^{Si}$ and/or interrupted one or more times with $D^{Si}$; $C_7$-$C_{25}$arylalkyl, which is substituted one or more times with $E^{Si}$ and/or interrupted one or more times with $D^{Si}$; $C_2$-$C_{50}$alkenyl, especially $C_2$-$C_{25}$alkenyl, which is substituted one or more times with $E^{Si}$ and/or interrupted one or more times with $D^{Si}$; $C_2$-$C_{50}$haloalkenyl, especially $C_2$-25haloalkenyl, which is substituted one or more times with $E^{Si}$ and/or interrupted one or more times with $D^{Si}$; $C_5$-$C_{12}$cycloalkyl; which is substituted one or more times with $E^{Si}$ and/or interrupted one or more times with $D^{Si}$; phenyl, or naphthyl which are substituted one or more times with $E^{Si}$.

Even more preferably $R^1$ and $R^2$ are $C_1$-$C_{25}$alkyl which is substituted one or more times with $E^{Si}$ and/or interrupted one or more times with $D^{Si}$; especially $C_1$-$C_{25}$alkyl which is substituted one or more times with $E^{Si}$, very especially $C_1$-$C_8$alkyl which is substituted one or more times with $E^{Si}$.

Most preferably $R^1$ and $R^2$ are $C_1$-$C_8$alkyl which is substituted with $E^{Si}$. $R^1$ and $R^2$ may be different, but are preferably the same.

$E^{Si}$ is —SiR$^{161}$R$^{162}$R$^{163}$, or —O—SiR$^{161}$R$^{162}$R$^{163}$, preferably —SiR$^{161}$R$^{162}$R$^{163}$.

$D^{Si}$ is —SiR$^{161}$R$^{162}$—, —SiR$^{161}$R$^{162}$—(O—SiR$^{161}$R$^{162}$)$_d$—, or —O—SiR$^{161}$R$^{162}$—, preferably —SiR$^{161}$R$^{162}$—, or —SiR$^{161}$R$^{162}$—(O—SiR$^{161}$R$^{162}$)$_d$—.

R$^{161}$, R$^{162}$ and R$^{163}$ are independently of each other hydrogen, C$_1$-C$_{25}$alkyl, C$_3$-C$_{12}$cycloalkyl, which might optionally be substituted with C$_1$-C$_4$alkyl; C$_1$-C$_{25}$haloalkyl, C$_2$-C$_{25}$alkenyl, —O—SiR$^{164}$R$^{165}$R$^{166}$, —(O—SiR$^{164}$R$^{165}$)$_d$—R$^{166}$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl, which is substituted 1 to 3 times by C$_1$-C$_{24}$alkyl, halogen, cyano or C$_1$-C$_{25}$alkoxy; preferably hydrogen, C$_1$-C$_{25}$alkyl, C$_3$-C$_{12}$cycloalkyl, which might optionally be substituted with C$_1$-C$_4$alkyl; C$_1$-C$_{25}$haloalkyl, C$_2$-C$_{25}$alkenyl, —O—SiR$^{164}$R$^{165}$R$^{166}$, —O—(SiR$^{164}$R$^{165}$)$_d$—R$^{166}$ or phenyl; more preferably C$_1$-C$_8$alkyl, C$_5$-C$_6$cycloalkyl, which might optionally be substituted with C$_1$-C$_4$alkyl; C$_1$-C$_8$haloalkyl, C$_2$-C$_8$alkenyl, —O—SiR$^{164}$R$^{165}$R$^{166}$, —(O—SiR$^{164}$R$^{165}$)$_d$—R$^{166}$ or phenyl; most preferably C$_1$-C$_8$alkyl, C$_1$-C$_8$haloalkyl, especially C$_1$-C$_8$alkyl which is substituted one, or more times with fluorine atoms; —O—SiR$^{164}$R$^{165}$R$^{166}$ or —(O—SiR$^{164}$R$^{165}$)$_d$—R$^{166}$.

R$^{164}$, R$^{165}$ and R$^{166}$ are independently of each other hydrogen, C$_1$-C$_{25}$alkyl, C$_3$-C$_{12}$cycloalkyl, which might optionally be substituted with C$_1$-C$_4$alkyl; C$_1$-C$_{25}$haloalkyl, C$_2$-C$_{25}$alkenyl, —O—SiR$^{169}$R$^{170}$R$^{171}$, —(O—SiR$^{16}$R$^{170}$)$_d$—R$^{171}$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl, which is substituted 1 to 3 times by C$_1$-C$_{24}$alkyl, halogen, cyano or C$_1$-C$_{25}$alkoxy; preferably hydrogen, C$_1$-C$_{25}$alkyl, C$_1$-C$_{25}$haloalkyl, C$_2$-C$_{25}$alkenyl, —O—SiR$^{16}$R$^{170}$R$^{171}$, —(O—SiR$^{16}$R$^{170}$)$_d$—R$^{171}$, or phenyl; more preferably C$_1$-C$_8$alkyl, C$_1$-C$_8$haloalkyl, C$_2$-C$_8$alkenyl, —O—SiR$^{169}$R$^{170}$R$^{171}$, —(O—SiR$^{169}$R$^{170}$)$_d$—R$^{171}$, or phenyl; most preferably C$_1$-C$_8$alkyl, C$_1$-C$_8$haloalkyl, especially C$_1$-C$_8$alkyl which is substituted one or more times with fluorine atoms; —O—SiR$^{169}$R$^{170}$R$^{171}$ or —(O—SiR$^{169}$R$^{170}$)$_d$—R$^{171}$.

R$^{169}$, R$^{170}$ and R$^{171}$ are independently of each other hydrogen, C$_1$-C$_{25}$alkyl, C$_3$-C$_{12}$cycloalkyl, which might optionally be substituted with C$_1$-C$_4$alkyl, C$_1$-C$_{25}$haloalkyl, C$_2$-C$_{25}$alkenyl, —O—Si(CH$_3$)$_3$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl, which is substituted 1 to 3 times by C$_1$-C$_{25}$alkyl, halogen, cyano, or C$_1$-C$_{25}$alkoxy; preferably hydrogen, C$_1$-C$_{25}$alkyl, C$_1$-C$_{25}$haloalkyl, C$_1$-C$_{25}$alkenyl, —O—Si(CH$_3$)$_3$, or phenyl; more preferably C$_1$-C$_8$alkyl, C$_1$-C$_8$haloalkyl, C$_2$-C$_8$alkenyl, —O—Si(CH$_3$)$_3$, or phenyl; most preferably C$_1$-C$_8$alkyl, C$_1$-C$_8$haloalkyl, especially C$_1$-C$_8$alkyl which is substituted one or more times with fluorine atoms; or —O—Si(CH$_3$)$_3$.

d is an integer from 1 to 50, especially 1 to 40, very especially 1 to 30, preferably 1 to 20, more preferably 1 to 15, still more preferably 1 to 10, even more preferably 1 to 5 and most preferably 1 to 3.

R$^{167}$ and R$^{168}$ are independently of each other hydrogen, C$_1$-C$_{25}$alkyl, C$_1$-C$_{25}$haloalkyl, C$_2$-C$_{25}$alkenyl, or phenyl; preferably C$_1$-C$_{25}$alkyl, C$_1$-C$_{25}$haloalkyl, or phenyl; most preferably C$_1$-C$_{25}$alkyl.

In a particularly preferred embodiment $E^{Si}$ is —SiR$^{161}$R$^{162}$R$^{163}$. R$^{161}$, R$^{162}$ and R$^{163}$ are independently of each other C$_1$-C$_{25}$alkyl, especially C$_1$-C$_8$alkyl; C$_1$-C$_2$haloalkyl, especially C$_1$-C$_8$haloalkyl, such as, for example, —CF$_3$, —(CH$_2$)$_2$CF$_3$, —(CH$_2$)$_2$(CF$_2$)$_5$CF$_3$ and —(CH$_2$)$_2$(CF$_2$)$_6$CF$_3$; C$_2$-C$_{25}$alkenyl, especially C$_2$-C$_8$alkenyl; C$_3$-C$_{12}$ cycloalkyl, especially C$_5$-C$_6$cycloalkyl, which might optionally be substituted with C$_1$-C$_4$alkyl; phenyl, —O—SiR$^{164}$R$^{165}$R$^{166}$, or —(O—SiR$^{164}$R$^{165}$)$_d$—R$^{166}$. In case of a group —O—SiR$^{164}$R$^{165}$)$_d$—R$^{166}$R$^{164}$, R$^{165}$ and R$^{166}$ are independently of each other C$_1$-C$_8$alkyl, C$_1$-C$_8$haloalkyl, C$_2$-C$_8$alkenyl, or phenyl. In case of a group —(O—SiR$^{164}$R$^{165}$)$_d$—R$^{166}$R$^{164}$ and R$^{165}$ are independently of each other C$_1$-C$_8$alkyl, R$^{166}$ is C$_1$-C$_8$alkyl, or phenyl and d is an integer of 2 to 5.

Examples of preferred groups $E^{Si}$ are shown below:

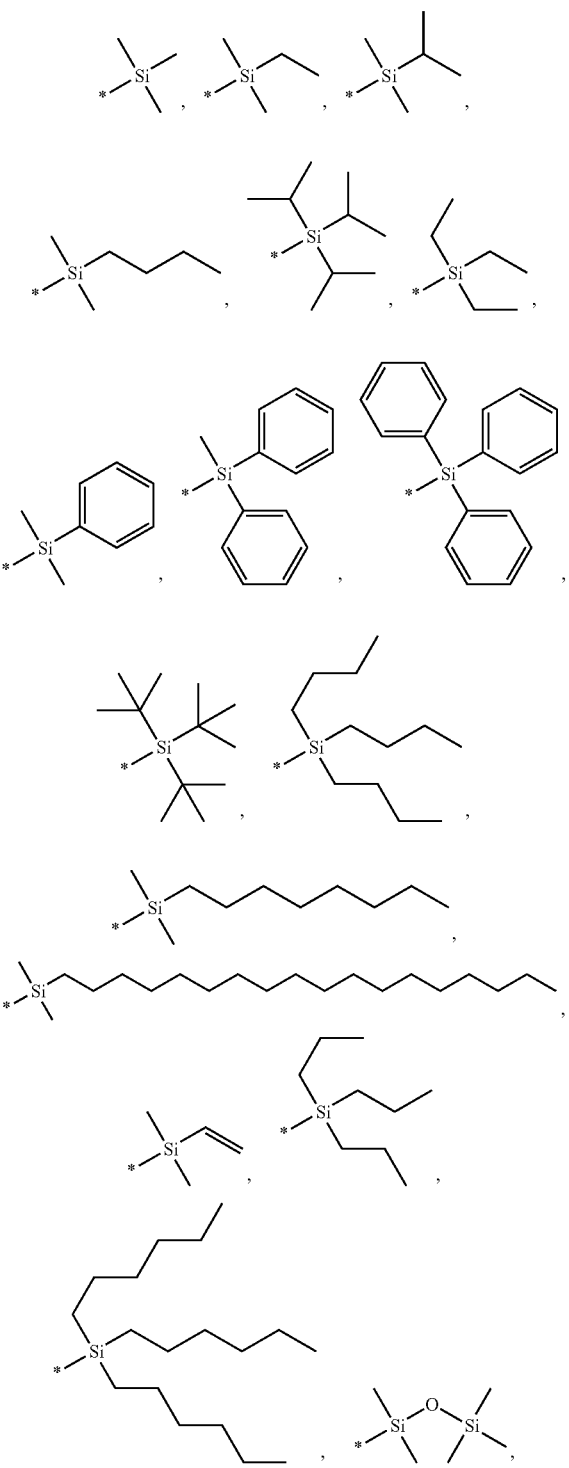

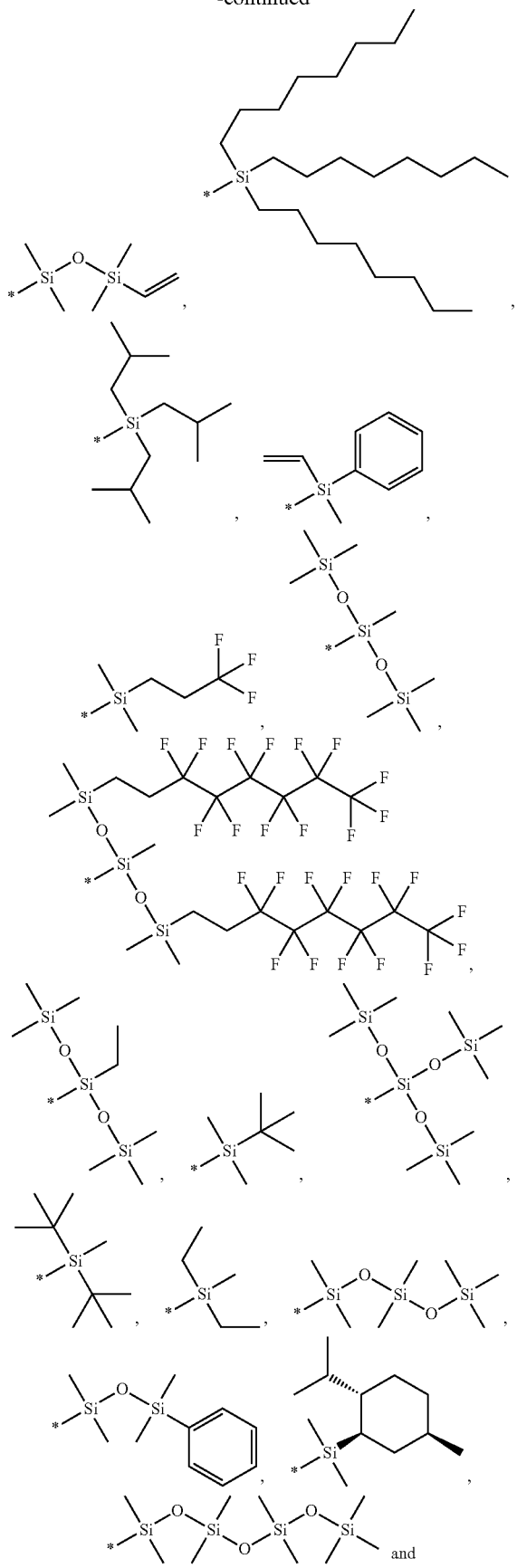

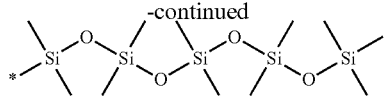

(*- indicates the bond to the carbon atom, to which the silyl group or siloxanyl group is connected).

In a particularly preferred embodiment $D^{Si}$ is —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl.

In another particularly preferred embodiment $D^{Si}$ is —$SiR^{161}R^{162}$(O—$SiR^{161}R^{162})_d$—, wherein d is 2 to 5 and $R^{161}$ and $R^{162}$ are $C_1$-$C_{25}$alkyl, especially $C_1$-$C_8$alkyl.

Examples of preferred groups $D^{Si}$ are shown below:

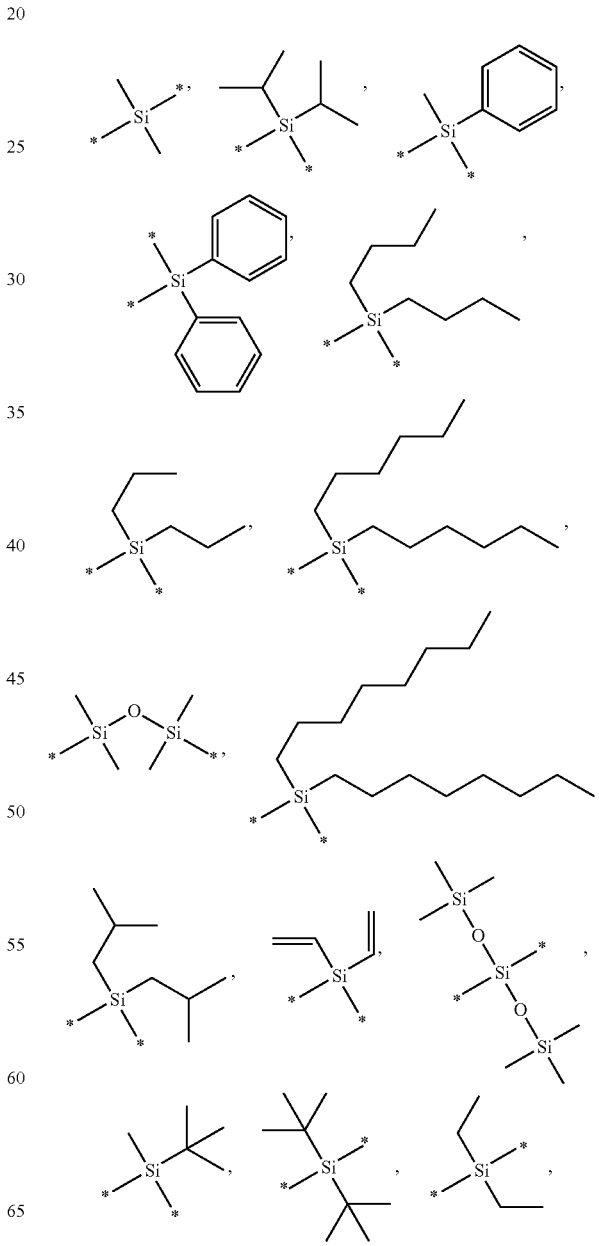

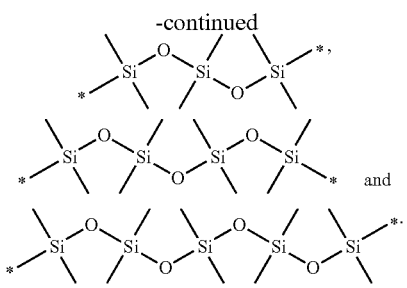

Preferably at least one of $R^1$ and $R^2$ comprise a group $E^{Si}$ and/or $D^{Si}$. $R^1$ and $R^2$ are preferably the same.

Chiral side chains, such as $R^1$ and $R^2$ can either be homochiral, or racemic, which can influence the morphology of the compounds.

Preferably $Ar^1$ and $Ar^{1'}$ are independently of each other a group of formula XIa, XIb, XIc, XIe, XIf, XII, XIp, XIr, XIs, XIx, XIIf, XIIg, XIIa, XIIId, or XIIII; more preferably a group of formula XIa, XIb, XIe, XIf, XIr, Xix, or XIIIa, still more preferably a group of formula XIa, XIb, or XIf, most preferred a group of formula XIa, or XIf, especially XIa.

Preferably, $R^3$ and $R^{3'}$ are independently of each other hydrogen, halogen, $E^{Si}$, $CF_3$, cyano, $C_1$-$C_{25}$alkyl, $C_1$-$C_{25}$alkyl substituted with one or more $E^{Si}$, or $C_1$-$C_{25}$alkoxy; more preferably $CF_3$, cyano or $C_1$-$C_{25}$alkyl; most preferred hydrogen, or $C_1$-$C_{25}$alkyl;

Preferably, $R^{104}$ and $R^{104'}$ are independently of each other hydrogen, cyano or a $C_1$-$C_{25}$alkyl group, more preferably hydrogen, or a $C_1$-$C_{25}$alkyl group, most preferred hydrogen.

Preferably, $R^4$, $R^{4'}$, $R^5$, $R^{5'}$, $R^6$ and $R^{6'}$ are independently of each other hydrogen, halogen, $E^{Si}$, $CF_3$, cyano, $C_1$-$C_{25}$alkyl, $C_1$-$C_{25}$alkyl substituted with one or more $E^{Si}$, or $C_1$-$C_{25}$alkoxy, more preferably hydrogen, $CF_3$, cyano or $C_1$-$C_{25}$alkyl; most preferred hydrogen, or $C_1$-$C_{25}$alkyl.

Preferably $R^7$, $R^{7'}$, $R^9$ and $R^{9'}$ are independently of each other hydrogen, $C_1$-$C_{25}$alkyl, $C_1$-$C_{25}$alkyl substituted with one or more $E^{Si}$, more preferably $C_4$-$C_{25}$alkyl.

Preferably, $R^8$ and $R^{8'}$ are independently of each other hydrogen, $C_1$-$C_{25}$alkyl, $C_1$-$C_{25}$alkyl substituted with one or more $E^{Si}$, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl.

Preferably, $R^{11}$ and $R^{11'}$ are independently of each other a $C_1$-$C_{25}$alkyl group, especially a $C_1$-$C_8$alkyl group, or phenyl; more preferably a $C_1$-$C_8$alkyl group.

Preferably, $R^{12}$ and $R^{12'}$ are independently of each other hydrogen, $C_1$-$C_{25}$alkyl, $C_1$-$C_{25}$alkoxy, or ═$R^{13}$, wherein $R^{13}$ is a $C_1$-$C_{10}$alkyl group, or a tri($C_1$-$C_8$alkyl)silyl group, more preferably hydrogen, $C_1$-$C_{25}$alkyl, or $C_1$-$C_{25}$alkoxy.

If $Ar^2$, $Ar^{2'}$, $Ar^3$, $Ar^{3'}$, $Ar^4$ and $Ar^{4'}$ are independently of each other a group of formula XVa to XVh, XVI, or XVII, groups of formula XVa, XVb, XVc, XVIa, XVIb, XVIIa, and XVIIb are preferred, groups of formula XVa, XVb, XVc, XVIa, and XVIb are more preferred. Among groups of formula XVa, XVb, XVc, XVIa, and XVIb, groups of formula XVa, and XVb are most preferred.

If $Ar^2$, $Ar^{2'}$, $Ar^3$, $Ar^{3'}$, $Ar^4$ and $Ar^{4'}$ are independently of each other a group of formula XIa to XIz, XIIa to XIIk, or XIII, groups of formula XIa, XIb, XIc, XIe, XIf, XII, XIp, XIr, XIs, XIx, XIIf, XIIg, XIIIa, XIIId, and XIIII are preferred; groups of formula XIa, XIb, XIe, XIf, XIr, Xix, and XIIIa are more preferred, and groups of formula XIa, XIb, and XIf are still more preferred.

Most preferred is a group of formula XIa, or XIf, especially XIa.

Preferably, $R^{105}$, $R^{105'}$, $R^{106}$ and $R^{106'}$ are independently of each other hydrogen, halogen, cyano, $C_1$-$C_{25}$alkyl or $C_1$-$C_{18}$alkoxy, more preferably $C_1$-$C_{25}$alkyl or $C_1$-$C_{18}$alkoxy, most preferred hydrogen, or $C_1$-$C_{25}$alkyl.

$R^{107}$ is preferably hydrogen, $C_1$-$C_{25}$alkyl, $C_1$-$C_{25}$alkyl, which may optionally be interrupted by one or more oxygen or sulphur atoms; or $C_7$-$C_{25}$arylalkyl, more preferably hydrogen, or $C_1$-$C_{25}$alkyl, most preferred $C_4$-$C_{25}$alkyl.

Preferably, $R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_2$-$C_{18}$alkenyl, or $C_7$-$C_{25}$aralkyl, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, D is —CO—, —COO—, —S— or —O—, E is $C_1$-$C_8$thioalkoxy, $C_1$-$C_8$alkoxy, CN or halogen, G is E, or $C_1$-$C_{18}$alkyl. More preferably, $R^{108}$ and $R^{109}$ are independently of each other H, $C_1$-$C_{25}$alkyl or $C_7$-$C_{25}$arylalkyl. Most preferred Rile and $R^{109}$ are independently of each other H, or $C_1$-$C_{25}$alkyl.

D is preferably —CO—, —COO—, —S— or —O—, more preferably —COO—, —S— or —O—, most preferred —S— or —O—.

Preferably, E is $C_1$-$C_8$thioalkoxy, $C_1$-$C_8$alkoxy, CN, or halogen, more preferably $C_1$-$C_8$alkoxy, CN, or halogen, most preferred halogen, especially F.

Preferably, $R^{112}$ and $R^{113}$ are independently of each other H; $C_1$-$C_{18}$alkyl; or $C_1$-$C_{18}$alkyl which is interrupted by —O—, more preferably H, or $C_1$-$C_{18}$alkyl; most preferred $C_1$-$C_{18}$alkyl.

In a preferred embodiment the present invention is directed to polymers, comprising a repeating unit of the formula

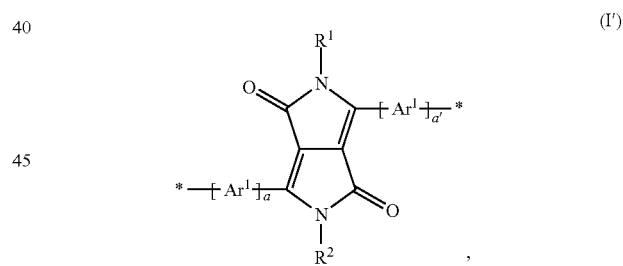

(I')

wherein
$R^1$ and $R^2$ may be the same or different and are selected from $C_1$-$C_{25}$alkyl, which is substituted one or more times with $E^{Si}$ and/or interrupted one or more times with $D^{Si}$; $C_1$-$C_{25}$haloalkyl, which is substituted one or more times with $E^{Si}$ and/or interrupted one or more times with $D^{Si}$; $C_7$-$C_{25}$arylalkyl, which is substituted one or more times with $E^{Si}$ and/or interrupted one or more times with $D^{Si}$; $C_2$-$C_{25}$alkenyl, which is substituted one or more times with $E^{Si}$ and/or interrupted one or more times with $D^{Si}$; $C_2$-$C_{25}$haloalkenyl, which is substituted one or more times with $E^{Si}$ and/or interrupted one or more times with $D^{Si}$; $C_5$-$C_{12}$cycloalkyl, which is substituted one or more times with $E^{Si}$ and/or interrupted one or more times with $D^{Si}$; phenyl, or naphthyl which are substituted one or more times with $E^{Si}$; and a is 1, 2, or 3, a' is 1, 2, or 3; wherein $D^{Si}$, $E^{Si}$, $Ar^1$ and $Ar^{1'}$ are as defined above.

In said embodiment the following preferences apply with respect to the substituents:

$R^1$ and $R^2$ may be the same or different and are selected from $C_1$-$C_{25}$alkyl, which is substituted one or more times with $E^{Si}$ and/or interrupted one or more times with $D^{Si}$. $R^1$ and $R^2$ may be different, but are preferably the same.

$D^{Si}$ is preferably —$SiR^{161}R^{162}$—, wherein $R^{161}$ and $R^{162}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; or phenyl.

$E^{Si}$ is preferably —$SiR^{161}R^{162}R^{163}$. $R^{161}$, $R^{162}$ and $R^{163}$ are independently of each other $C_1$-$C_{25}$alkyl, especially $C_1$-$C_8$alkyl; $C_1$-$C_{25}$haloalkyl, especially $C_1$-$C_8$haloalkyl, such as, for example, —$CF_3$, —$(CH_2)_2CF_3$, —$(CH_2)_2(CF_2)_5CF_3$ and —$(CH_2)_2(CF_2)_6CF_3$; $C_2$-$C_{25}$alkenyl, especially $C_2$-$C_8$alkenyl; $C_3$-$C_{12}$cycloalkyl, especially $C_5$-$C_6$cycloalkyl, which might optionally be substituted with $C_1$-$C_4$alkyl; phenyl, —O—$SiR^{164}R^{165}R^{166}$, or —(O—$SiR^{164}R^{165})_d$—$R^{166}$.

a and a' may be different, but are preferably the same. a and a' are preferably 1, or 2, more preferably 1.

$Ar^1$ and $Ar^{1'}$ are preferably selected from groups of formula XIa to XIz, XIIa to XIIIk, XIII, especially XIIIa to XIIII, and XIV. $Ar^1$ and $Ar^{1'}$ may be different, but are preferably the same. More preferably, $Ar^1$ and $Ar^{1'}$ are independently of each a group of formula XIa, XIb, XIc, XIe, XIf, XII, XIp, XIr, XIs, XIx, XIIIf, XIIg, XIIIa, XIIId, or XIIII (as defined above).

Even more preferably, $Ar^1$ and $Ar^{1'}$ are a group of formula XIa, XIb, XIe, XIf, XIr, XIx, or XIIIa. Still more preferably $Ar^1$ and $Ar^{1'}$ are a group of formula XIa, XIb, or XIf. Most preferred $Ar^1$ and $Ar^{1'}$ are a group of formula XIa, or XIf, especially XIa.

In a further preferred embodiment the present invention is directed to polymers, comprising a repeating unit of the formula

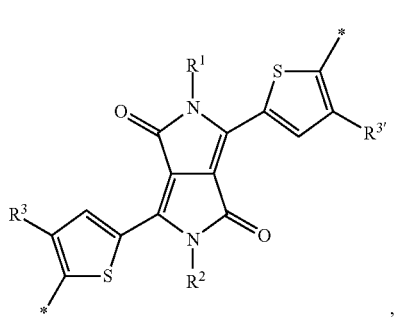
(Ia)

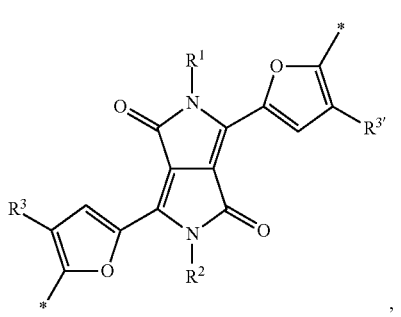
(Ib)

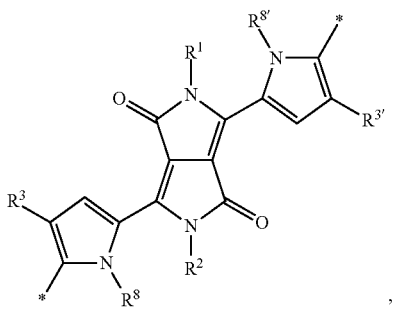
(Ic)

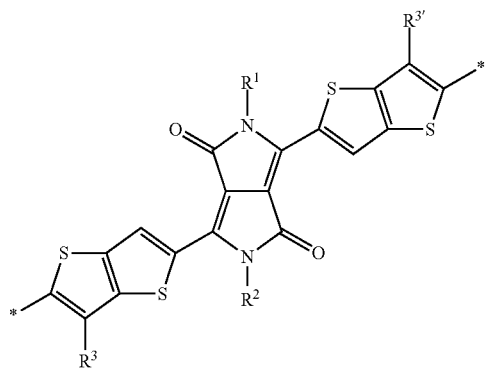
(Id)

and/or

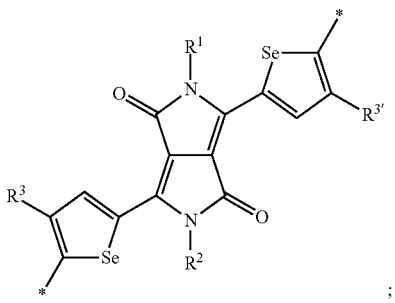
(Ie)

wherein
$R^1$ and $R^2$ may be the same or different and are selected from $C_1$-$C_8$alkyl which is substituted with $E^{Si}$,
$E^{Si}$ is —$SiR^{161}R^{162}R^{163}$;
$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;
$R^{164}$, $R^{165}$, $R^{166}$ are independently of each other $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;
$R^{169}$, $R^{170}$, $R^{171}$ are independently of each other $C_1$-$C_8$alkyl, $C_1$-$C_8$haloalkyl, $C_2$-$C_8$alkenyl, —O—$Si(CH_3)_3$, or phenyl;
d is an integer from 1 to 10;

In said embodiment the following preferences apply with respect to the substituents:
$R^3$ and $R^{3'}$ are independently of each other hydrogen, or $C_1$-$C_{25}$alkyl; and
$R^8$ and $R^{8'}$ are independently of each other hydrogen, or $C_1$-$C_{25}$alkyl.

Repeating) unit(s) of the formula (Ia), (Ib) and (Id) are preferred; repeating unit(s) of the formula (Ia) and (Id) are more preferred; repeating unit(s) of the formula (Ia) are most preferred.

In another embodiment the present invention is directed to polymers, comprising repeating units of the formula *─[─A─]─* and *─[─COM¹─]─*, wherein
A is a repeating unit of formula (I), and
─COM¹─ is a repeating unit, which has the meaning of $Ar^2$, wherein $Ar^2$ is as defined in claim 1, or is a group of formula *─[─$Ar^{14}$─]$_s$─[─$Ar^{15}$─]$_t$─[─$Ar^{16}$─]$_u$─[─$Ar^{17}$─]$_v$─*, s is 1, t is 1, u is 0, or 1, v is 0, or 1, and
$Ar^{14}$, $Ar^{15}$, $Ar^{16}$ and $Ar^{17}$ have independently of each other the meaning of $Ar^2$.
$Ar^{14}$, $Ar^{15}$, $Ar^{16}$ and $Ar^{17}$ are preferably independently of each other a group of formula

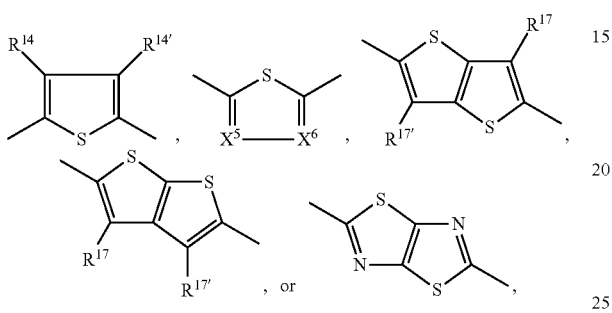

wherein one of $X^5$ and $X^6$ is N and the other is $CR^{14}$, and $R^{14}$, $R^{14'}$, $R^{17}$ and $R^{17'}$ are independently of each other H, or a $C_1$-$C_{25}$alkyl group.

Examples of repeating units ─COM¹─ are groups of formula XIa, XIb, XIc, XIe, XIf, XII, XIp, XIr, XIs, XIx, XIIf, XIIg, XIIIa, XIIId, XIIII, XVa, XVb, XVc, XVIa, XVIb, XVIIa, or XVIIb. Among these groups of formula XIa, XIb, XIe, XIf, XIr, XIx, XIIIa, XVa, XVb, XVc, XVIa, or XVIb are preferred, groups of formula XIa, XIb, XIf, XVa, or XVb are more preferred, groups of formula XIa, XIf, or XVa are still more preferred. Groups of formula XIa are most preferred.

Examples of a group of formula *─[─$Ar^{14}$─]$_k$─[─$Ar^{15}$─]$_l$─[─$Ar^{16}$─]$_r$─[─$Ar^{17}$─]$_z$─* are

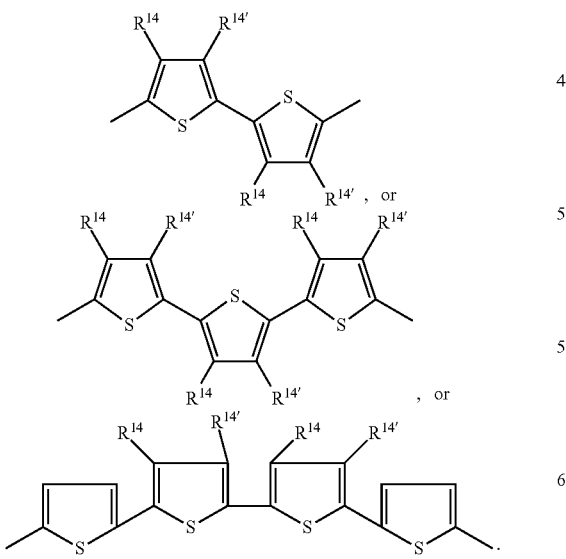

If substituents, such as, for example, $R^{14}$ and $R^{14'}$, appear more than one time in a formula they can be the same, or different.

In a particularly preferred embodiment the repeating unit ─COM¹─ is a group of formula

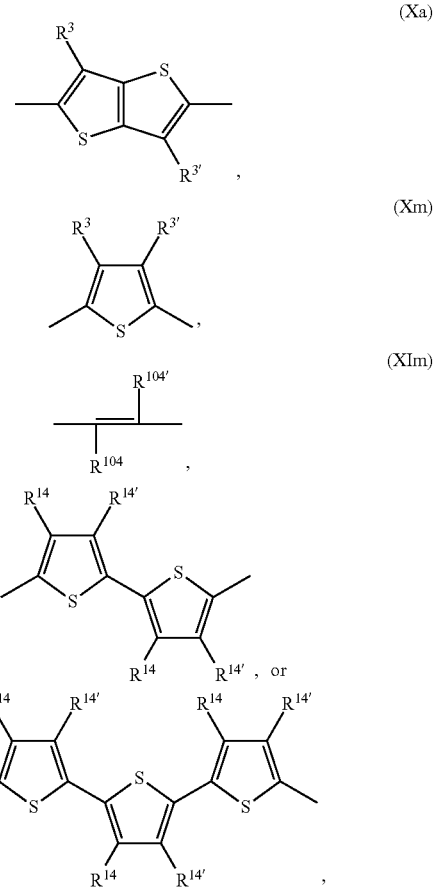

where $R^3$, $R^{3'}$, $R^{14}$ and $R^{14'}$ are independently of each other hydrogen, or $C_1$-$C_{25}$alkyl, and $R^{104}$ and $R^{104'}$ are independently of each other hydrogen, cyano or a $C_1$-$C_{25}$alkyl group.

In a preferred embodiment of the present invention the polymer is a copolymer, comprising repeating units of formula *─[─A─]─[─COM¹─]─* (VII), especially a copolymer of formula, wherein A and COM¹ are as defined above; n is a number which results in a molecular weight of 4,000 to 2,000,000 Daltons, more preferably 10,000 to 1,000,000 and most preferably 10,000 to 100,000 Daltons. n is usually in the range of 4 to 1000, especially 4 to 200, very especially 5 to 150.

In a preferred embodiment the present invention is directed to polymers, wherein A is a repeating unit of formula (Ia), or (Id), (as defined above) and *─[─COM¹─]─* is a group of formula

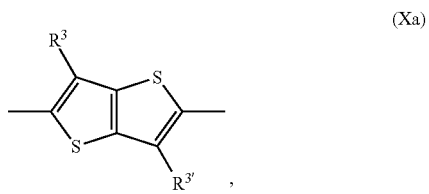

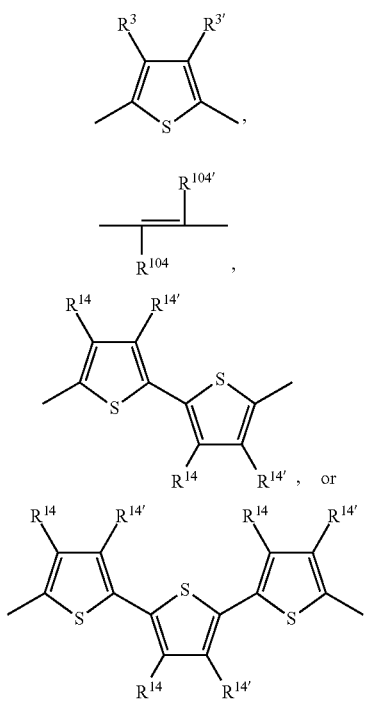

where $R^3$, $R^{3'}$, $R^{14}$ and $R^{14'}$ are independently of each other hydrogen, or $C_1$-$C_{25}$alkyl, and $R^{104}$ and $R^{104'}$ are independently of each other hydrogen, cyano or a $C_1$-$C_{25}$alkyl group.

In a preferred embodiment the present invention is directed to copolymers, wherein *—[—A—]—* is

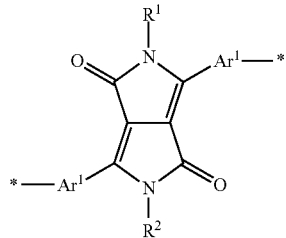

and *—[—COM$^1$—]—* is Ar$^2$—, or —Ar$^2$—Ar$^3$—; especially Ar$^2$—, or —Ar$^{14}$—Ar$^{15}$—; very especially —Ar$^2$—. *—[—A—]—* is preferably

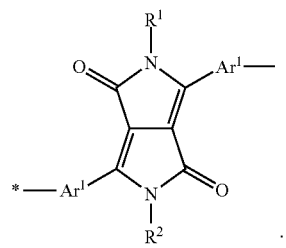

Among the polymers of formula I the following polymers are preferred:

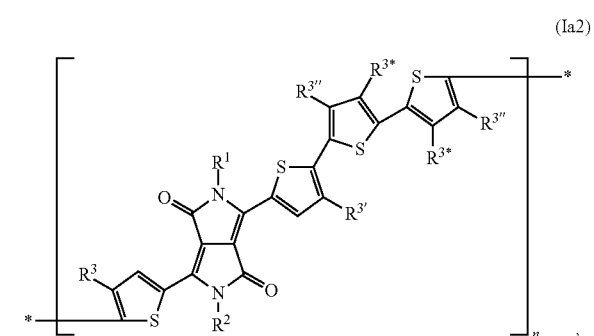

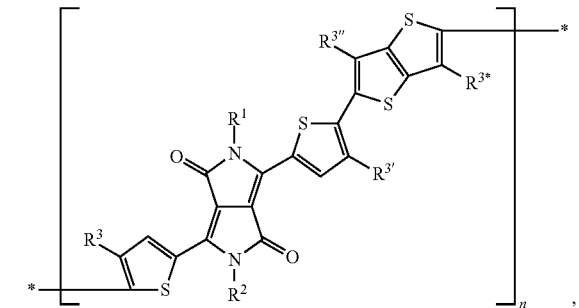

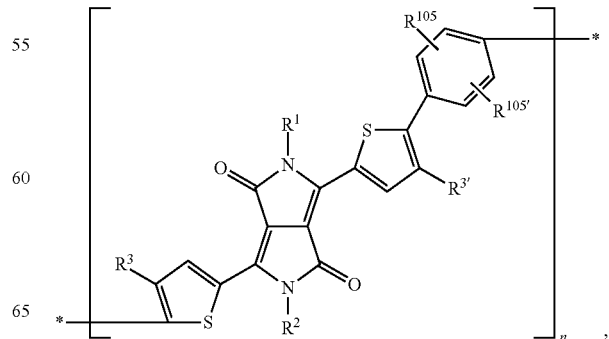

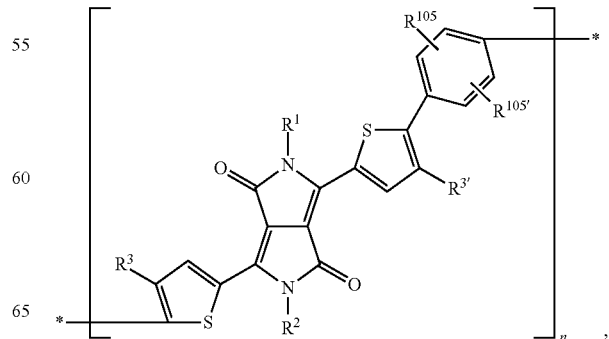

-continued

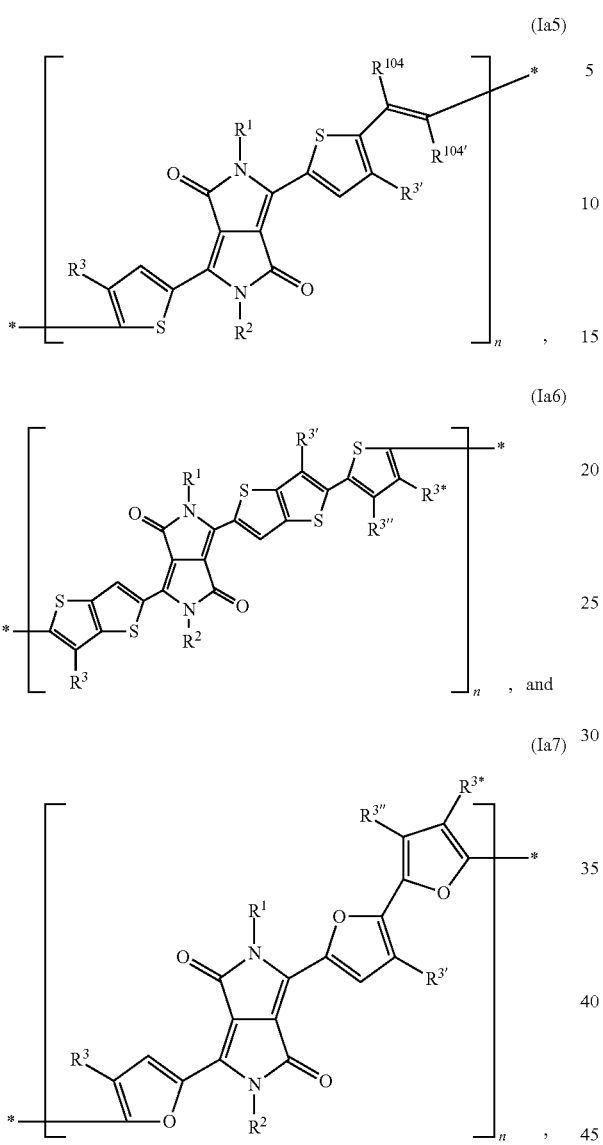

wherein
n is 4 to 1000,
R¹ and R² may be the same or different and are selected from C$_1$-C$_8$alkyl which is substituted with E$^{Si}$,
R³ and R³' are independently of each other hydrogen, halogen, cyano, C$_1$-C$_{25}$alkyl or C$_1$-C$_{25}$alkoxy;
E$^{Si}$ is —SiR$^{161}$R$^{162}$R$^{163}$;
R$^{161}$, R$^{162}$ and R$^{163}$ are independently of each other C$_1$-C$_8$alkyl, C$_5$-C$_6$cycloalkyl, which might optionally be substituted with C$_1$-C$_4$alkyl; C$_1$-C$_8$haloalkyl, C$_2$-C$_8$alkenyl, —O—SiR$^{164}$R$^{165}$R$^{166}$, —(O—SiR$^{164}$R$^{165}$)$_d$—R$^{166}$, or phenyl;
R$^{164}$, R$^{165}$ and R$^{166}$ are independently of each other C$_1$-C$_8$alkyl, C$_1$-C$_8$haloalkyl, C$_2$-C$_8$alkenyl, —O—SiR$^{169}$R$^{170}$R$^{171}$, —(O—SiR$^{169}$R$^{170}$)$_d$—R$^{171}$, or phenyl;
R$^{169}$, R$^{170}$ and R$^{171}$ are independently of each other C$_1$-C$_8$alkyl, C$_1$-C$_8$haloalkyl, C$_2$-C$_8$alkenyl, —O—Si(CH$_3$)$_3$, or phenyl;
d is an integer from 1 to 10;

R³'' and R³* are independently of each other hydrogen, halogen, cyano, C$_1$-C$_{25}$alkyl or C$_1$-C$_{25}$alkoxy;
R$^{104}$ and R$^{104'}$ are independently of each other hydrogen, cyano, COOR$^{103}$, or C$_1$-C$_{25}$alkyl, especially hydrogen, cyano, or COOR$^{103}$, wherein R$^{103}$ is C$_1$-C$_8$alkyl; and
R$^{105}$ and R$^{105'}$ are independently of each other hydrogen, halogen, cyano, C$_1$-C$_{25}$alkyl or C$_1$-C$_{25}$alkoxy, especially hydrogen, cyano, or C$_1$-C$_{25}$alkyl.

Examples of particular preferred polymers are shown below:

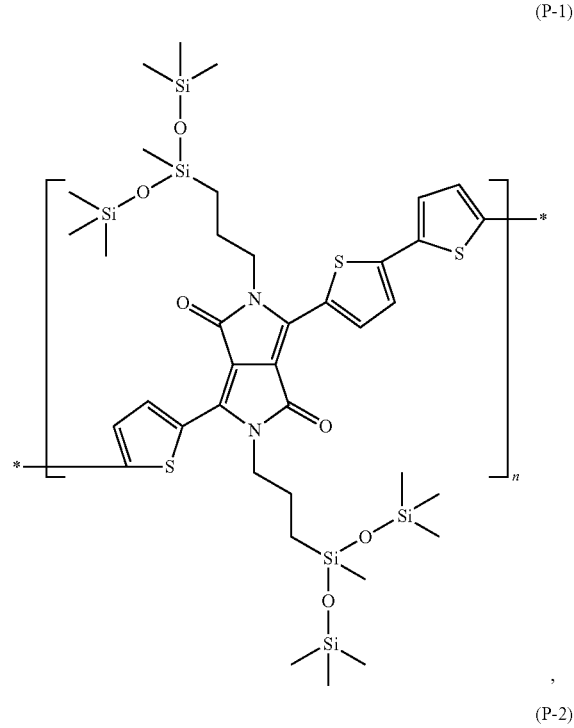
(P-1)

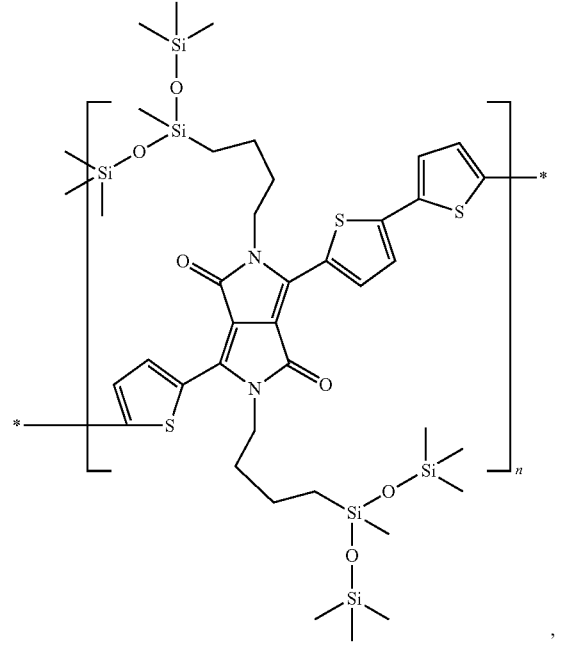
(P-2)

-continued
(P-3)
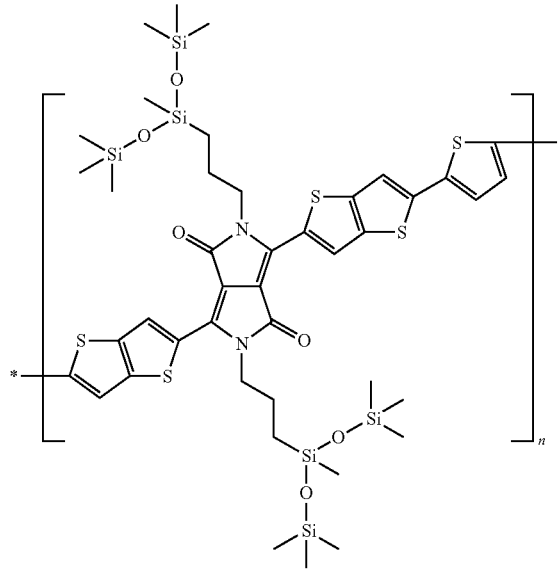
(P-4)
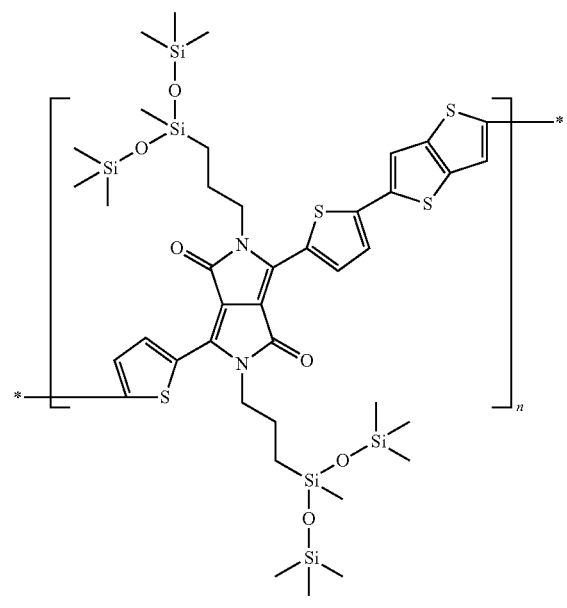
(P-5)
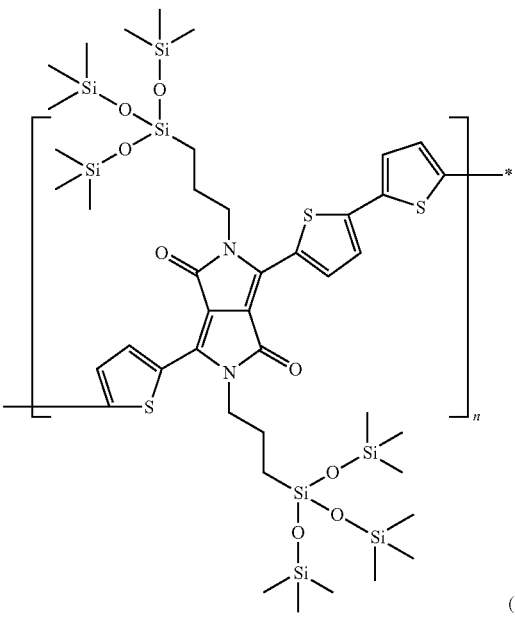
(P-6)
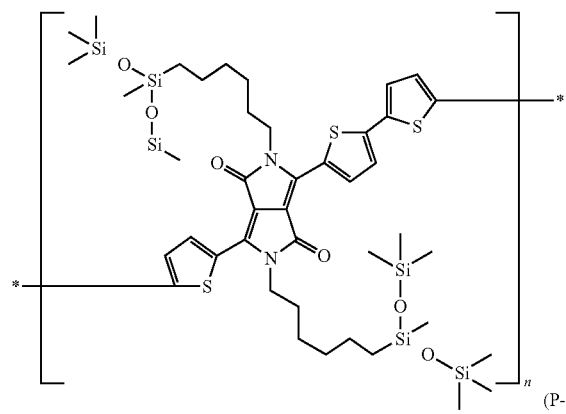
(P-7)
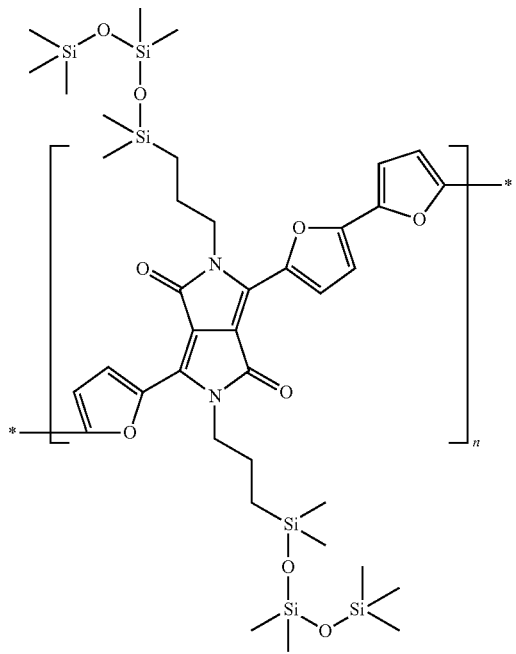

(P-8)

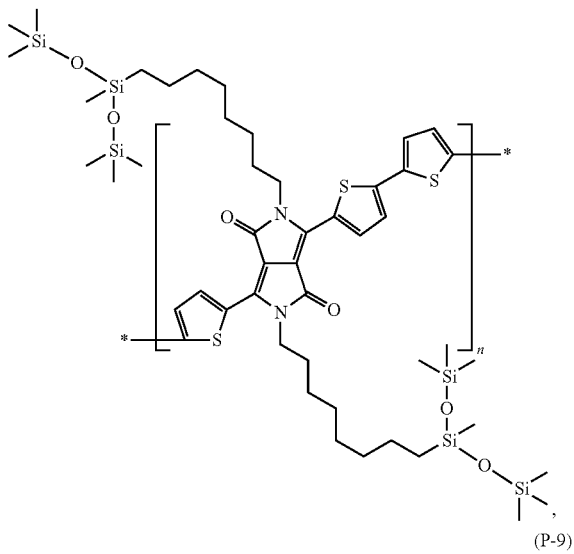

(P-9)

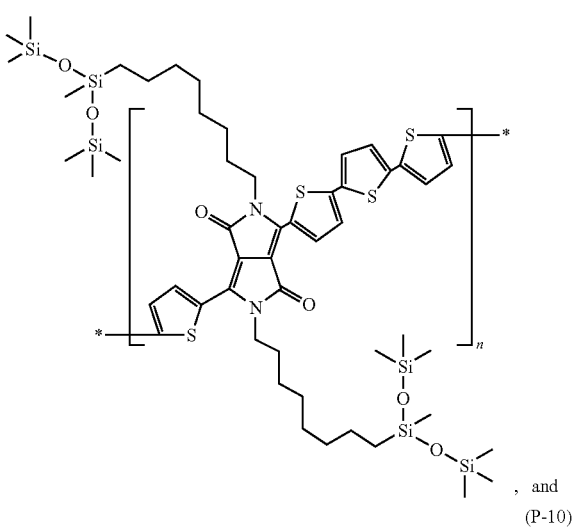

, and (P-10)

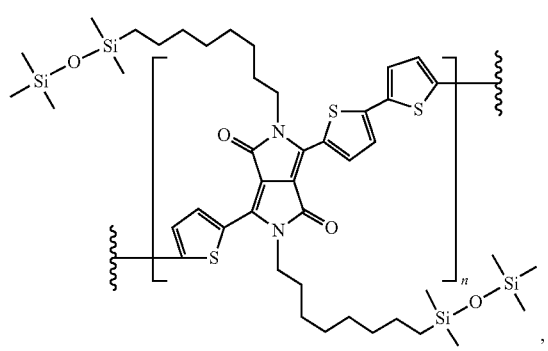

, wherein n is usually in the range of 4 to 1000, especially 4 to 200, very especially 5 to 150.

The polymers of the present invention can comprise more than 2 different repeating units, such as, for example, repeating units A, B and D, which are different from each other. If the polymers comprise repeating units of the formula *−[A-D−]−* and *−[B-D−]−*, they are preferably (random) copolymers of formula *−[A-D*−]$_x$-*−[B-D−]$_y$*, wherein x=0.995 to 0.005, y=0.005 to 0.995, especially x=0.2 to 0.8, y=0.8 to 0.2, and wherein x+y=1. A is a repeating unit of formula (I), D* is a repeating unit —COM$^1$— and B is a repeating unit —COM$^1$—, or a repeating unit of formula (I); with the proviso that A, B and D* are different from each other.

Copolymers of formula VII can be obtained, for example, by the Suzuki reaction. The condensation reaction of an aromatic boronate and a halogenide, especially a bromide, commonly referred to as the "Suzuki reaction", is tolerant of the presence of a variety of organic functional groups as reported by N. Miyaura and A. Suzuki in Chemical Reviews, Vol. 95, pp. 457-2483 (1995). Preferred catalysts are 2-dicyclohexylphosphino-2',6'-dialkoxybiphenyl/palladium(II)acetates, tri-alkyl-phosphonium salts/palladium (0) derivatives and tri-alkylphosphine/palladium (0) derivatives. Especially preferred catalysts are 2-dicyclohexylphosphino-2',6'-di-methoxybiphenyl (sPhos)/palladium(II)acetate and, tri-tertbutylphosphonium tetrafluoroborate ((t-Bu)$_3$P*HBF$_4$)/tris(dibenzylideneacetone)dipalladium (0) (Pd$_2$(dba)$_3$) and tri-tert-butyiphosphine (t-Bu)$_3$P/tris(dibenzylideneacetone) dipalladium (0) (Pd$_2$(dba)$_3$). This reaction can be applied to preparing high molecular weight polymers and copolymers.

To prepare polymers corresponding to formula VII a dihalogenide of formula X$^{10}$-A-X$^{10}$ is reacted with an (equimolar) amount of a diboronic acid or diboronate corresponding to formula X$^{11}$−[COM$^1$−]−X$^{11}$; or a dihalogenide of formula X$^{10}$−[COM$^1$−]−X$^{10}$ is reacted with an (equimolar) amount of a diboronic acid or diboronate corresponding to formula X$^{11}$-A-X$^{11}$, wherein X$^{10}$ is halogen, especially Br, and X$^{11}$ is independently in each occurrence —B(OH)$_2$, —B(OY$^1$)$_2$, $$-B\begin{pmatrix}O\\O\end{pmatrix}\begin{pmatrix}Y^{13}\\Y^{14}\end{pmatrix}, \text{ or } -B\begin{pmatrix}O\\O\end{pmatrix}\begin{pmatrix}Y^2\\\end{pmatrix},$$

wherein Y$^1$ is independently in each occurrence a C$_1$-C$_{10}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$—Cy$^{11}$Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{10}$alkyl group, especially —C(CH$_3$)$_2$C(CH$_3$)$_2$—, —CH$_2$C(CH$_3$)$_2$CH$_2$—, or —C(CH$_3$)$_2$CH$_2$C(CH$_3$)$_2$—, and Y$^{13}$ and Y$^{14}$ are independently of each other hydrogen, or a C$_1$-C$_{10}$alkyl group, under the catalytic action of Pd and triphenylphosphine. The reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A polymerization reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

Control of molecular weight is possible by using either an excess of dibromide, diboronic acid, or diboronate, or a chain terminator.

According to the process described in WO2010/136352 the polymerisation is carried out in presence of
a) a catalyst/ligand system comprising a palladium catalyst and an organic phosphine or phosphonium compound,
b) a base,
c) a solvent or a mixture of solvents, characterized in that the organic phosphine is a trisubstituted phosphine of formula

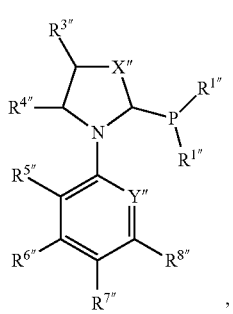

(VI)

or phosphonium salt thereof, wherein X" independently of Y" represents a nitrogen atom or a C—$R^{2"}$ group and Y" independently of X" represents a nitrogen atom or a C—$R^{9"}$ group, $R^{1"}$ for each of the two $R^{1"}$ groups independently of the other represents a radical selected from the group $C_1$-$C_{24}$-alkyl, $C_3$-$C_{20}$-cycloalkyl, which includes especially both monocyclic and also bi- and tri-cyclic cycloalkyl radicals, $C_5$-$C_{14}$-aryl, which includes especially the phenyl, naphthyl, fluorenyl radical, $C_2$-$C_{13}$-heteroaryl, wherein the number of hetero atoms, selected from the group N, O, S, may be from 1 to 2, wherein the two radicals $R^{1"}$ may also be linked to one another,
and wherein the above-mentioned radicals $R^{1"}$ may themselves each be mono- or poly-substituted independently of one another by substituents selected from the group hydrogen, $C_1$-$C_{20}$-alkyl, $C_{2-20}$-alkenyl, $C_3$-$C_8$-cycloalkyl, $C_2$-$C_9$-hetero-alkyl, $C_5$-$C_{10}$-aryl, $C_2$-$C_9$-heteroaryl, wherein the number of hetero atoms from the group N, O, S may be from 1 to 4, $C_1$-$C_{20}$-alkoxy, $C_1$-$C_{10}$-haloalkyl, hydroxy, amino of the forms NH—($C_1$-$C_{20}$-alkyl), NH—($C_5$-$C_{10}$-aryl), N($C_1$-$C_{20}$-alkyl)$_2$, N($C_1$-$C_{20}$-alkyl) ($C_5$-$C_{10}$-aryl), N($C_5$-$C_{10}$-aryl)$_2$, N($C_1$-$C_{20}$-alkyl/$C_5$-$C_{10}$-aryl$_3$)$_3^+$, NH—CO—$C_1$-$C_{20}$-alkyl, NH—CO—$C_5$-$C_{10}$-aryl, carboxylato of the forms COOH and COOQ (wherein Q represents either a monovalent cation or $C_1$-$C_8$-alkyl), $C_1$-$C_6$-acyloxy, sulfinato, sulfonato of the forms $SO_3H$ and $SO_3Q'$ (wherein Q' represents either a monovalent cation, $C_1$-$C_{20}$-alkyl, or $C_5$-$C_{10}$-aryl), tri-$C_1$-$C_6$-alkylsilyl, wherein two of the mentioned substituents may also be bridged with one another, $R^{2"}$-$R^{9"}$ represent a hydrogen, alkyl, alkenyl, cycloalkyl, aromatic or heteroaromatic aryl, O-alkyl, NH— alkyl, N-(alkyl)$_2$, O-(aryl), NH-(aryl), N-(alkyl)(aryl), O—CO-alkyl, O—CO-aryl, F, Si(alkyl)$_3$, $CF_3$, CN, $CO_2H$, COH, $SO_3H$, $CONH_2$, CONH(alkyl), CON(alkyl)$_2$, $SO_2$(alkyl), SO(alkyl), SO(aryl), $SO_2$(aryl), $SO_3$(alkyl), $SO_3$(aryl), S-alkyl, S-aryl, NH—CO(alkyl), $CO_2$(alkyl), $CONH_2$, CO(alkyl), NHCOH, $NHCO_2$(alkyl), CO(aryl), $CO_2$(aryl) radical, wherein two or more adjacent radicals, each independently of the other (s), may also be linked to one another so that a condensed ring system is present and wherein in $R^{2"}$ to $R^{9"}$ alkyl represents a hydrocarbon radical having from 1 to 20 carbon atoms which may in each case be linear or branched, alkenyl represents a mono- or poly-unsaturated hydrocarbon radical having from 2 to 20 carbon atoms which may in each case be linear or branched, cycloalkyl represents a hydrocarbon having from 3 to 20 carbon atoms, aryl represents a 5- to 14-membered aromatic radical, wherein from one to four carbon atoms in the aryl radical may also be replaced by hetero atoms from the group nitrogen, oxygen and sulfur so that a 5- to 14-membered heteroaromatic radical is present, wherein the radicals $R^{2"}$ to $R^{9"}$ may also carry further substituents as defined for $R^{1"}$.

The organic phosphines and their synthesis are described in WO2004101581.

Preferred organic phosphines are selected from trisubstituted phosphines of formula

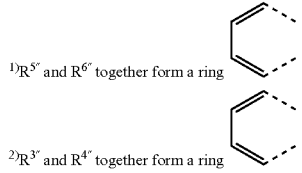

| Cpd. | $R^{1"}$ | $R^{5"}$ | $R^{6"}$ | $R^{3"}$ | $R^{4"}$ |
|------|---------|---------|---------|---------|---------|
| A-1 | H$_3$C-C(CH$_3$)(CH$_3$) | H | H | H | H |
| A-2 | cyclohexyl | H | H | H | H |
| A-3 | phenyl | H | H | H | H |
| A-4 | adamantyl | H | H | H | H |
| A-5 | cyclohexyl | —OCH$_3$ | H | H | H |
| A-6 | cyclohexyl | 1) | 1) | H | H |
| A-7 | H$_3$C-C(CH$_3$)(CH$_3$) | 1) | 1) | H | H |
| A-8 | phenyl | 1) | 1) | H | H |
| A-9 | adamantyl | 1) | 1) | H | H |
| A-10 | cyclohexyl | H | H | 2) | 2) |
| A-11 | H$_3$C-C(CH$_3$)(CH$_3$) | H | H | 2) | 2) |
| A-12 | phenyl | H | H | 2) | 2) |
| A-13 | adamantyl | H | H | 2) | 2) |

1) $R^{5"}$ and $R^{6"}$ together form a ring

2) $R^{3"}$ and $R^{4"}$ together form a ring

Examples of preferred catalysts include the following compounds:
palladium(II) acetylacetonate, palladium(0) dibenzylideneacetone complexes, palladium(II) propionate,
Pd$_2$(dba)$_3$: [tris(dibenzylideneacetone)dipalladium(0)],
Pd(dba)$_2$: [bis(dibenzylideneacetone) palladium(0)],
Pd(PR$_3$)$_2$, wherein PR$_3$ is a trisubstituted phosphine of formula VI, Pd(OAc)$_2$: [palladium(II) acetate], palladium(II) chloride, palladium(II) bromide, lithium tetrachloropalladate(II), PdCl$_2$(PR$_3$)$_2$; wherein PR$_3$ is a trisubstituted phosphine of formula VI; palladium(0) diallyl ether complexes, palladium (II) nitrate, PdCl$_2$(PhCN)$_2$: [dichlorobis(benzonitrile) palladium(II)], PdCl$_2$(CH$_3$CN): [dichlorobis(acetonitrile) palladium(II)], and PdCl$_2$(COD): [dichloro(1,5-cyclooctadiene) palladium(II)].

Especially preferred are PdCl$_2$, Pd$_2$(dba)$_3$, Pd(dba)$_2$, Pd(OAc)$_2$, or Pd(PR$_3$)$_2$. Most preferred are Pd$_2$(dba)$_3$ and Pd(OAc)$_2$.

The palladium catalyst is present in the reaction mixture in catalytic amounts. The term "catalytic amount" refers to an amount that is clearly below one equivalent of the (hetero) aromatic compound(s), preferably 0.001 to 5 mol-%, most preferably 0.001 to 1 mol-%, based on the equivalents of the (hetero)aromatic compound(s) used.

The amount of phosphines or phosphonium salts in the reaction mixture is preferably from 0.001 to 10 mol-%, most preferably 0.01 to 5 mol-%, based on the equivalents of the (hetero)aromatic compound(s) used. The preferred ratio of Pd:phosphine is 1:4.

The base can be selected from all aqueous and nonaqueous bases and can be inorganic, or organic. It is preferable that at least 1.5 equivalents of said base per functional boron group is present in the reaction mixture. Suitable bases are, for example, alkali and alkaline earth metal hydroxides, carboxylates, carbonates, fluorides and phosphates such as sodium and potassium hydroxide, acetate, carbonate, fluoride and phosphate or also metal alcoholates. It is also possible to use a mixture of bases. The base is preferably a lithium salt, such as, for example, lithium alkoxides (such as, for example, lithium methoxide and lithium ethoxide), lithium hydroxide, carboxylate, carbonate, fluoride and/or phosphate.

The at present most preferred base is aqueous LiOHxH$_2$O (monohydrate of LiOH) and (waterfree) LiOH.

The reaction is typically conducted at about 0° C. to 180° C., preferably from 20 to 160° C., more preferably from 40 to 140° C. and most preferably from 40 to 120° C. A polymerization reaction may take 0.1, especially 0.2 to 100 hours.

In a preferred embodiment of the present invention the solvent is THF, the base is LiOH*H$_2$O and the reaction is conducted at reflux temperature of THF (about 65° C.).

The solvent is for example selected from toluene, xylenes, anisole, THF, 2-methyltetrahydrofuran, dioxane, chlorobenzene, fluorobenzene or solvent mixtures comprising one or more solvents like e.g. THF/toluene and optionally water. Most preferred is THF, or THF/water.

Advantageously, the polymerisation is carried out in presence of a) palladium(II) acetate, or Pd$_2$(dba)$_3$, (tris(dibenzylideneacetone)dipalladium(0)) and an organic phosphine A-1 to A-13, b) LiOH, or LiOHxH$_2$O; and c) THF, and optionally water. If the monohydrate of LiOH is used, no water needs to be added.

Most preferred the polymerisation is carried out in presence of a) palladium(II) acetate, or Pd$_2$(dba)$_3$ (tris(dibenzylideneacetone)dipalladium(0)) and

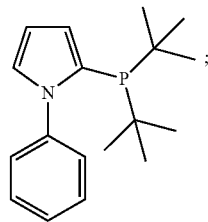 [SMILES: CC(C)(C)P(c1cccn1-c1ccccc1)C(C)(C)C]

b) LiOHxH$_2$O; and c) THF. The palladium catalyst is present in an amount of preferably about 0.5 mol-%, based on the equivalents of the (hetero)aromatic compound(s) used. The amount of phosphines or phosphonium salts in the reaction mixture is preferably about 2 mol-%, based on the equivalents of the (hetero) aromatic compound(s) used. The preferred ratio of Pd:phosphine is about 1:4.

Preferably the polymerization reaction is conducted under inert conditions in the absence of oxygen. Nitrogen and more preferably argon are used as inert gases.

The process described in WO2010/136352 is suitable for large-scale applications, is readily accessible and convert starting materials to the respective polymers in high yield, with high purity and high selectivity. The process can provide polymers having weight average molecular weights of at least 10,000, more preferably at least 20,000, most preferably at least 30,000. The at present most preferred polymers have a weight average molecular weight of 30,000 to 80,000 Daltons. Molecular weights are determined according to high-temperature gel permeation chromatography (HT-GPC) using polystyrene standards. The polymers preferably have a polydispersibility of 1.01 to 10, more preferably 1.1 to 3.0, most preferred 1.5 to 2.5.

If desired, a monofunctional aryl halide or aryl boronate, such as, for example,

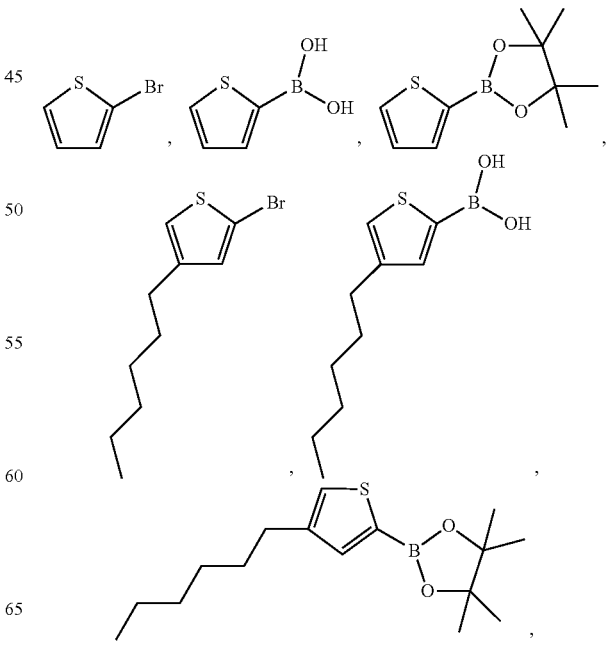

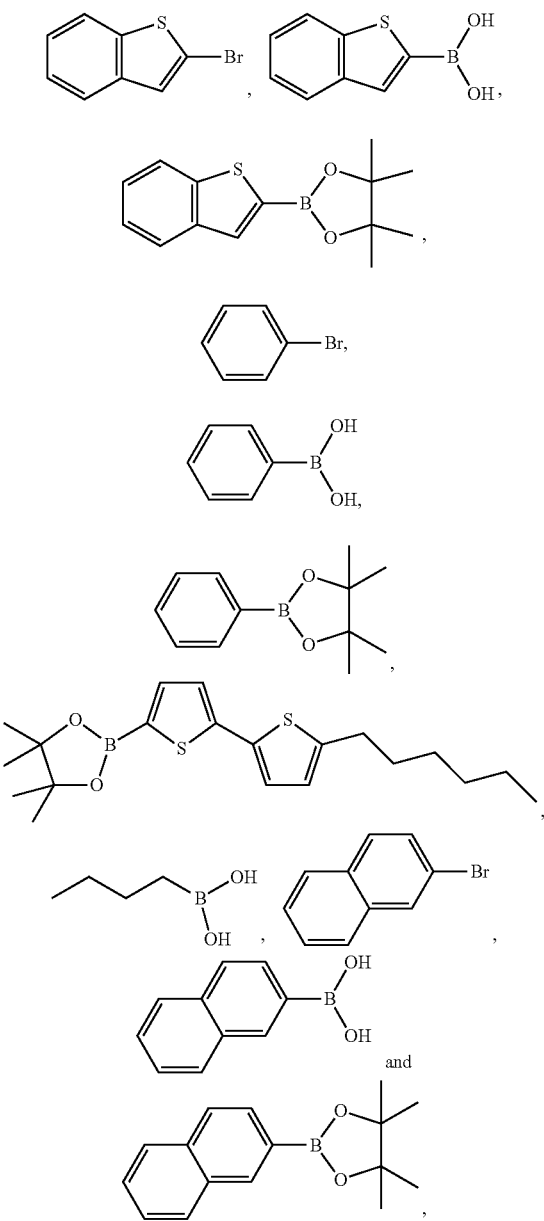

may be used as a chain-terminator in such reactions, which will result in the formation of a terminal aryl group.

It is possible to control the sequencing of the monomeric units in the resulting copolymer by controlling the order and composition of monomer feeds in the Suzuki reaction.

The polymers of the present invention can also be synthesized by the Stille coupling (see, for example, Babudn et al, J. Mater. Chem., 2004, 14, 11-34; J. K. Stille, Angew. Chemie Int. Ed. Engl. 1986, 25, 508). To prepare polymers corresponding to formula VII a dihalogenide of formula $X^{10}$-A-$X^{10}$ is reacted with a compound of formula $X^{11'}$—$COM^1$-$X^{11'}$, or a dihalogenide of formula $X^{10}$—$COM^1$-$X^{10}$ is reacted with a compound of formula $X^{11'}$-A-$X^{11'}$, wherein $X^{11'}$ is a group —$SnR^{207}R^{208}R^{209}$ and $X^{10}$ is as defined above, in an inert solvent at a temperature in range from 0° C. to 200° C. in the presence of a palladium-containing catalyst, wherein $R^{207}$, $R^{208}$ and $R^{209}$ are identical or different and are H or $C_1$-$C_6$alkyl, wherein two groups optionally form a common ring and these radicals are branched or unbranched. It must be ensured here that the totality of all monomers used has a highly balanced ratio of organotin functions to halogen functions. In addition, it may prove advantageous to remove any excess reactive groups at the end of the reaction by end-capping with monofunctional reagents. In order to carry out the process, the tin compounds and the halogen compounds are preferably introduced into one or more inert organic solvents and stirred at a temperature of from 0 to 200° C., preferably from 30 to 170° C. for a period of from 1 hour to 200 hours, preferably from 5 hours to 150 hours. The crude product can be purified by methods known to the person skilled in the art and appropriate for the respective polymer, for example repeated re-precipitation or even by dialysis.

Suitable organic solvents for the process described are, for example, ethers, for example diethyl ether, dimethoxyethane, diethylene glycol dimethyl ether, tetrahydrofuran, dioxane, dioxolane, diisopropyl ether and tert-butyl methyl ether, hydrocarbons, for example hexane, isohexane, heptane, cyclohexane, benzene, toluene and xylene, alcohols, for example methanol, ethanol, 1-propanol, 2-propanol, ethylene glycol, 1-butanol, 2-butanol and tertbutanol, ketones, for example acetone, ethyl methyl ketone and isobutyl methyl ketone, amides, for example dimethylformamide (DMF), dimethylacetamide and N-methylpyrrolidone, nitriles, for example acetonitrile, propionitrile and butyronitrile, and mixtures thereof.

The palladium and phosphine components should be selected analogously to the description for the Suzuki variant.

The Stille coupling reaction is preferred over the Suzuki coupling reaction, if the silyl groups $E^{Si}$ or $D^{Si}$ might hydrolyze under the Suzuki reaction conditions.

Alternatively, the polymers of the present invention can also be synthesized by the Negishi reaction using a zinc reagent A-$(ZnX^{12})_2$, wherein $X^{12}$ is halogen and halides, and $COM^1$-$(X^{23})_2$, wherein $X^{23}$ is halogen or triflate, or using A-$(X^{23})_2$ and $COM^1$-$(ZnX^{12})_2$. Reference is, for example, made to E. Negishi et al., Heterocycles 18 (1982) 117-22.

Alternatively, the polymers of the present invention can also be synthesized by the Hiyama reaction using a organo-silicon reagent A-$(SiR^{210}R^{211}R^{212})_2$, wherein $R^{210}$, $R^{211}$ and $R^{212}$ are identical or different and are halogen, or $C_1$-$C_6$alkyl, and $COM^1$-$(X^{23})_2$, wherein $X^{23}$ is halogen or triflate, or using A-$(X^{23})_2$ and $COM^1$-$(SiR^{210}R^{211}R^{212})_2$. Reference is, for example, made to T. Hiyama et al., Pure Appl. Chem. 66 (1994) 1471-1478 and T. Hiyama et al., Synlett (1991) 845-853.

Homopolymers of the type $(A)_n$ can be obtained via Yamamoto coupling of dihalides $X^{10}$-A-$X^{10}$, where $X^{10}$ is halogen, preferably bromide. Alternatively homopolymers of the type $(A)_n$ can be obtained via oxidative polymerization of units $X^{10}A$-$X^{10}$, where $X^{10}$ is hydrogen, e.g. with $FeCl_3$ as oxidizing agent.

In case of $R^1$ and $R^2$ $C_1$-$C_{25}$alkyl-$SiR^{161}R^{162}R^{163}$ groups may be obtained by first alkylating the nitrogen atoms of the DPP with a $C_2$-$C_{25}$iodoalkenyl group and then the addition of an H—Si bond across a double bond by hydrosilation. Advantageously, platinum(II) compounds such as Karstedt catalyst, platinum chloride olefin complex and [$PtCl_2$(cyclooctadiene)] are used as catalyst. Karstedt catalyst is a compound of platinum(0) and divinyltetramethyldisiloxane.

The compounds of the formula

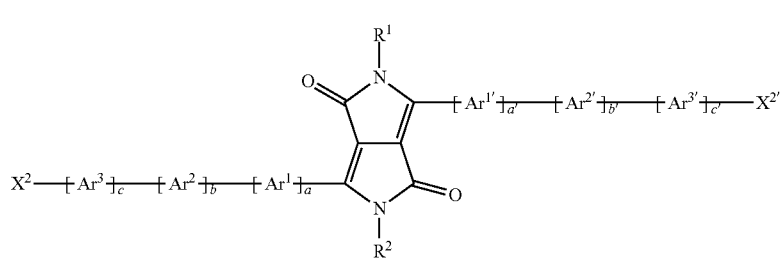

(V)

are intermediates in the production of the polymers of the present invention, are new and form a further subject of the present invention. $R^1$, $R^2$, a, a', b, b', c, c', $Ar^1$, $Ar^{1'}$, $Ar^2$, $Ar^{2'}$, $Ar^3$ and $Ar^{3'}$ are as defined above, and $X^2$ and $X^{2'}$ are independently of each other halogen, $ZnX^{12}$, —$SnR^{207}R^{208}R^{209}$, wherein $R^{207}$, $R^{208}$ and $R^{209}$ are identical or different and are H or $C_1$-$C_6$alkyl, wherein two groups optionally form a common ring and these groups are branched or unbranched and $X^{12}$ is a halogen atom; or —$OS(O)_2CF_3$, —$OS(O)_2$-aryl, —$OS(O)_2CH_3$, —$B(OH)_2$, —$B(OY^1)_2$,

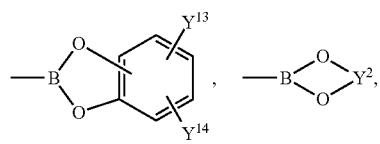

—$BF_4Na$, or —$BF_4K$, wherein $Y^1$ is independently in each occurrence a $C_1$-$C_{10}$alkyl group and $Y^2$ is independently in each occurrence a $C_2$-$C_{10}$alkylene group, such as —$CY^3Y^4$—$CY^5Y^6$—, or —$CY^7Y^8$—$CY^9Y^{10}$—$CY^{11}Y^{12}$—, wherein $Y^3$, $Y^4$, $Y^5$, $Y^6$, $Y^7$, $Y^8$, $Y^9$, $Y^{10}$, $Y^{11}$ and $Y^{12}$ are independently of each other hydrogen, or a $C_1$-$C_{10}$alkyl group, and $Y^{13}$ and $Y^{14}$ are independently of each other hydrogen, or a $C_1$-$C_{10}$alkyl group. $X^2$ and $X^{2'}$ are preferably the same. With respect to the substituents $R^1$, $R^2$, a, a', b, b', c, c', $Ar^1$, $Ar^{1'}$, $Ar^2$, $Ar^{2'}$, $Ar^3$ and $Ar^{3'}$ the same preferences apply as for the compounds of formula I.

Examples of compounds of formula V are shown below:

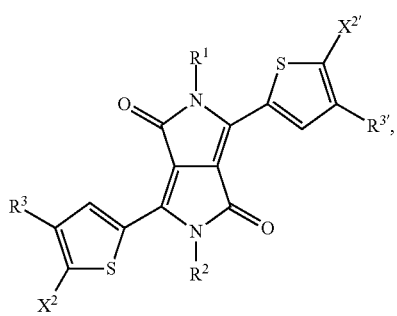

(Va)

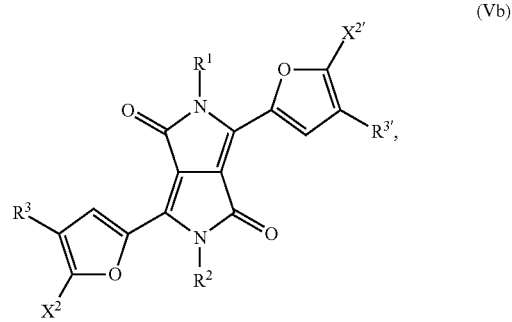

(Vb)

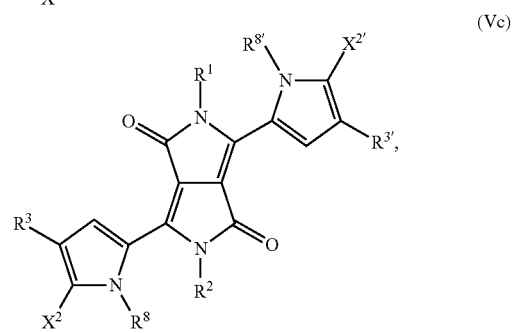

(Vc)

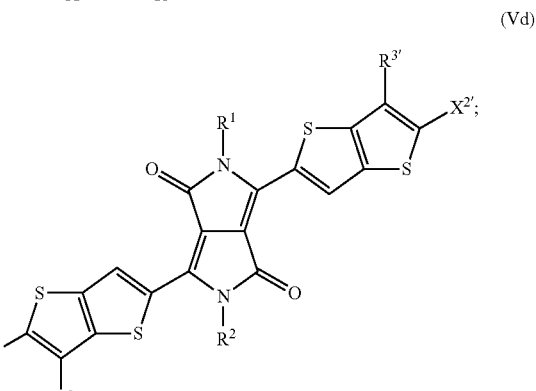

(Vd)

wherein $X^2$ is as defined above.

$R^1$ and $R^2$ may be the same or different and are preferably selected from $C_1$-$C_8$alkyl which is substituted with $E^{Si}$.

$R^3$ and $R^{3'}$ are independently of each other hydrogen or $C_1$-$C_{25}$alkyl.

$R^8$ and $R^{8'}$ are independently of each other hydrogen or $C_1$-$C_{25}$alkyl, especially $C_1$-$C_{25}$alkyl.

Among the compounds of formula V the following compounds are preferred:

(I-1)
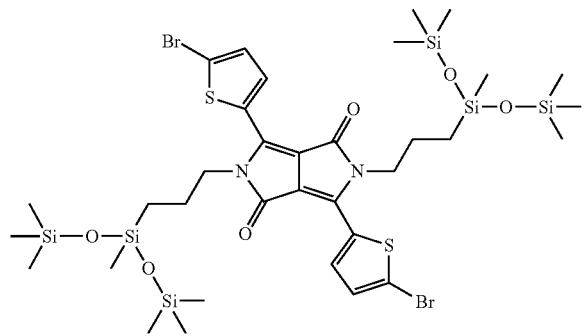
(I-2)
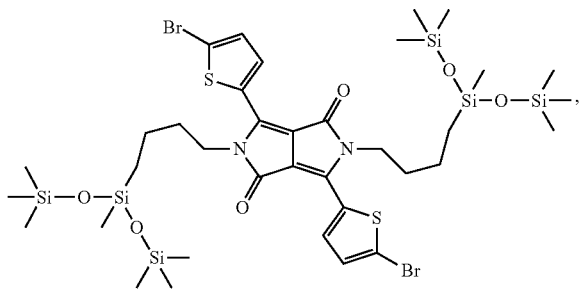
(I-3)
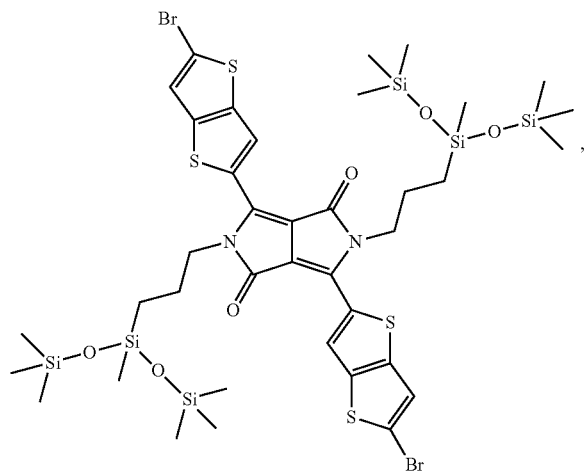
(I-4)
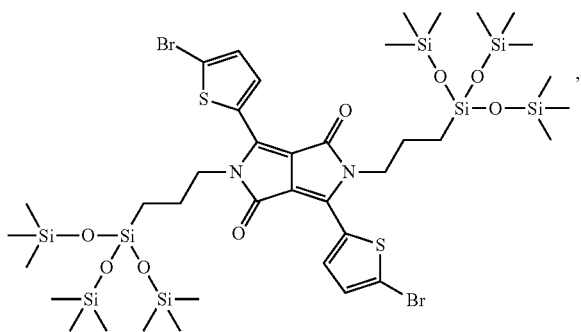
(I-5)
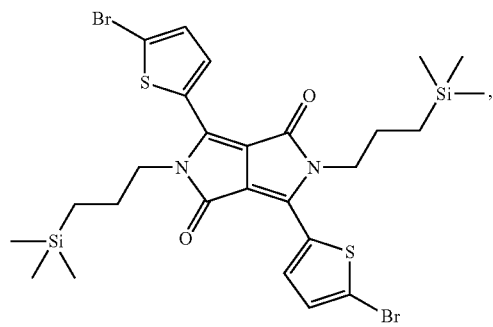
(I-6)
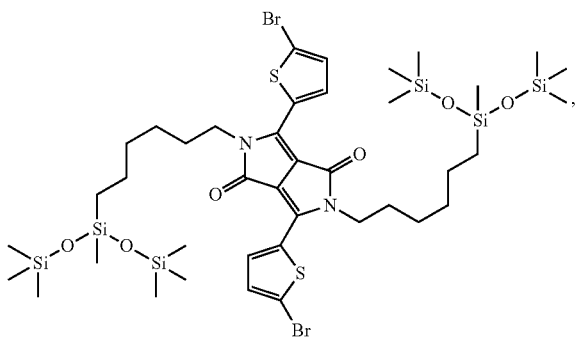
(I-7)
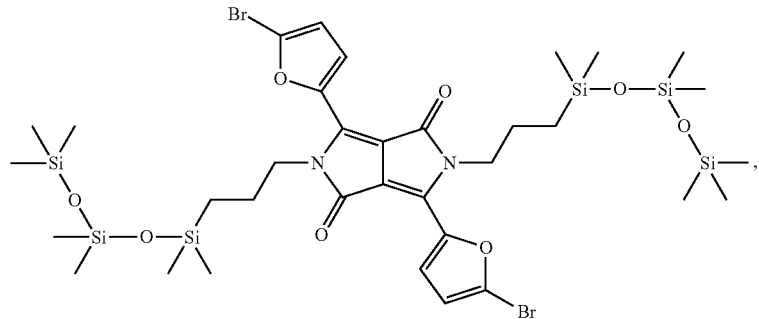

(I-8)
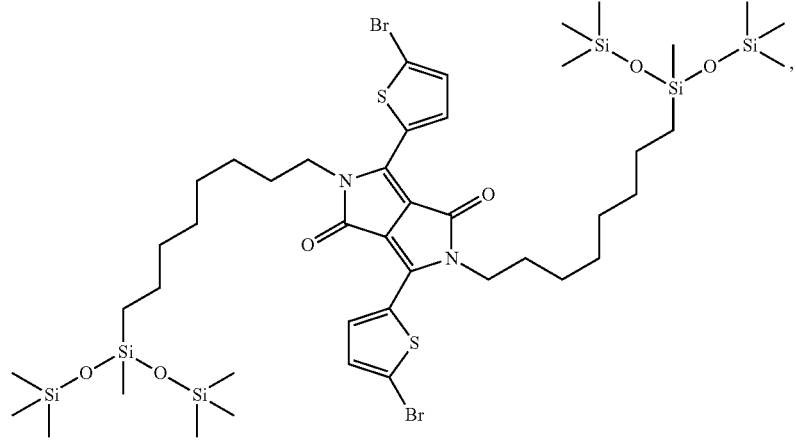
(I-9)
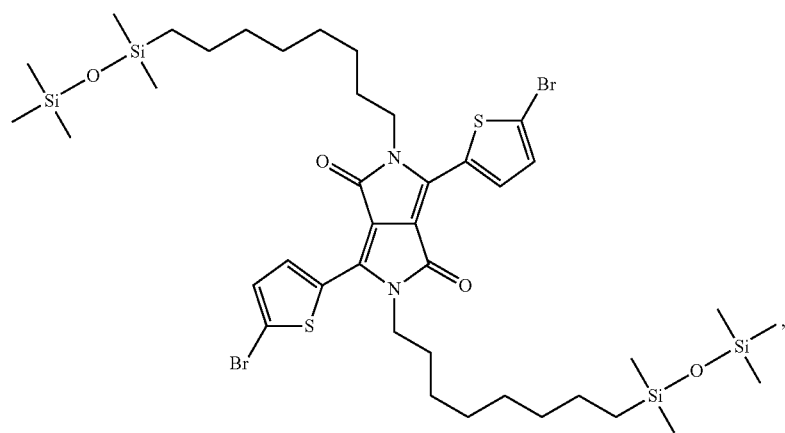
(I-10) (I-11)
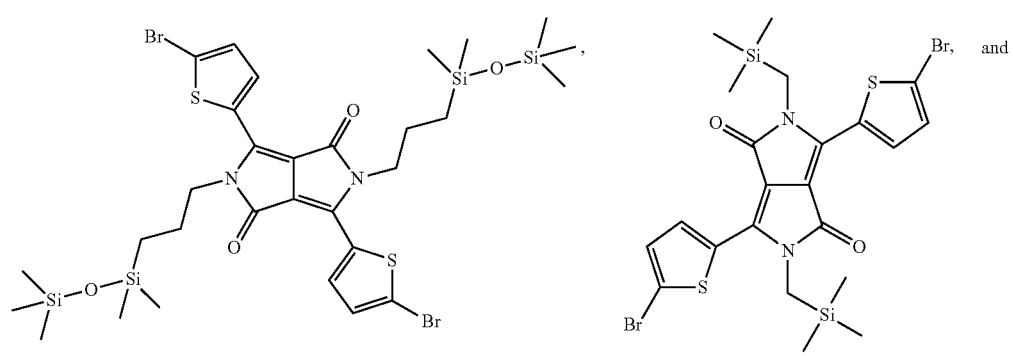

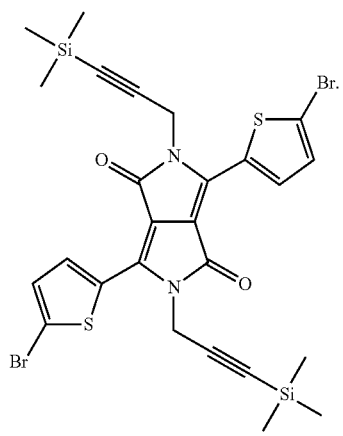

(I-12)

Halogen is fluorine, chlorine, bromine and iodine.

$C_1$-$C_{100}$alkyl is preferably $C_1$-$C_{38}$alkyl, especially $C_1$-$C_{25}$alkyl. $C_1$-$C_{25}$alkyl ($C_1$-$C_{18}$alkyl) is typically linear or branched, where possible. Examples are methyl, ethyl, n-propyl, isopropyl, n-butyl, sec.-butyl, isobutyl, tert.-butyl, n-pentyl, 2-pentyl, 3-pentyl, 2,2-dimethylpropyl, 1,1,3,3-tetramethylpentyl, n-hexyl, 1-methylhexyl, 1,1,3,3,5,5-hexamethylhexyl, n-heptyl, isoheptyl, 1,1,3,3-tetramethylbutyl, 1-methylheptyl, 3-methylheptyl, n-octyl, 1,1,3,3-tetramethylbutyl and 2-ethylhexyl, n-nonyl, decyl, undecyl, dodecyl, tridecyl, tetradecyl, pentadecyl, hexadecyl, heptadecyl, octadecyl, eicosyl, heneicosyl, docosyl, tetracosyl or pentacosyl. $C_1$-$C_8$alkyl is typically methyl, ethyl, n-propyl, isopropyl, n-butyl, sec.-butyl, isobutyl, tert.-butyl, n-pentyl, 2-pentyl, 3-pentyl, 2,2-dimethyl-propyl, n-hexyl, n-heptyl, n-octyl, 1,1,3,3-tetramethylbutyl and 2-ethylhexyl. $C_1$-$C_4$alkyl is typically methyl, ethyl, n-propyl, isopropyl, n-butyl, sec.-butyl, isobutyl, tert.-butyl.

$C_2$-$C_{100}$alkenyl is preferably $C_2$-$C_2$alkenyl. $C_2$-$C_2$alkenyl ($C_2$-$C_{18}$alkenyl) groups are straight-chain or branched alkenyl groups, such as e.g. vinyl, allyl, methallyl, isopropenyl, 2-butenyl, 3-butenyl, isobutenyl, n-penta-2,4-dienyl, 3-methyl-but-2-enyl, n-oct-2-enyl, n-dodec-2-enyl, isododecenyl, n-dodec-2-enyl or n-octadec-4-enyl.

$C_3$-$C_{100}$alkinyl is preferably $C_2$-$C_{25}$alkinyl. $C_{2-25}$alkinyl ($C_{2-18}$alkinyl) is straight-chain or branched and preferably $C_{2-8}$-alkynyl, which may be unsubstituted or substituted, such as, for example, ethynyl, 1-propyn-3-yl, 1-butyn-4-yl, 1-pentyn-5-yl, 2-methyl-3-butyn-2-yl, 1,4-pentadiyn-3-yl, 1,3-pentadiyn-5-yl, 1-hexyn-6-yl, cis-3-methyl-2-penten-4-yn-1-yl, trans-3-methyl-2-penten-4-yn-1-yl, 1,3-hexadiyn-5-yl, 1-octyn-8-yl, 1-nonyn-9-yl, 1-decyn-10-yl, or 1-tetracosyn-24-yl.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

An aliphatic hydrocarbon group having up to 25 carbon atoms is a linear or branched alkyl, alkenyl or alkynyl (also spelled alkinyl) group having up to 25 carbon atoms as exemplified above.

Alkylene is bivalent alkyl, i.e. alkyl having two (instead of one) free valencies, e.g. trimethylene or tetramethylene.

Alkenylene is bivalent alkenyl, i.e. alkenyl having two (instead of one) free valencies, e.g. —$CH_2$—CH=CH—$CH_2$—.

Aliphatic groups can, in contrast to aliphatic hydrocarbon groups, be substituted by any acyclic substituents, but are preferably unsubstituted. Preferred substituents are $C_1$-$C_8$alkoxy or $C_1$-$C_8$alkylthio groups as exemplified further below. The term "aliphatic group" comprises also alkyl groups wherein certain non-adjacent carbon atoms are replaced by oxygen, like —$CH_2$—O—$CH_2$—$CH_2$—O—$CH_3$. The latter group can be regarded as methyl substituted by —O—$CH_2$—$CH_2$—O—$CH_3$.

A cycloaliphatic hydrocarbon group is a cycloalkyl or cycloalkenyl group which may be substituted by one or more aliphatic and/or cycloaliphatic hydrocarbon groups.

A cycloaliphatic-aliphatic group is an aliphatic group substituted by a cycloaliphatic group, wherein the terms "cycloaliphatic" and "aliphatic" have the meanings given herein and wherein the free valency extends from the aliphatic moiety. Hence, a cycloaliphaticaliphatic group is for example a cycloalkyl-alkyl group.

A "cycloalkenyl group" means an unsaturated alicyclic hydrocarbon group containing one or more double bonds, such as cyclopentenyl, cyclopentadienyl, cyclohexenyl and the like, which may be unsubstituted or substituted by one or more aliphatic and/or cycloaliphatic hydrocarbon groups and/or condensed with phenyl groups.

A bivalent group of the formula IVb wherein $R^{28}$ and $R^{27}$ together represent alkylene or alkenylene which may be both bonded via oxygen and/or sulfur to the thienyl residue and which may both have up to 25 carbon atoms, is e.g. a group of the formula

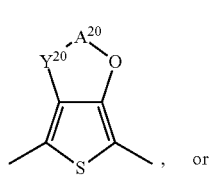

(XXIX)

, or

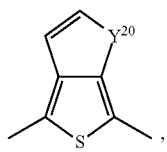

(XXX)

wherein A²⁰ represents linear or branched alkylene having up to 25 carbon atoms, preferably ethylene or propylene which may be substituted by one or more alkyl groups, and Y²⁰ represents oxygen or sulphur. For example, the bivalent group of the formula —Y²⁰-A²⁰-O— represents —O—CH₂—CH₂—O— or —O—CH₂—CH₂—CH₂—O—.

A group of the formula IVa wherein two groups R²² to R²⁶ which are in the neighborhood of each other, together represent alkylene or alkenylene having up to 8 carbon atoms, thereby forming a ring, is e.g. a group of the formula

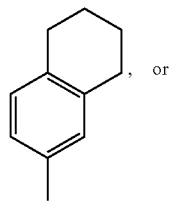

(XXXII)

or

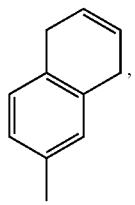

(XXXIII)

wherein in the group of the formula XXXII R²³ and R²⁴ together represent 1,4-butylene and in the group of the formula XXXIII R²³ and R²⁴ together represent 1,4-but-2-enylene.

C₁-C₂₅alkoxy groups (C₁-C₁₈alkoxy groups) are straight-chain or branched alkoxy groups, e.g. methoxy, ethoxy, n-propoxy, isopropoxy, n-butoxy, sec-butoxy, tert-butoxy, amyloxy, isoamyloxy or tert-amyloxy, heptyloxy, octyloxy, isooctyloxy, nonyloxy, decyloxy, undecyloxy, dodecyloxy, tetradecyloxy, pentadecyloxy, hexadecyloxy, heptadecyloxy and octadecyloxy. Examples of C₁-C₈alkoxy are methoxy, ethoxy, n-propoxy, isopropoxy, n-butoxy, sec.-butoxy, isobutoxy, tert.-butoxy, n-pentoxy, 2-pentoxy, 3-pentoxy, 2,2-dimethylpropoxy, n-hexoxy, n-heptoxy, n-octoxy, 1,1,3,3-tetramethylbutoxy and 2-ethylhexoxy, preferably C₁-C₄alkoxy such as typically methoxy, ethoxy, n-propoxy, isopropoxy, n-butoxy, sec.-butoxy, isobutoxy, tert.-butoxy. The term "alkylthio group" means the same groups as the alkoxy groups, except that the oxygen atom of the ether linkage is replaced by a sulfur atom.

C₁-C₁₈perfluoroalkyl, especially C₁-C₄perfluoroalkyl, is a branched or unbranched radical such as for example —CF₃, —CF₂CF₃, —CF₂CF₂CF₃, —CF(CF₃)₂, —(CF₂)₃CF₃, and —C(CF₃)₃.

C₁-C₂₅haloalkyl means a C₁-C₂₅alkyl group which is substituted with one or more halogen atoms.

The term "carbamoyl group" is typically a C₁₋₁₈carbamoyl radical, preferably C₁₋₈carbamoyl radical, which may be unsubstituted or substituted, such as, for example, carbamoyl, methylcarbamoyl, ethylcarbamoyl, n-butylcarbamoyl, tert-butylcarbamoyl, dimethylcarbamoyloxy, morpholinocarbamoyl or pyrrolidinocarbamoyl.

A cycloalkyl group is typically C₃-C₁₂cycloalkyl, such as, for example, cyclopentyl, cyclohexyl, cycloheptyl, cyclooctyl, cyclononyl, cyclodecyl, cycloundecyl, cyclododecyl, preferably cyclopentyl, cyclohexyl, cycloheptyl, or cyclooctyl, which may be unsubstituted or substituted. The cycloalkyl group, in particular a cyclohexyl group, can be condensed one or two times by phenyl which can be substituted one to three times with C₁-C₄-alkyl, halogen and cyano. Examples of such condensed cyclohexyl groups are:

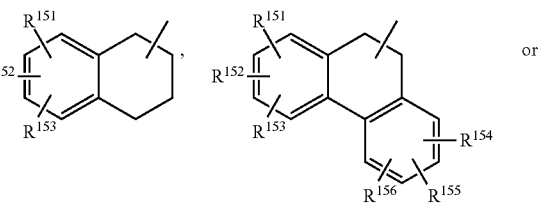

in particular

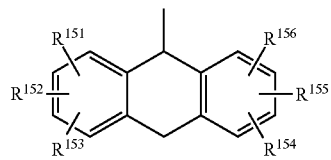

wherein R¹⁵¹, R¹⁵², R¹⁵³, R¹⁵⁴, R¹⁵⁵ and R¹⁵⁶ are independently of each other C₁-C₈-alkyl, C₁-C₈-alkoxy, halogen and cyano, in particular hydrogen.

A cycloalkyl-alkyl group is an alkyl group substituted by a cycloalkyl group, e.g. cyclohexyl-methyl.

C₆-C₂₄aryl (C₆-C₁₈aryl) is typically phenyl, indenyl, azulenyl, naphthyl, biphenyl, asindacenyl, s-indacenyl, acenaphthylenyl, fluorenyl, phenanthryl, fluoranthenyl, triphenlenyl, chrysenyl, naphthacen, picenyl, perylenyl, pentaphenyl, hexacenyl, pyrenyl, or anthracenyl, preferably phenyl, 1-naphthyl, 2-naphthyl, 4-biphenyl, 9-phenanthryl, 2- or 9-fluorenyl, 3- or 4-biphenyl, which may be unsubstituted or substituted. Examples of C₆-C₁₂aryl are phenyl, 1-naphthyl, 2-naphthyl, 3- or 4-biphenyl, 2- or 9-fluorenyl or 9-phenanthryl, which may be unsubstituted or substituted.

C₇-C₂₅aralkyl is typically benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl, ω-phenyl-octadecyl, ω-phenyl-eicosyl or ω-phenyl-docosyl, preferably C₇-C₁₈aralkyl such as benzyl, 2-benzyl-2-propyl, β-phenyl-ethyl, α,α-dimethylbenzyl, ω-phenyl-butyl, ω,ω-dimethyl-ω-phenyl-butyl, ω-phenyl-dodecyl or ω-phenyl-octadecyl, and particularly preferred C₇-C₁₂aralkyl such as benzyl, 2-benzyl-2-propyl, β-phenyl-ethyl, α,α-dimethylbenzyl, ω-phenyl-butyl, or ω,ω-dimethyl-ω-phenyl-butyl, in which both the aliphatic hydrocarbon group and aromatic hydrocarbon group may be unsubstituted or substituted. Preferred examples are benzyl, 2-phenylethyl, 3-phenylpropyl, naphthylethyl, naphthylmethyl, and cumyl.

Heteroaryl is typically C₂-C₂₀heteroaryl, i.e. a ring with five to seven ring atoms or a condensed ring system, wherein nitrogen, oxygen or sulfur are the possible hetero atoms, and is typically an unsaturated heterocyclic group with five to 30 atoms having at least six conjugated π-electrons such as thienyl, benzo[b]thienyl, dibenzo[b,d]thienyl, thianthrenyl, furyl, furfuryl, 2H-pyranyl, benzofuranyl, isobenzofuranyl, dibenzofuranyl, phenoxythienyl, pyrrolyl, imidazolyl, pyrazolyl, pyridyl, bipyridyl, triazinyl, pyrimidinyl, pyrazinyl, pyridazinyl, indolizinyl, isoindolyl, indolyl, indazolyl, purinyl, quinolizinyl, chinolyl, isochinolyl, phthalazinyl, naphthyridinyl, chinoxalinyl, chinazolinyl, cinnolinyl, pteridinyl, carbazolyl, carbolinyl, benzotriazolyl, benzoxazolyl, phenanthridinyl, acridinyl, pyrimidinyl, phenanthrolinyl, phenazinyl, isothiazolyl, phenothiazinyl, isoxazolyl, furazanyl or phenoxazinyl, which can be unsubstituted or substituted.

C₆-C₂₄arylen groups, which optionally can be substituted, are typically phenylene, 4-methylphenylene, 4-methoxyphenylene, naphthylene, especially 1-naphthylene, or 2-naphthylene and biphenylylene.

Preferred C₂-C₂₀heteroarylen groups are pyridylene, triazinylene, pyrimidinylene, carbazolylene, dibenzofuranylene which optionally can be substituted.

Examples of C₃-C₁₂ cycloalkylene are cyclopropylene, cyclopentylene, cyclohexylene. Possible substituents of the above-mentioned groups are C₁-C₈alkyl, a hydroxyl group, a mercapto group, C₁-C₈alkoxy, C₁-C₈alkylthio, halogen, halo-C₁-C₈alkyl, a cyano group, a carbamoyl group, a nitro group or a silyl group, especially C₁-C₈alkyl, C₁-C₈alkoxy, C₁-C₈alkylthio, halogen, halo-C₁-C₈alkyl, or a cyano group.

C₁-C₁₈alkyl interrupted by one or more O is, for example, (CH₂CH₂O)₁₋₉R$^x$, where R$^x$ is H or C₁-C₁₀alkyl, CH₂—CH(OR$^{y'}$)—CH₂—O—R$^y$, where R$^{y'}$ is C₁-C₁₈alkyl, and R$^{y'}$ embraces the same definitions as R$^y$ or is H.

If a substituent, such as, for example R³, occurs more than one time in a group, it can be different in each occurrence.

A mixture containing a polymer of the present invention results in a semi-conducting layer comprising a polymer of the present invention (typically 5% to 99.9999% by weight, especially 20 to 85% by weight) and at least another material. The other material can be, but is not restricted to a fraction of the same polymer of the present invention with different molecular weight, another polymer of the present invention, a semi-conducting polymer, organic small molecules, carbon nanotubes, a fullerene derivative, inorganic particles (quantum dots, quantum rods, quantum tripods, TiO₂, ZnO etc.), conductive particles (Au, Ag etc.), insulator materials like the ones described for the gate dielectric (PET, PS etc.). The polymers of the present invention can be blended with compounds of formula III according to the present invention, or small molecules described, for example, in WO2009/047104, WO2010108873 (PCT/EP2010/053655), WO009/047104, U.S. Pat. No. 6,690,029, WO2007082584, and WO2008107089:

WO2007082584:

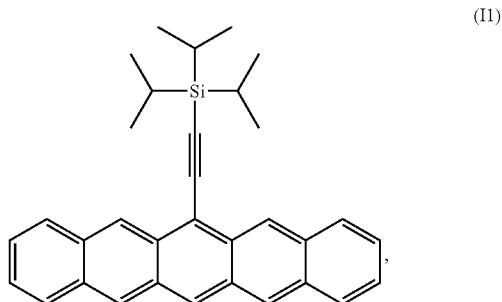

(I1)

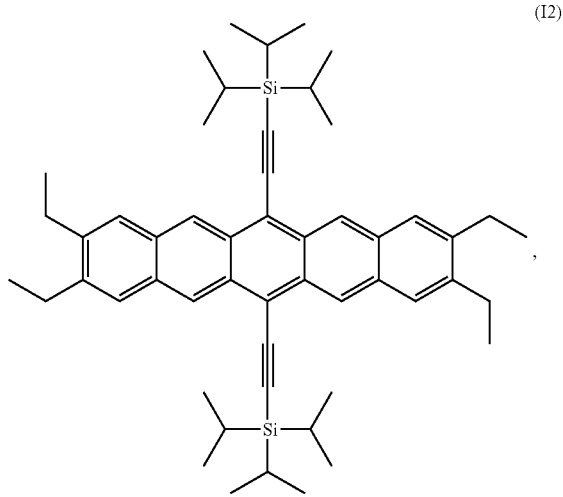

(I2)

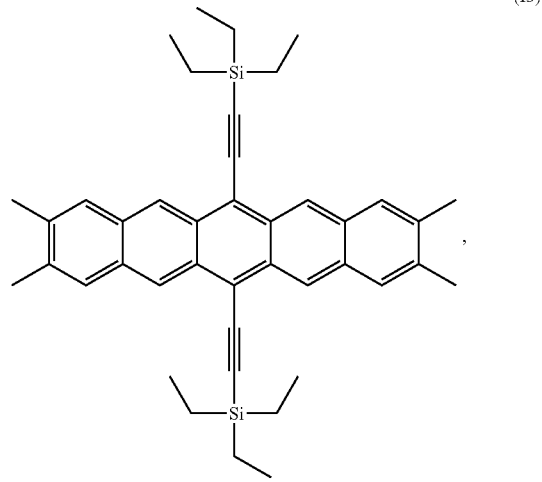

(I3)

(I4)
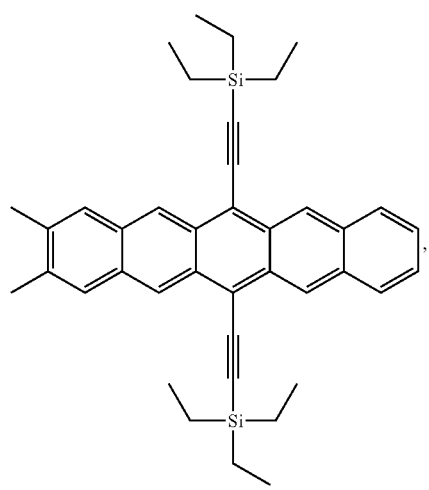
(I5)
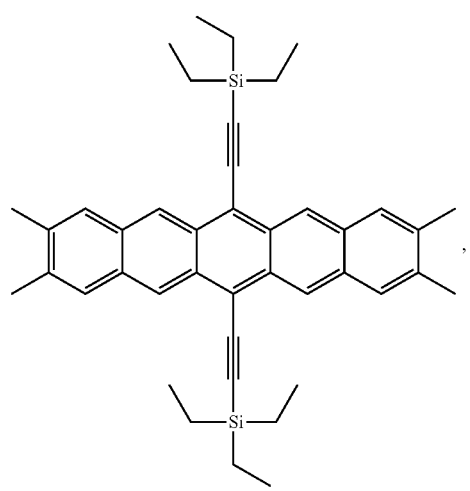
(I6)
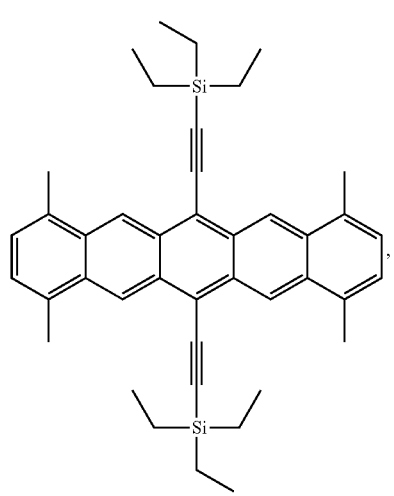
(I7)
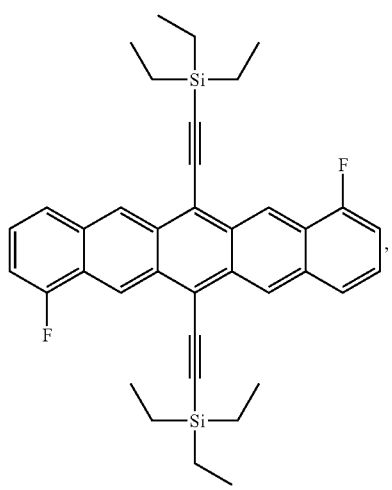
(I8)
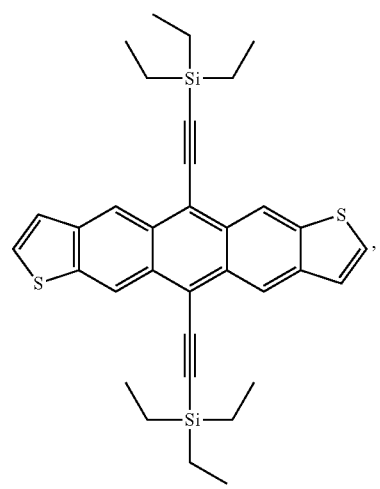
(I9)
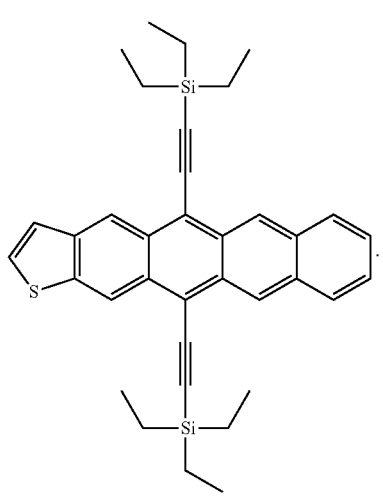

WO2008107089

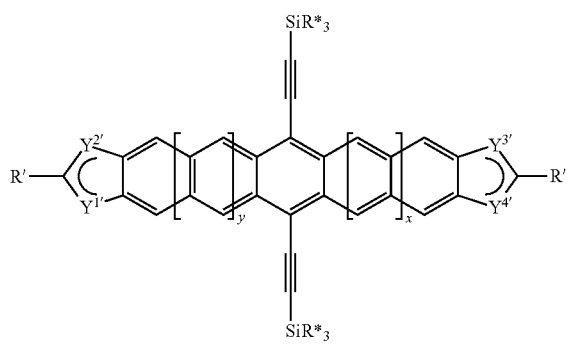

wherein one of $Y^{1'}$ and $Y^{2'}$ denotes —CH= or =CH— and the other denotes —X*—, one of $Y^{3'}$ and $Y^{4'}$ denotes —CH= or =CH— and the other denotes —X*—, X* is —O—, —S—, —Se— or —NR'''—, R* is cyclic, straight-chain or branched alkyl or alkoxy having 1 to 20 C-atoms, or aryl having 2-30 C-atoms, all of which are optionally fluorinated or perfluorinated, R' is H, F, Cl, Br, I, CN, straight-chain or branched alkyl or alkoxy having 1 to 20 C-atoms and optionally being fluorinated or perfluorinated, optionally fluorinated or perfluorinated aryl having 6 to 30 C-atoms, or $CO_2R''$, with R'' being H, optionally fluorinated alkyl having 1 to 20 C-atoms, or optionally fluorinated aryl having 2 to 30 C-atoms, R''' is H or cyclic, straight-chain or branched alkyl with 1 to 10 C-atoms, y is 0, or 1, x is 0, or 1

A1

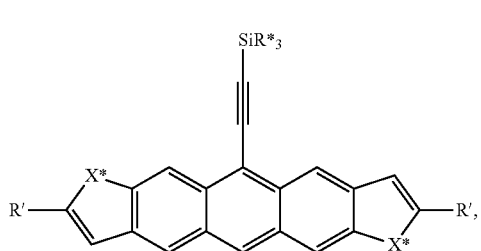

A2

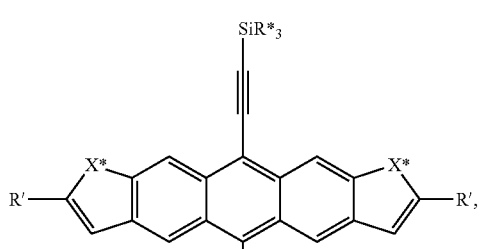

B1

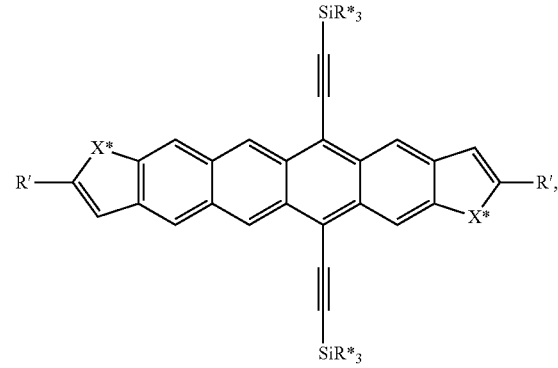

B2

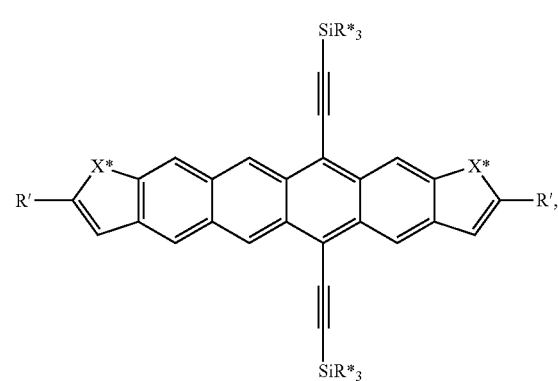

C1

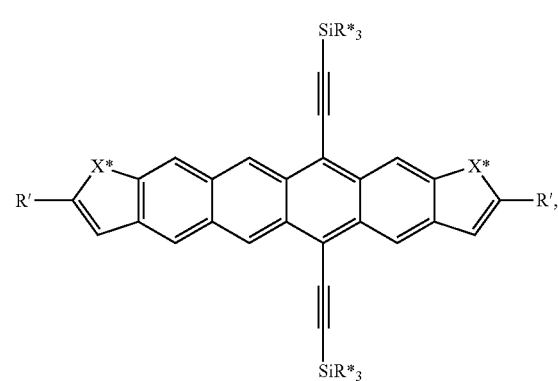

C2

The polymer can contain a small molecule, or a mixture of two, or more small molecule compounds.

Accordingly, the present invention also relates to an organic semiconductor material, layer or component, comprising a polymer according to the present invention.

The polymers of the invention can be used as the semiconductor layer in semiconductor devices. Accordingly, the present invention also relates to semiconductor devices, comprising a polymer of the present invention, or an organic semiconductor material, layer or component. The semiconductor device is especially an organic photovoltaic (PV) device (solar cell), a photodiode, or an organic field effect transistor.

The polymers of the invention can be used alone or in combination as the organic semiconductor layer of the semiconductor device. The layer can be provided by any useful means, such as, for example, vapor deposition (for materials with relatively low molecular weight) and printing techniques. The compounds of the invention may be sufficiently soluble in organic solvents and can be solution deposited and patterned (for example, by spin coating, dip coating, ink jet printing, gravure printing, flexo printing, offset printing, screen printing, microcontact (wave)-printing, drop or zone casting, or other known techniques).

The polymers of the invention can be used in integrated circuits comprising a plurality of OTFTs, as well as in various electronic articles. Such articles include, for example, radio-frequency identification (RFID) tags, backplanes for flexible displays (for use in, for example, personal computers, cell phones, or handheld devices), smart cards, memory devices, sensors (e.g. light-, image-, bio-, chemo-, mechanical- or temperature sensors), especially photodiodes, or security devices and the like.

A further aspect of the present invention is an organic semiconductor material, layer or component comprising one or more polymers of the present invention. A further aspect is the use of the polymers or materials of the present invention in an organic photovoltaic (PV) device (solar cell), a photodiode, or an organic field effect transistor (OFET). A further aspect is an organic photovoltaic (PV) device (solar cell), a photodiode, or an organic field effect transistor (OFET) comprising a polymer or material of the present invention.

The polymers of the present invention are typically used as organic semiconductors in form of thin organic layers or films, preferably less than 30 microns thick. Typically the semiconducting layer of the present invention is at most 1 micron (=1 μm) thick, although it may be thicker if required. For various electronic device applications, the thickness may also be less than about 1 micron thick. For example, for use in an OFET the layer thickness may typically be 100 nm or less. The exact thickness of the layer will depend, for example, upon the requirements of the electronic device in which the layer is used.

For example, the active semiconductor channel between the drain and source in an OFET may comprise a layer of the present invention.

An OFET device according to the present invention preferably comprises:
 a source electrode,
 a drain electrode,
 a gate electrode,
 a semiconducting layer,
 one or more gate insulator layers, and
 optionally a substrate, wherein the semiconductor layer comprises one or more polymers of the present invention.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a polymer of the present invention located on the second side of the insulator, and a drain electrode and a source electrode located on the polymer layer.

The OFET device can be a top gate device or a bottom gate device.

Suitable structures and manufacturing methods of an OFET device are known to the person skilled in the art and are described in the literature, for example in WO03/052841.

The gate insulator layer may comprise for example a fluoropolymer, like e.g. the commercially available Cytop 809M@, or Cytop 107M@(from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont), or Fluoropel® (from Cytonix) or the perfluorosolvent FC 43@(Acros, No. 12377).

The semiconducting layer comprising a polymer of the present invention may additionally comprise at least another material. The other material can be, but is not restricted to another polymer of the present invention, a semi-conducting polymer, a polymeric binder, organic small molecules different from a polymer of the present invention, carbon nanotubes, a fullerene derivative, inorganic particles (quantum dots, quantum rods, quantum tripods, $TiO_2$, ZnO etc.), conductive particles (Au, Ag etc.), and insulator materials like the ones described for the gate dielectric (PET, PS etc.). As stated above, the semiconductive layer can also be composed of a mixture of one or more polymers of the present invention and a polymeric binder. The ratio of the polymers of the present invention to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA). With this technique, a degradation of the electrical performance can be avoided (cf. WO2008/001123A1).

The polymers of the present invention are advantageously used in organic photovoltaic (PV) devices (solar cells). Accordingly, the invention provides PV devices comprising a polymer according to the present invention. A device of this construction will also have rectifying properties so may also be termed a photodiode. Photoresponsive devices have application as solar cells which generate electricity from light and as photodetectors which measure or detect light.

The PV device comprise in this order:
 (a) a cathode (electrode),
 (b) optionally a transition layer, such as an alkali halogenide, especially lithium fluoride,
 (c) a photoactive layer,
 (d) optionally a smoothing layer,
 (e) an anode (electrode),
 (f) a substrate.

The photoactive layer comprises the polymers of the present invention. Preferably, the photoactive layer is made of a conjugated polymer of the present invention, as an electron donor and an acceptor material, like a fullerene, particularly a functionalized fullerene PCBM, as an electron acceptor. As stated above, the photoactive layer may also contain a polymeric binder. The ratio of the polymers of formula I to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

For heterojunction solar cells the active layer comprises preferably a mixture of a polymer of the present invention and a fullerene, such as [60]PCBM (=6,6-phenyl-$C_{61}$-butyric acid methyl ester), or [70]PCBM, in a weight ratio of 1:1 to 1:3. The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of any semi-conducting polymer, such as, for example, a polymer of the present invention, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a polymer of the present invention as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyttetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called tandem solar cell' comprise in this order:
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the polymers of the present invention can also be used alone or together with other materials in or as alignment layers in LCD or OLED devices, as described for example in US2003/0021913.

It is another object of the present invention to provide compounds, which show high efficiency of energy conversion, excellent field-effect mobility, good on/off current ratios and/or excellent stability, when used in organic field effect transistors, organic photovoltaics (solar cells) and photodiodes.

In a further embodiment the present invention relates to compounds of the formula $A^1$-Y-$[A^3$-$Y^{15}]_o$-$[A^4$-$Y^{16}]_p$-$[A^5$-$Y^{17}]_q$$A^2$ (III), wherein Y, $Y^{15}$, $Y^{16}$ and $Y^{17}$ are independently of each other a group of formula o is 0, or 1, p is 0, or 1, q is 0, or 1;

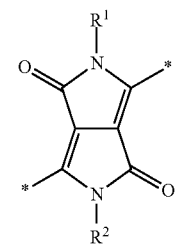

$A^1$ and $A^2$ are independently of each other a group of formula $[Ar^1]_a$-$[Ar^2]_b$-$[Ar^3]_c$-$R^{10}$, $A^3$, $A^4$ and $A^5$ are independently of each other a group of formula *-$[Ar^4]_k$-$[Ar^5]_l$-$[Ar^6]_r$-$[Ar^7]_z$* k is 0, 1, 2, or 3; l is 1, 2, or 3; r is 0, 1, 2, or 3; z is 0, 1, 2, or 3;

$R^{10}$ is hydrogen, halogen, cyano, $C_1$-$C_{25}$alkyl, $C_1$-$C_{25}$alkyl which is substituted one or more times by E and/or interrupted one or more times by D, $E^{Si}$, $C_1$-$C_{25}$alkyl which is substituted one or more times by $E^{Si}$ and/or interrupted one or more times by $D^{Si}$,

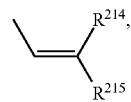

COO—$C_1$-$C_{18}$alkyl, $C_4$-$C_{18}$cycloalkyl group, $C_4$-$C_{18}$cycloalkyl group, which is substituted by G, $C_2$-$C_{18}$alkenyl, $C_2$-$C_{18}$alkynyl, $C_1$-$C_{18}$thioalkoxy, $C_1$-$C_{18}$alkoxy, $C_1$-$C_{18}$alkoxy which is substituted by E and/or interrupted by D, $C_7$-$C_{25}$aralkyl, $C_7$-$C_{25}$aralkyl, which is substituted by G, or a group of formulae Iva to Ivm,

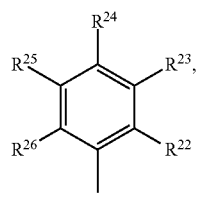 (IVa)
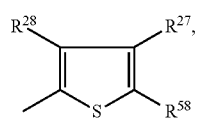 (IVb)
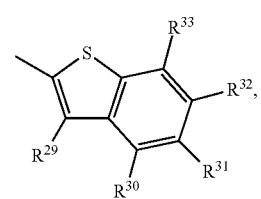 (IVc)
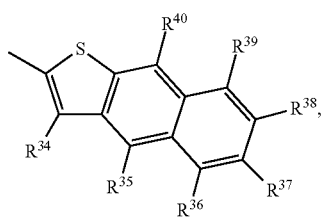 ((IVd)
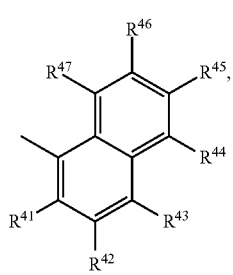 (IVe)
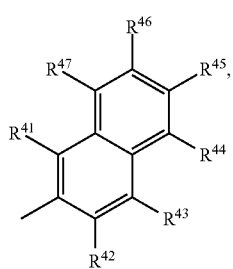 (IVf)
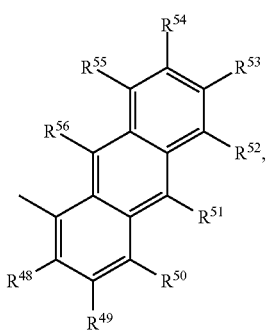 (IVg)
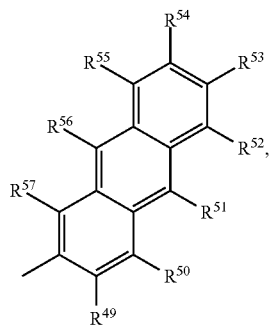 (IVh)
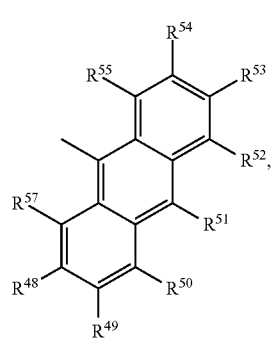 (IVi)
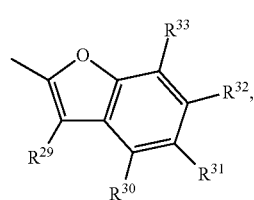 (IVj)
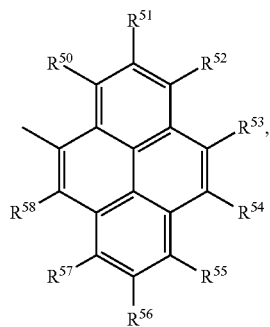 (IVk)
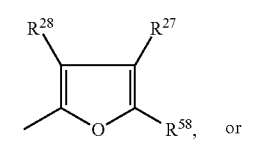 (IVl) or
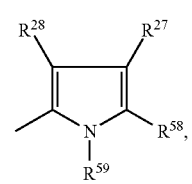 (IVm)

wherein $R^{22}$ to $R^{26}$ and $R^{29}$ to $R^{58}$ represent independently of each other H, halogen, cyano, $C_1$-$C_{25}$alkyl, $C_1$-$C_{25}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, a $C_4$-$C_{18}$cycloalkyl group, a $C_4$-$C_{18}$cycloalkyl group, which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, $C_7$-$C_{25}$aralkyl, or $C_7$-$C_{25}$aralkyl, which is substituted by G, $R^{27}$ and $R^{28}$ are independently of each other hydrogen, $C_1$-$C_{25}$alkyl, halogen, cyano or $C_7$-$C_{25}$aralkyl, or $R^{27}$ and $R^{28}$ together represent alkylene or alkenylene which may be both bonded via oxygen and/or sulfur to the thienyl residue and which may both have up to 25 carbon atoms, $R^{59}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_2$alkyl, which may optionally be interrupted by one or more oxygen or sulphur atoms; or $C_7$-$C_{25}$arylalkyl, D is —CO—, —COO—, —S—, —O—, or —$NR^{112}$—, E is $C_1$-$C_8$thioalkoxy, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H; $C_6$-$C_{18}$ aryl; $C_6$-$C_{18}$aryl which is substituted by $C_1$-$C_{18}$alkyl, or $C_1$-$C_{18}$alkoxy; $C_1$-$C_{18}$alkyl; or $C_1$-$C_{18}$alkyl which is interrupted by —O—;

$R^{172}$ is hydrogen, $C_6$-$C_{18}$aryl; $C_6$-$C_{18}$aryl which is substituted by $C_1$-$C_{18}$alkyl, or $C_1$-$C_{18}$alkoxy; or $C_1$-$C_{25}$alkyl, which may optionally be interrupted by one or more oxygen or sulphur atoms; or $C_1$-$C_{25}$arylalkyl;

$R^{214}$ and $R^{215}$ are independently of each other hydrogen, $C_1$-$C_{18}$alkyl, $C_6$-$C_{24}$aryl, $C_2$-$C_{20}$heteroaryl, —CN or $COOR^{216}$;

$R^{216}$ is $C_1$-$C_{25}$alkyl, $C_1$-$C_{25}$haloalkyl, $C_7$-$C_{25}$arylalkyl, $C_6$-$C_{24}$aryl or $C_2$-$C_{20}$heteroaryl;

$Ar^4$, $Ar^5$, $Ar^6$ and $Ar^7$ have independently of each other the meaning of $Ar^1$, and a, b, c, $Ar^1$, $Ar^2$, $Ar^3$, $R^1$ and $R^2$ are as defined in claim 1;

with the proviso that at least one of the groups $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^{8'}$, $R^9$ and $R^{9'}$ contains a group $E^{Si}$ and/or $D^{Si}$.

Preferably, at least one of the groups $R^1$ and $R^2$ contains a group $E^{Si}$ and/or $D^{Si}$. More preferred, the groups $R^1$ and $R^2$ contain a group $E^{Si}$ and/or $D^{Si}$.

Among the compounds of the formula III compounds of formula

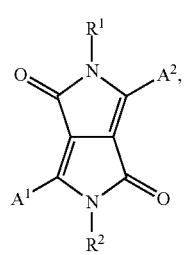
(IIIa)

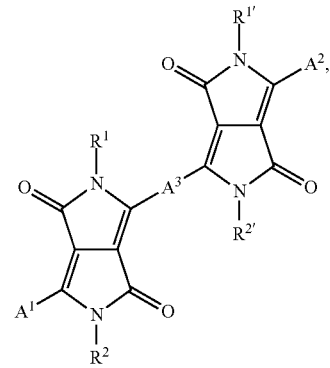
(IIIb)

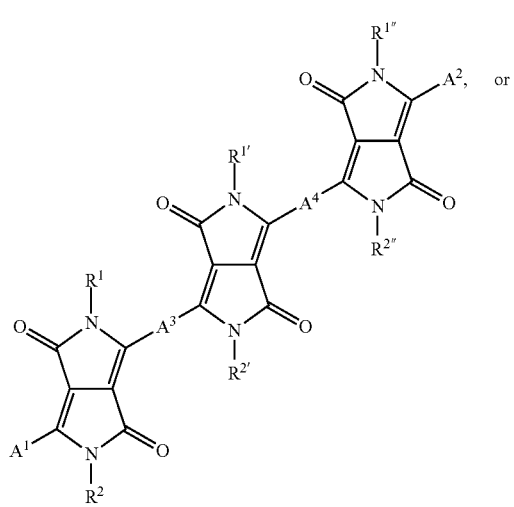
(IIIc)

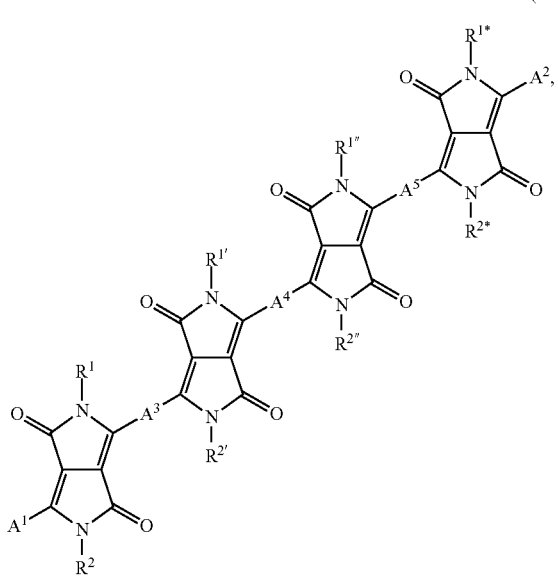
(IIId)

wherein
$R^1$, $R^2$, $A^1$, $A^2$, $A^3$, $A^4$ and $A^5$ are as defined above,
$R^{1'}$, $R^{2'}$, $R^{1''}$, $R^{2''}$, $R^{1*}$, $R^{2*}$ have independently of each other the meaning of $R^1$; with the proviso that at least one of the groups $R^1$, $R^2$, $R^{1'}$, $R^{2'}$, $R^{1''}$, $R^{2''}$, $R^{1*}$ and $R^{2*}$ is a $C_1$-$C_8$alkyl group which is substituted with $E^{Si}$, and
$E^{Si}$ is —$SiR^{161}R^{162}R^{163}$;

$R^{161}$, $R^{162}$ and $R^{163}$ are independently of each other $C_1$-$C_8$alkyl, $C_5$-$C_6$cycoalkyl, which might optionally be substituted with $C_1$-$C_4$alkyl; $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;

$R^{164}$, $R^{165}$, $R^{166}$ are independently of each other $C_1$-$C_8$alkyl, $C_1$-$C_8$haloalkyl, $C_{2-8}$alkenyl, —O—$SiR^{169}R^{170}R^{171}$, —(O—$SiR^{169}R^{170})_d$—$R^{171}$, or phenyl;

$R^{169}$, $R^{170}$, $R^{171}$ are independently of each other $C_1$-$C_8$alkyl, $C_1$-$C_8$haloalkyl, $C_2$-$C_8$alkenyl, —O—$Si(CH_3)_3$, or phenyl; and d is an integer from 1 to 10.

More preferred are compounds of the formula IIIa, IIIb and IIIc, even more preferred are compounds of the formula IIIa and IIIb, and most preferred are compounds of the formula IIIa. Preferably at least one of $R^1$, $R^2$, $R^{1'}$, $R^{2'}$, $R^{1''}$ $R^{2''}$, $R^{1*}$, $R^{2*}$ comprise a group $E^{Si}$ and/or $D^{Si}$.

More preferably $R^1$ and $R^2$ are the same, $R^{1'}$ and $R^{2'}$ are the same, $R^{1''}$ and $R^{1'}$ are the same, $R^{1*}$ and $R^{2*}$ are the same, wherein $R^1$, $R^2$, $R^{1'}$, $R^{2'}$, $R^{1''}$ $R^{2''}$, $R^{1*}$ and $R^{2*}$ contain a group $E^{Si}$ and/or $D^{Si}$.

Compounds of the formula

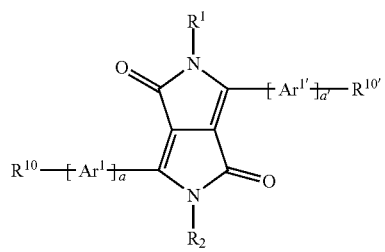

(III')

are more preferred, $R^1$ and $R^2$ are selected from $C_1$-$C_{50}$alkyl, especially $C_1$-$C_{25}$alkyl, which is substituted one or more times with $E^{Si}$ and/or interrupted one or more times with $D^{Si}$; $C_1$-$C_{50}$haloalkyl, especially $C_1$-$C_{25}$haloalkylalkyl, which is substituted one or more times with $E^{Si}$ and/or interrupted one or more times with $D^{Si}$; $C_7$-$C_{25}$arylalkyl, which is substituted one or more times with $E^{Si}$ and/or interrupted one or more times with $D^{Si}$; $C_2$-$C_{50}$alkenyl, especially $C_2$-$C_{25}$alkenyl, which is substituted one or more times with $E^{Si}$ and/or interrupted one or more times with $D^{Si}$; $C_2$-$C_{50}$alkinyl, especially $C_2$-$C_{25}$alkinyl, which is substituted one or more times with $E^{Si}$ and/or interrupted one or more times with $D^{Si}$; $C_2$-$C_{50}$haloalkenyl, especially haloalkenyl, which is substituted one or more times with $E^{Si}$ and/or interrupted one or more times with $D^{Si}$; $C_5$-$C_{12}$cycloalkyl; which is substituted one or more times with $E^{Si}$ and/or interrupted one or more times with $D^{Si}$; phenyl, or naphthyl which are substituted one or more times with $E^{Si}$. a is 1, 2, or 3, a' is 1, 2, or 3; wherein $R^{10}$, $D^{Si}$, $E^{Si}$, $Ar^1$ and $Ar^{1'}$ are as defined above. $R^{10'}$ has the meaning of $R^{10}$.

More preferred. $R^1$ and $R^2$ are $C_1$-$C_{25}$alkyl which is substituted one or more times with $E^{Si}$ and/or interrupted one or more times with $D^{Si}$; especially $C_1$-$C_{25}$alkyl which is substituted one or more times with EN, very especially $C_1$-$C_8$alkyl which is substituted one or more times with $E^{Si}$.

Even more preferred, $R^1$ and $R^2$ are selected from $C_1$-$C_{25}$alkyl, which is substituted one or more times with $E^{Si}$ and/or interrupted one or more times with $D^{Si}$.

Most preferably $R^1$ and $R^2$ are $C_1$-$C_8$alkyl which is substituted with $E^{Si}$. $R^1$ and $R^2$ may be different, but are preferably the same.

$Ar^1$ and $Ar^{1'}$ may be different, but are preferably the same. Preferably, $Ar^1$ and $Ar^{1'}$ are independently of each a group of formula XIa, XIb, XIc, XIe, XIf, XII, XIp, XIr, XIIs, XIx, XIIf, XIIg, XIIIa, XIIId, or XIIII. More preferably, $Ar^1$ and $Ar^{1'}$ are a group of formula XIa, XIb, XIe, XIf, XIr, XIx, or XIIIa. Still more preferably $Ar^1$ and $Ar^{1'}$ are a group of formula XIa, XIb, or XIf. Most preferred $Ar^1$ and $Ar^{1'}$ are a group of formula XIa, or XIf, especially XIa.

Among the compounds of formula IIIa compounds of formula

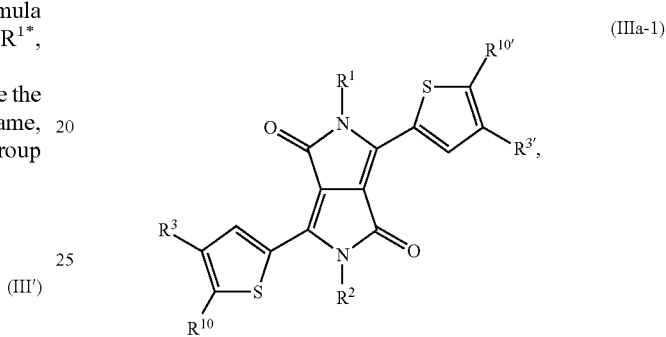

(IIIa-1)

especially

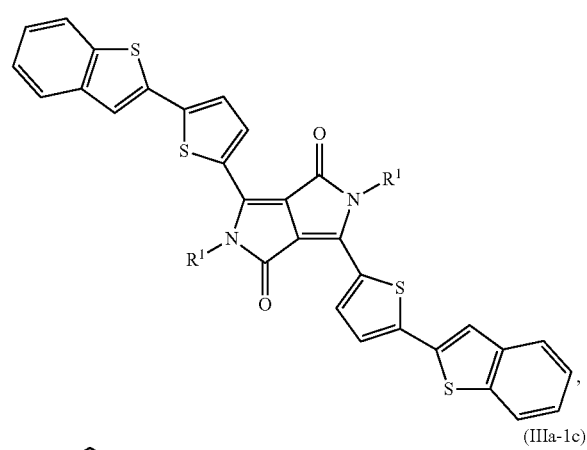

(IIIa-1b)

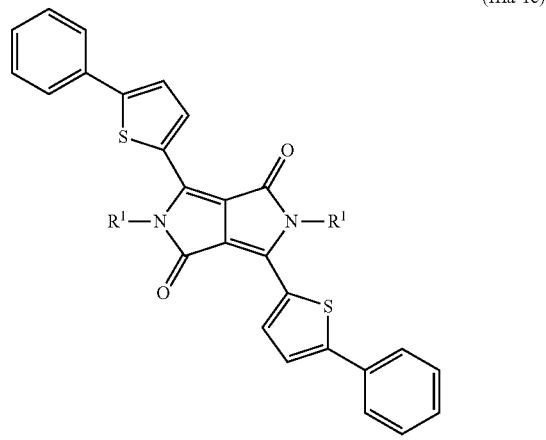

(IIIa-1c)

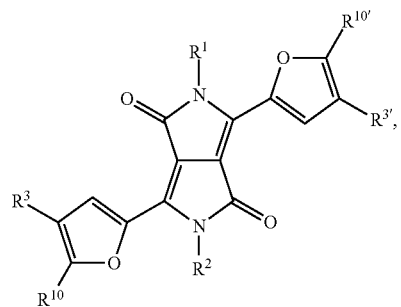
(IIIa-2)
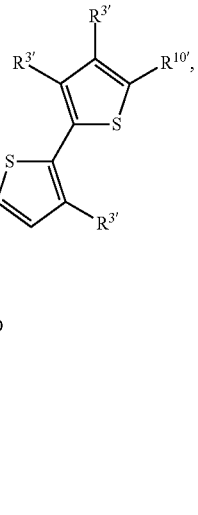
(IIIa-3)
especially
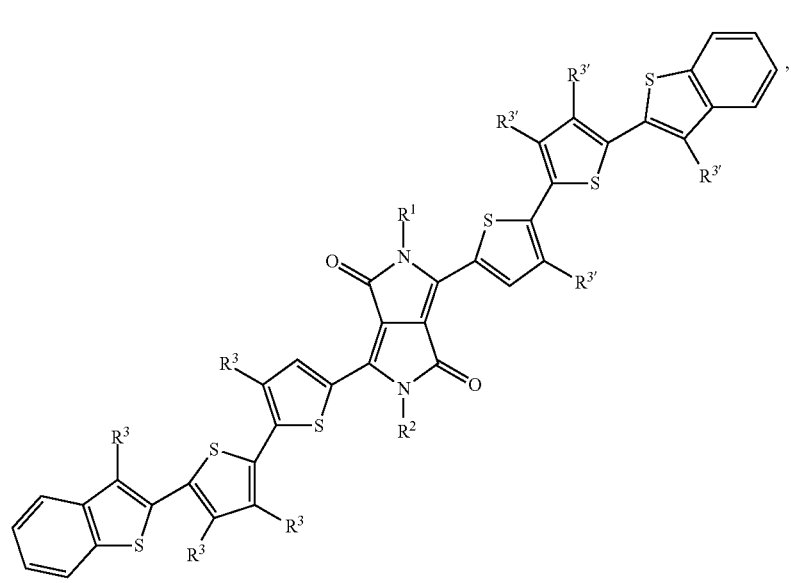
(IIIa-3′), or
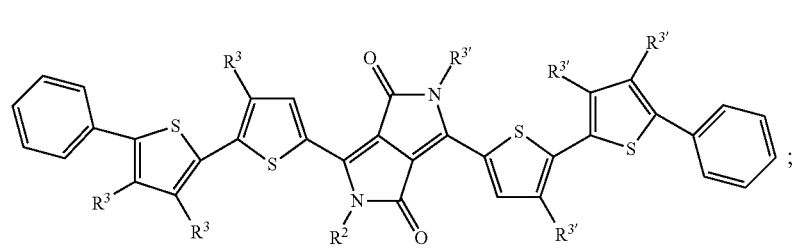
(IIIa-3″);

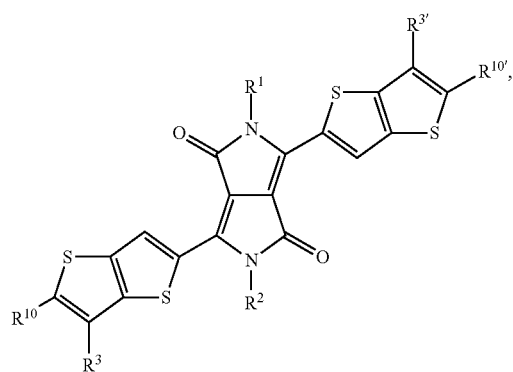
(IIIa-4)
especially
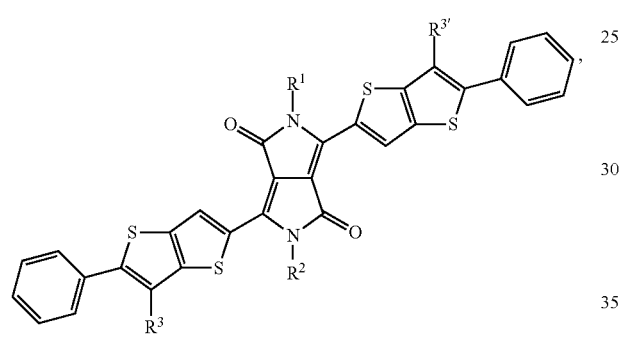
(IIIa-4′)
very especially
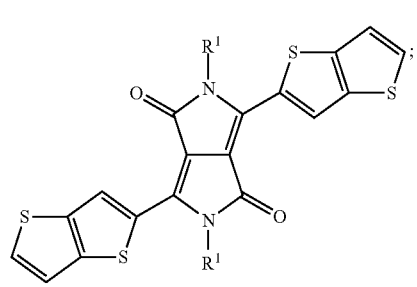
(IIIa-4a)
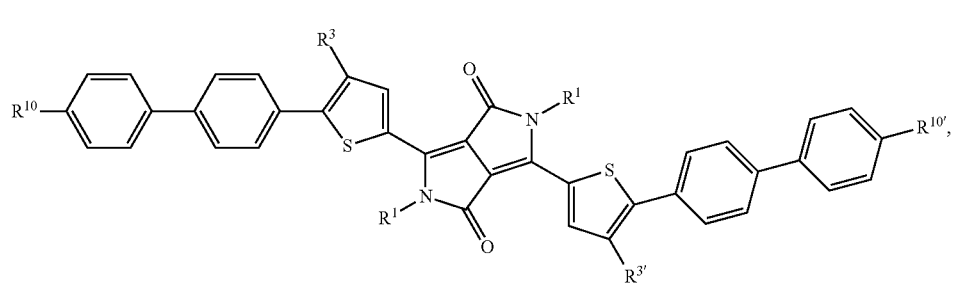
(IIIa-5)

-continued
(IIIa-6)
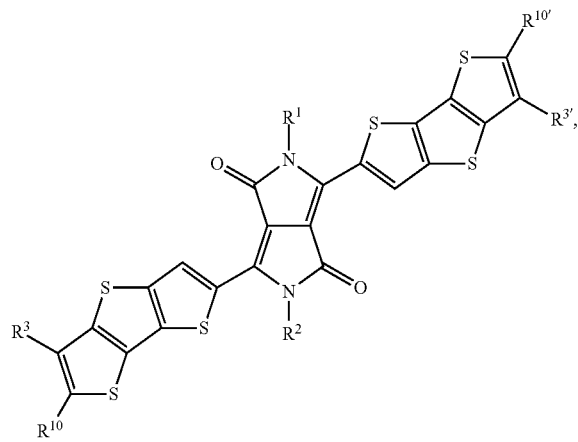
(IIIa-7)
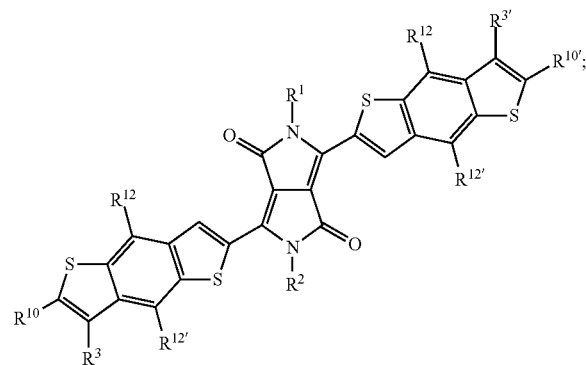
(IIIa-8)
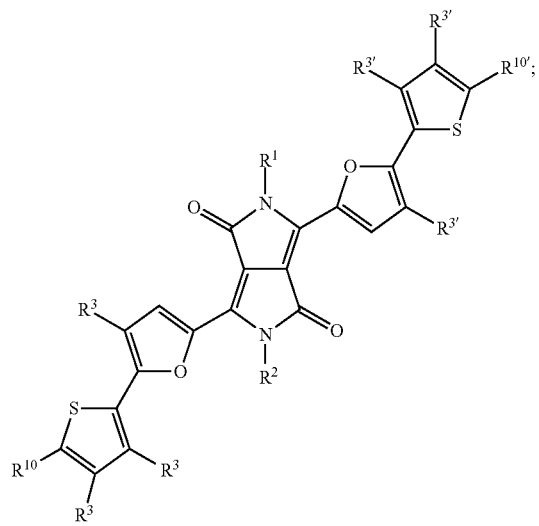
(IIIa-9)
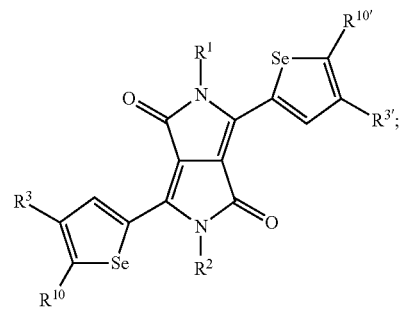
(IIIa-10)
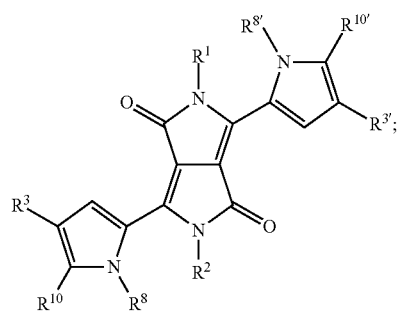
(IIIa-11)
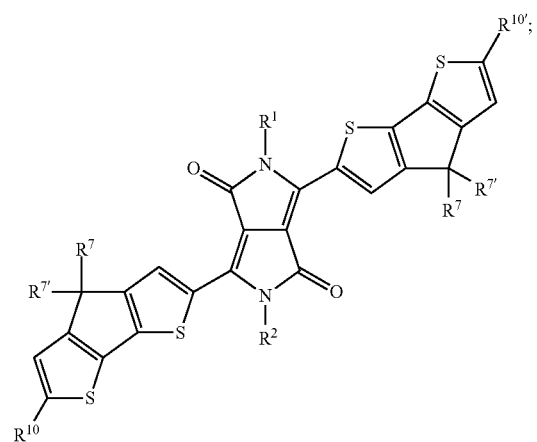

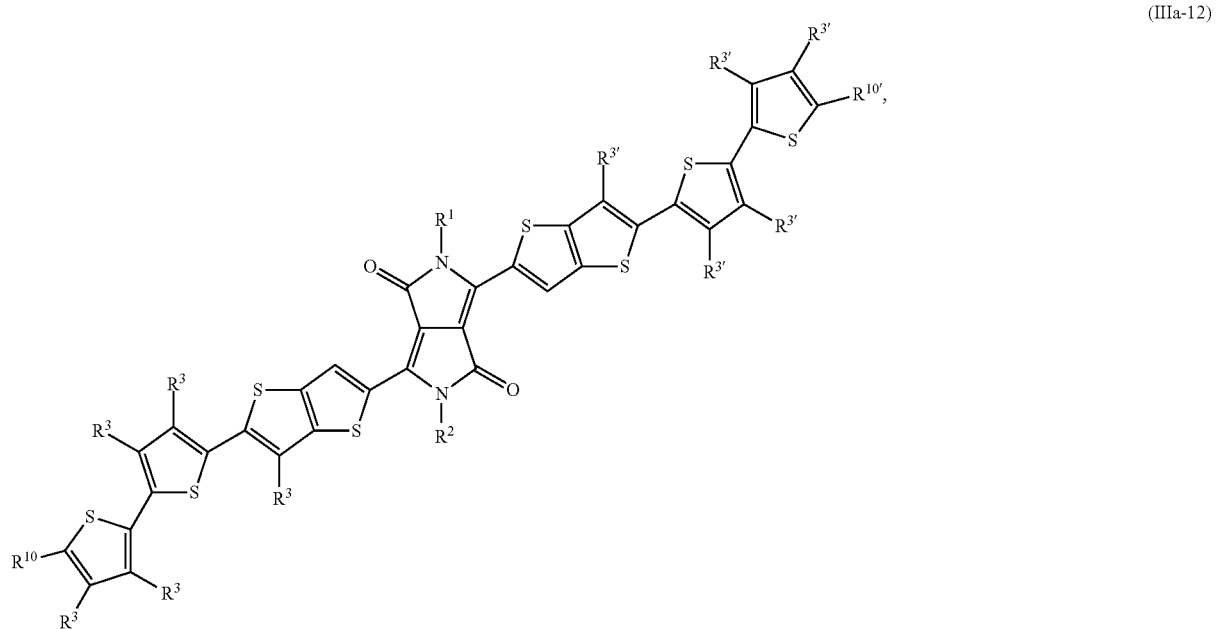
(IIIa-12)
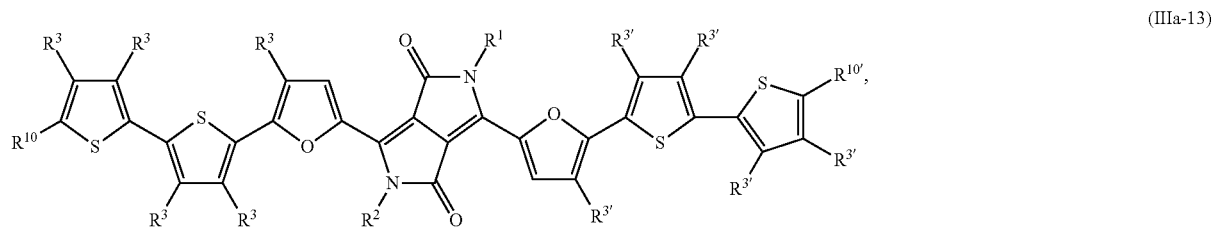
(IIIa-13)
especially
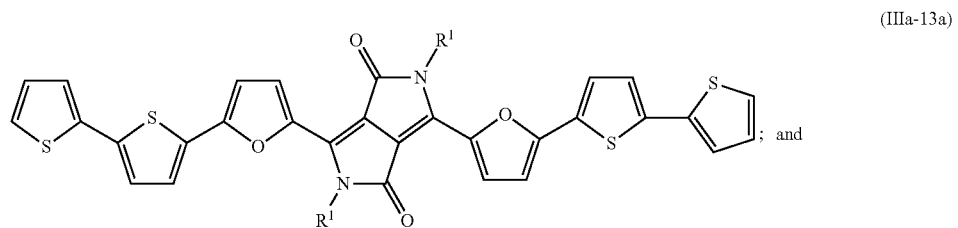
(IIIa-13a)
; and
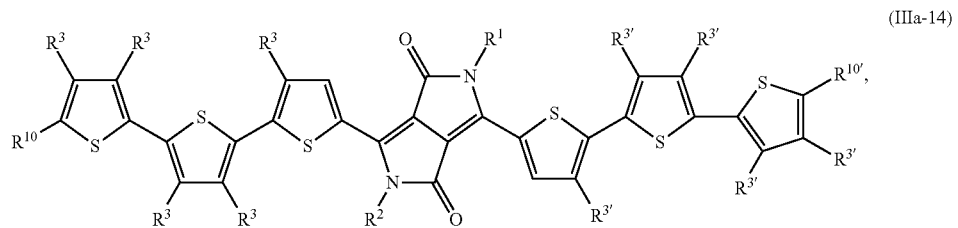
(IIIa-14)

especially

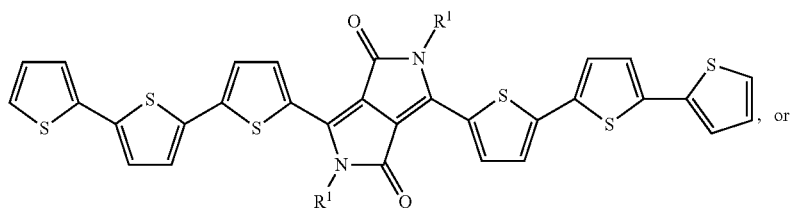
(IIIa-14a), or

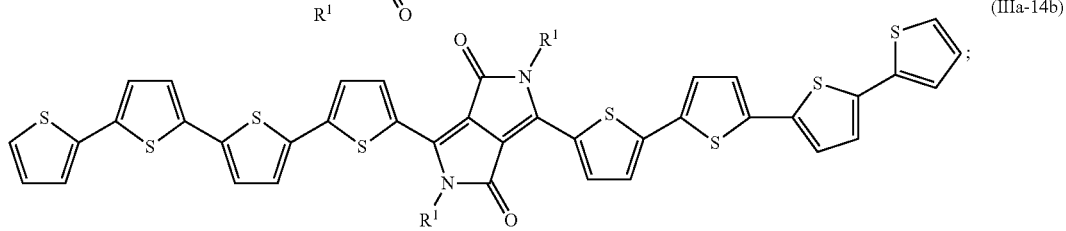
(IIIa-14b);

are more preferred, wherein $R^{10}$ and $R^{10'}$ are as defined above, $R^1$ and $R^2$ may be the same or different and are selected from $C_1$-$C_{25}$alkyl, which is substituted one or more times with $E^{Si}$ and/or interrupted one or more times with $D^{Si}$;

$R^3$ and $R^{3'}$ are independently of each other hydrogen, halogen, cyano or $C_1$-$C_{25}$alkyl, especially hydrogen or $C_1$-$C_{25}$alkyl;

$R^7$ and $R^{7'}$ are independently of each other hydrogen, $C_1$-$C_{25}$alkyl, $C_1$-$C_{25}$alkyl substituted with one or more $E^{Si}$, more preferably $C_4$-$C_{25}$alkyl;

$R^8$ and $R^{8'}$ are independently of each other hydrogen, $C_1$-$C_{25}$alkyl, $C_1$-$C_{25}$alkyl substituted with one or more $E^{Si}$, $C_1$-$C_{25}$alkyl, which may optionally be interrupted by one or more oxygen or sulphur atoms; more preferably hydrogen, or $C_1$-$C_{25}$alkyl; and $R^{12}$ and $R^{12'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or —≡—$R^{13}$, wherein $R^{13}$ is a $C_1$-$C_{10}$alkyl group, or a tri($C_1$-$C_8$alkyl)silyl group.

$R^{10}$ and $R^{10'}$ are preferably H, F, trifluoromethyl, cyano, $C_1$-$C_{25}$alkyl, a group of formula

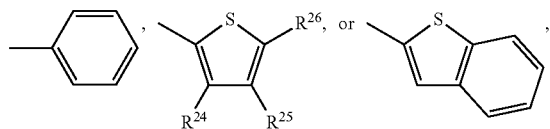

wherein $R^{24}$ to $R^{26}$ are as defined above and are preferably H, or $C_1$-$C_{25}$alkyl, more preferably H.

Among compounds of formula (IIa-1) to (IIIa-14) compounds are more preferred, wherein $R^1$ and $R^2$ may be the same or different and are selected from $C_1$-$C_{25}$alkyl, which is substituted one or more times with $E^{Si}$ and/or interrupted one or more times with $D^{Si}$;

$R^3$ and $R^{3'}$ are hydrogen or $C_1$-$C_{25}$alkyl;

$R^7$ and $R^{7'}$ are $C_4$-$C_{25}$alkyl;

$R^8$ and $R^{8'}$ are hydrogen, or $C_1$-$C_{25}$alkyl;

$R^{10}$ and $R^{10''}$ are preferably H, F, trifluoromethyl, cyano, $C_1$-$C_{25}$alkyl, a group of formula

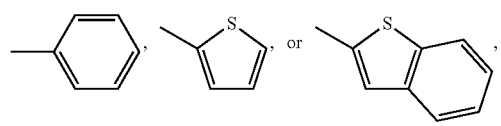

and $R^{12}$ and $R^{17}$ are independently of each other hydrogen, cyano, $C_1$-$C_{25}$alkyl, or —≡—$R^{13}$, wherein $R^{13}$ is a $C_1$-$C_{10}$alkyl group, or a tri($C_1$-$C_8$alkyl)silyl group.

Examples of specific compounds are shown below:

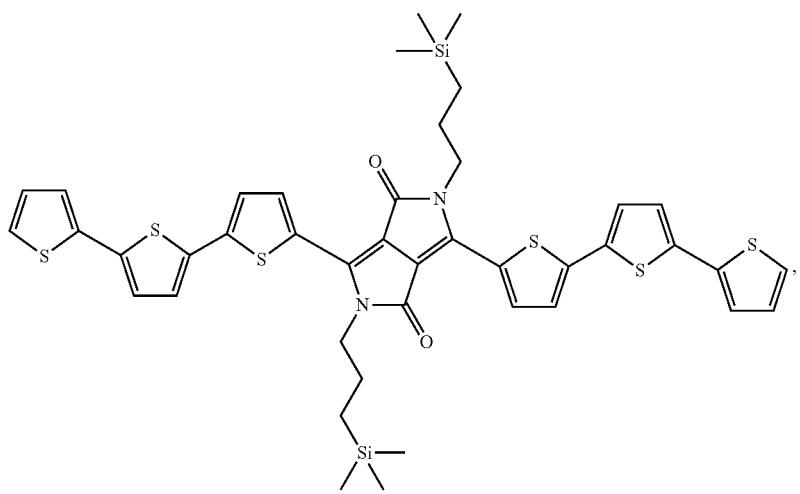
(B-1)

(B-2)
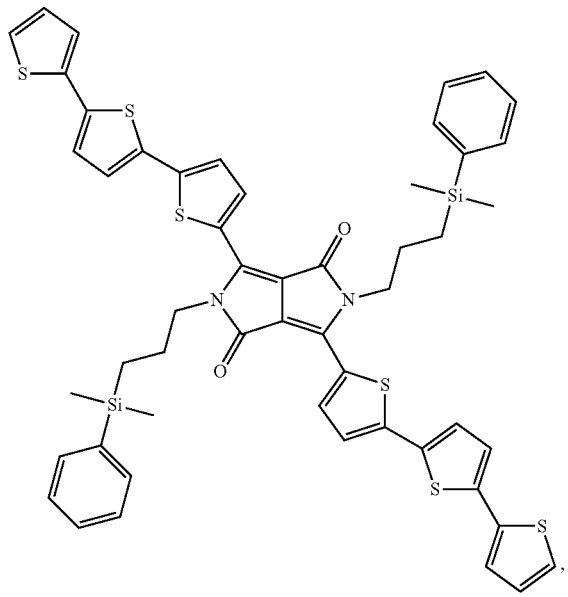
(B-3)
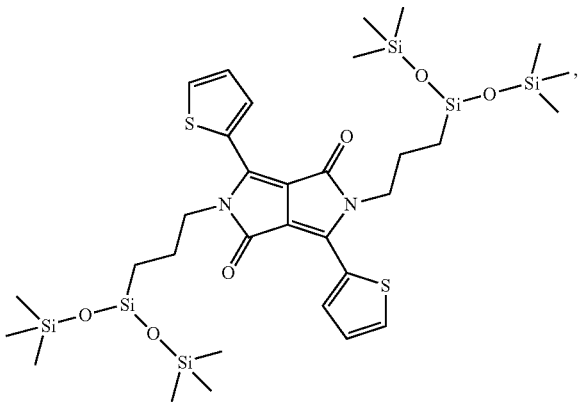
(B-4)
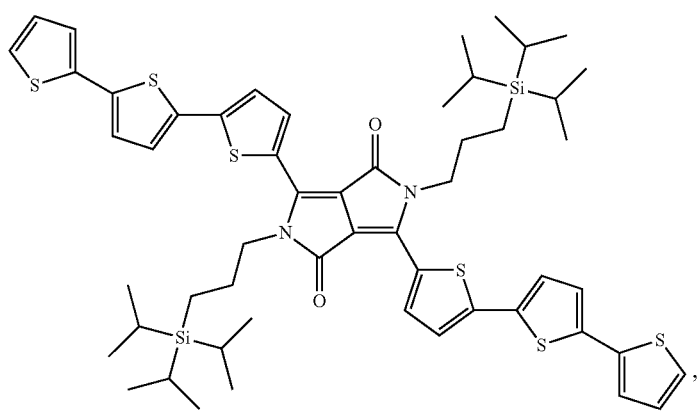
(B-5)
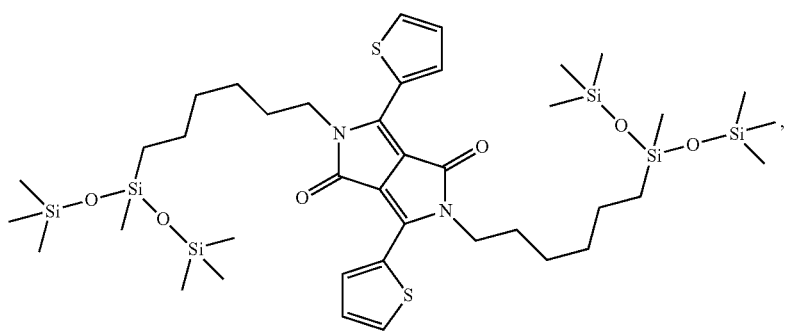

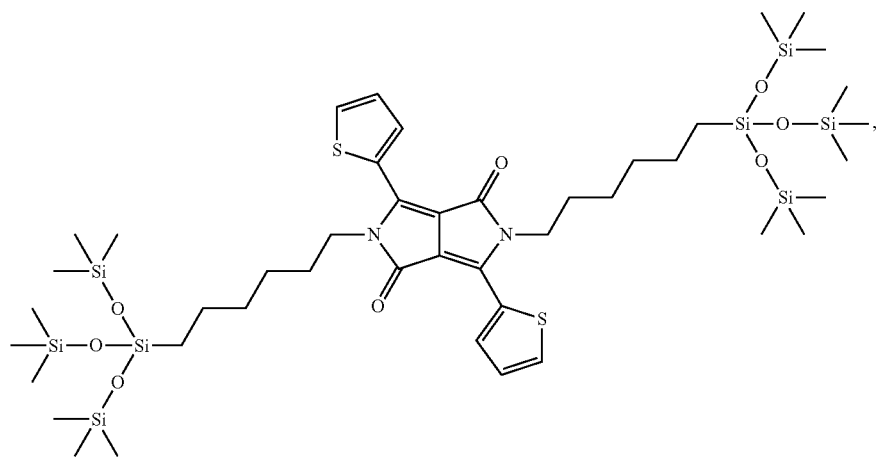
(B-6)
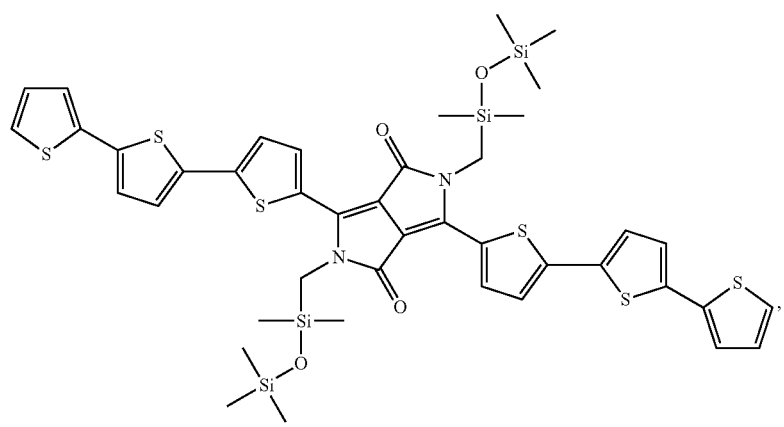
(B-7)
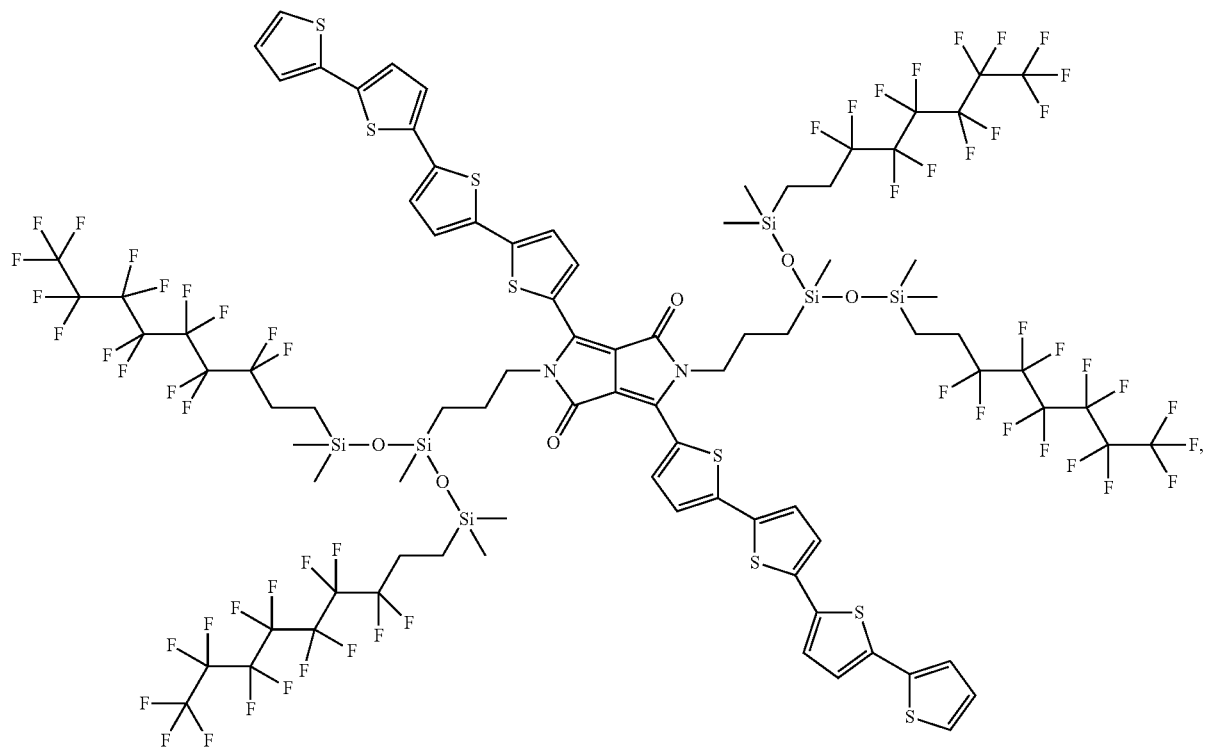
(B-8)

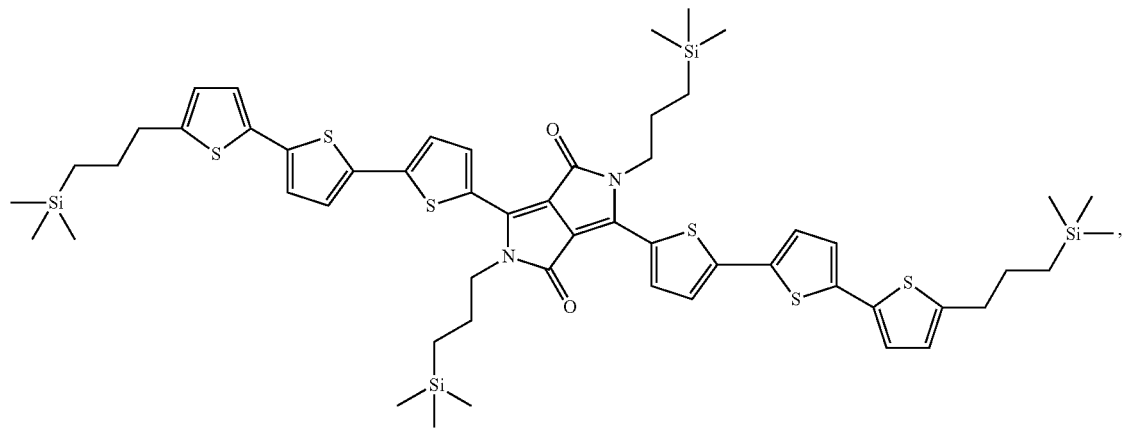
(B-9)
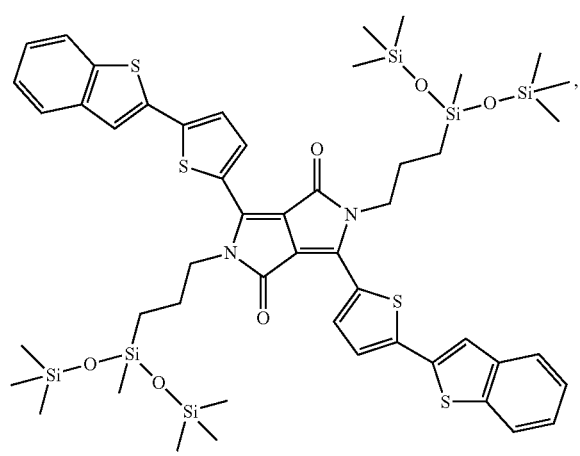
(B-10)
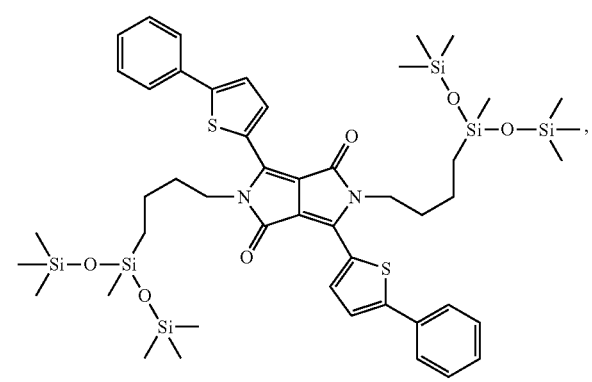
(B-11)
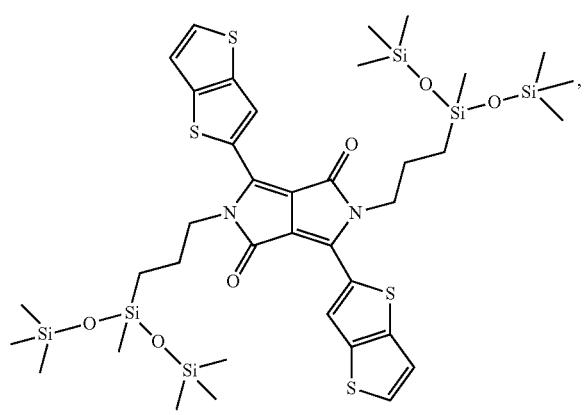
(B-12)
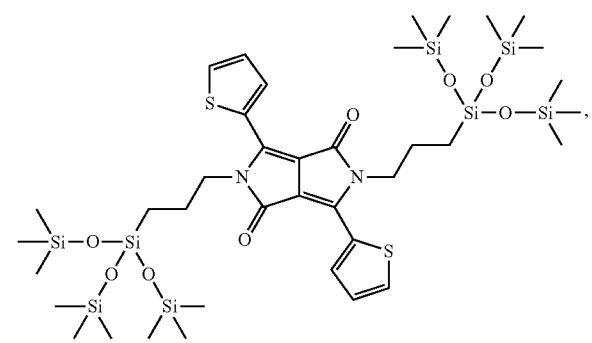
(B-13)

-continued
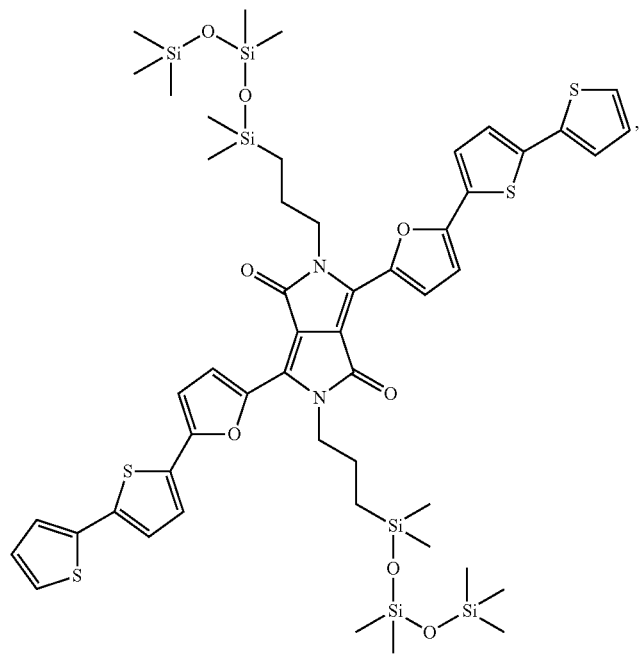
(B-14)
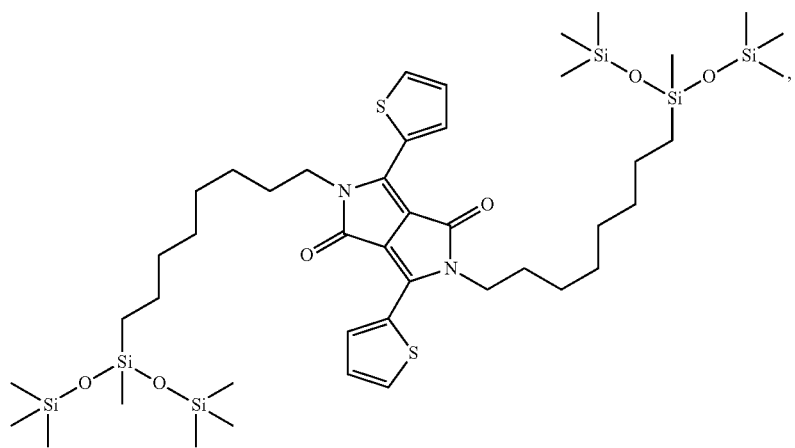
(B-15)
(B-16)
(B-17)
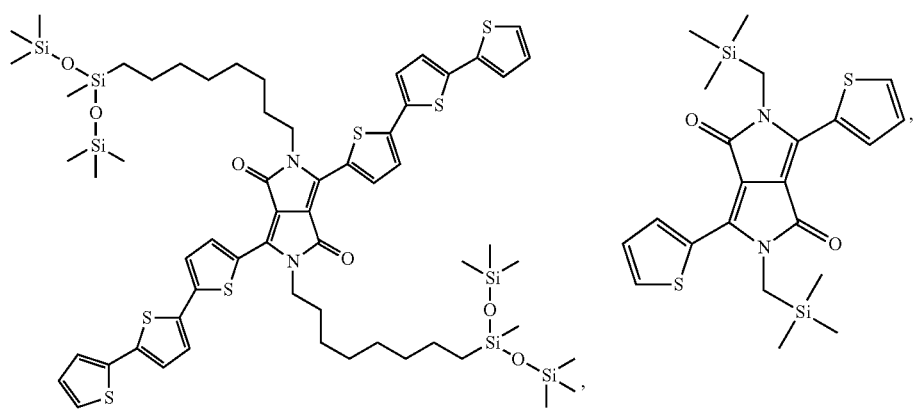

-continued
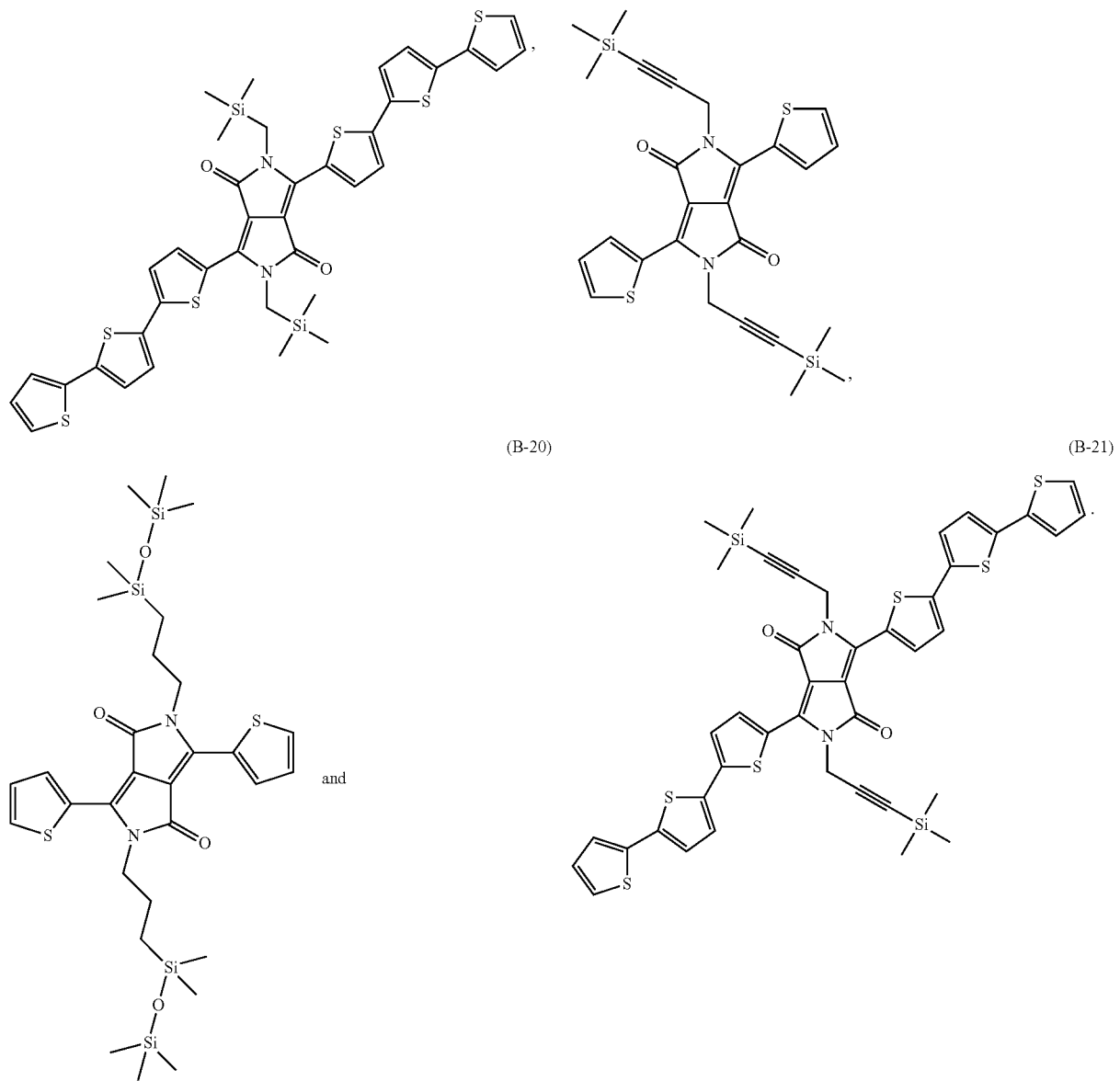
In another preferred embodiment the present invention is directed to compounds of formula
(IIIb)
wherein $R^1$, $R^2$, $A^1$, $A^2$ and $A^3$ are as defined above. $R^{1'}$ and $R^{2'}$ have independently of each other the meaning of $R^1$.
Preferably, $A^1$ and $A^2$ are independently of each other a group of formula
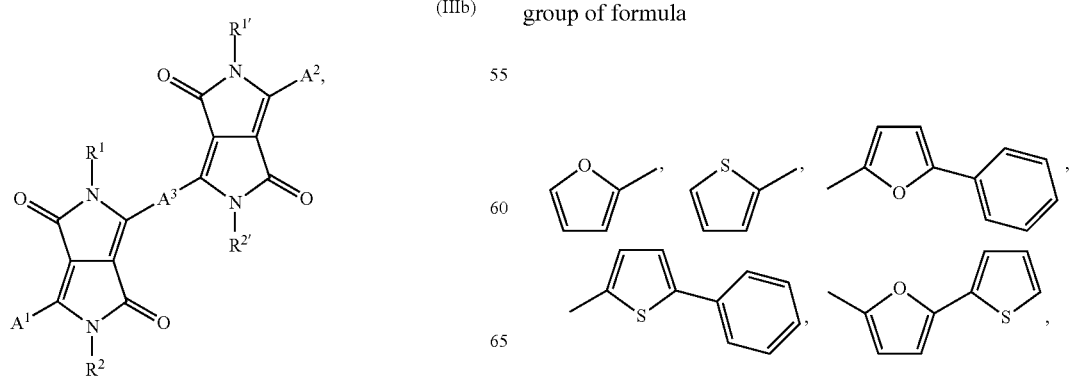

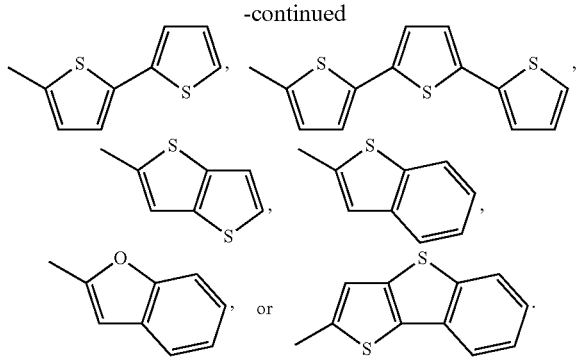

Preferably, $A^3$ is a group of formula

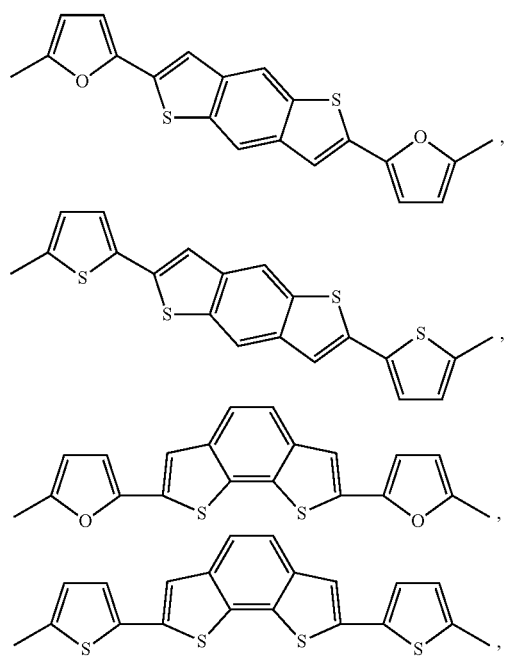

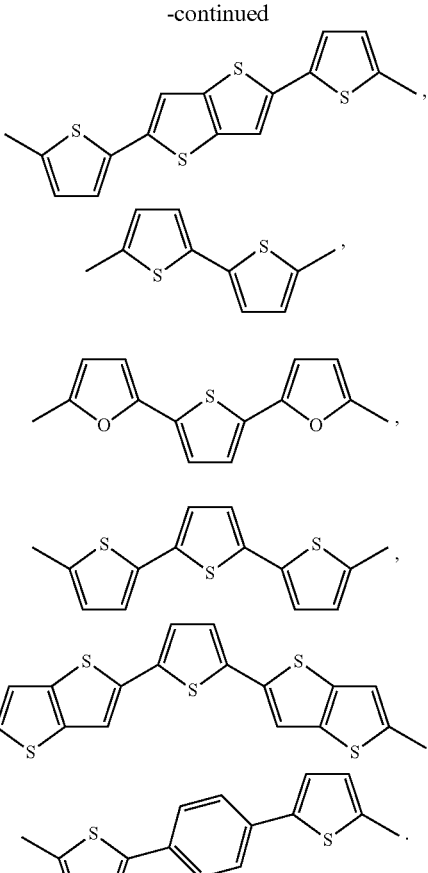

$R^1$ and $R^2$ may be the same or different and are preferably selected from $C_1$-$C_{25}$alkyl, which is substituted one or more times with $E^{Si}$ and/or interrupted one or more times with $D^{Si}$.

$R^{1'}$ and $R^{2'}$ may be the same or different and are preferably selected from $C_1$-$C_{25}$alkyl, which is substituted one or more times with $E^{Si}$ and/or interrupted one or more times with $D^{Si}$.

Examples of a compound of formula IIIb are shown below:

(C-1)

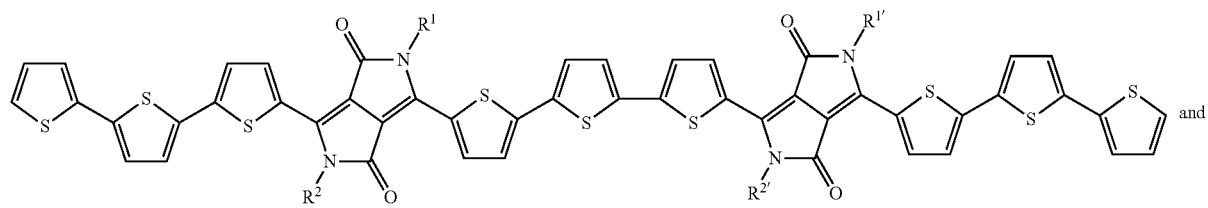

and (C-2)

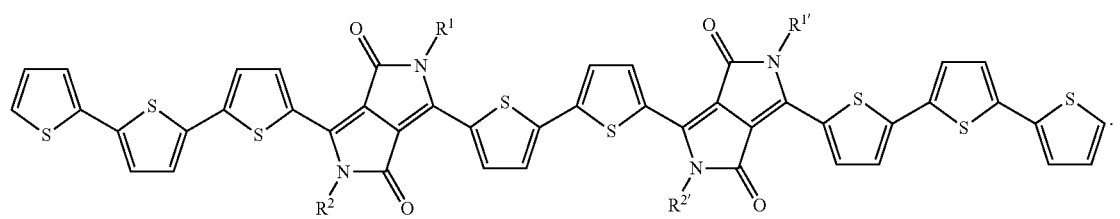

Compounds of the formula

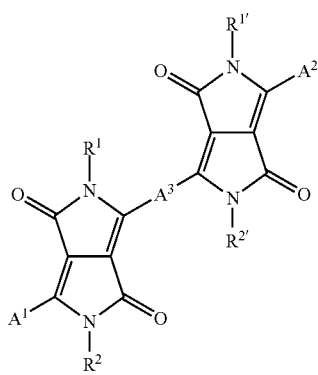

(IIIb)

($A^3$ is a group of formula, *⎯[$Ar^4$]$_k$⎯[$Ar^5$]$_l$⎯[$Ar^6$]$_r$⎯ [$Ar^7$]$_z$-*, $Ar^4$ is $Ar^7$, k is 1, or 2, z is 1, or 2) may be prepared by reacting a compound of formula

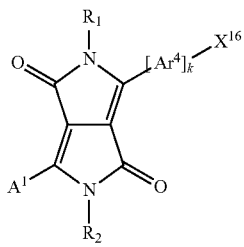

with a compound of formula $X^{16'}$⎯[$Ar^5$]$_l$⎯[$Ar^6$]$_r$⎯$X^{16'}$, wherein $X^{16'}$ is —B(OH)$_2$, —B(OH)$_3$—, —BF$_3$, —B(OY$^1$)$_2$,

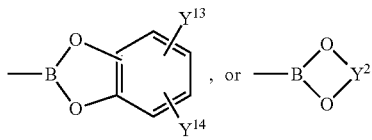

and $X^{16}$ is halogen, such as, for example, Br, or I.

The Suzuki reaction is typically conducted at about 0° C. to 180° C. in an aromatic hydrocarbon solvent such as toluene, xylene. Other solvents such as dimethylformamide, dioxane, dimethoxyethan and tetrahydrofuran can also be used alone, or in mixtures with an aromatic hydrocarbon. An aqueous base, preferably sodium carbonate or bicarbonate, potassium phosphate, potassium carbonate or bicarbonate is used as activation agent for the boronic acid, boronate and as the HBr scavenger. A condensation reaction may take 0.2 to 100 hours. Organic bases, such as, for example, tetraalkylammonium hydroxide, and phase transfer catalysts, such as, for example TBAB, can promote the activity of the boron (see, for example, Leadbeater & Marco; Angew. Chem. Int. Ed. Eng. 42 (2003) 1407 and references cited therein). Other variations of reaction conditions are given by T. I. Wallow and B. M. Novak in J. Org. Chem. 59 (1994) 5034-5037; and M. Remmers, M. Schulze, and G. Wegner in Macromol. Rapid Commun. 17 (1996) 239-252.

In the above Suzuki coupling reactions the halogen $X^{16}$ on the halogenated reaction partner can be replaced with the $X^{16'}$ moiety and at the same time the $X^{16'}$ moiety of the other reaction partner is replaced by $X^{16}$.

In an additional embodiment the present invention is directed to compounds of formula $A^{1''}$-Y-$A^3$-$Y^{15}$⎯[$A^4$-$Y^{16}$]$_p$⎯[$A^5$-$Y^{17}$]$_q$$A^{2''}$ (XX), wherein
$A^{1''}$ and $A^{2''}$ are independently of each other a group of formula ⎯[$Ar^1$]$_a$⎯[$Ar^2$]$_b$⎯[$Ar^3$]$_c$—$X^3$,
$X^3$ is independently in each occurrence ZnX$^{12}$, —SnR$^{207}$R$^{208}$R$^{209}$, wherein R$^{207}$, R$^{208}$ and R$^{209}$ are identical or different and are H or C$_1$-C$_6$alkyl, wherein two groups optionally form a common ring and these groups are branched or unbranched a $X^{12}$ is a halogen atom, very especially I, or Br; —OS(O)$_2$CF$_3$, —OS(O)$_2$-a, especially

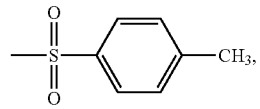

OS(O)$_2$CH$_3$, —B(OH)$_2$, —B(OH)$_3$—, —BF$_3$—, —B(OY$^1$)$_2$,

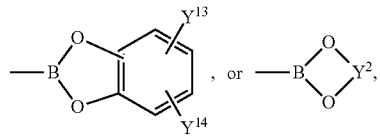

wherein Y$^1$ is independently in each occurrence a C$_1$-C$_{12}$alkyl group and Y$^2$ is independently in each occurrence a C$_2$-C$_{10}$alkylene group, such as —CY$^3$Y$^4$—CY$^5$Y$^6$—, or —CY$^7$Y$^8$—CY$^9$Y$^{10}$—CY$^{11}$—Y$^{12}$—, wherein Y$^3$, Y$^4$, Y$^5$, Y$^6$, Y$^7$, Y$^8$, Y$^9$, Y$^{10}$, Y$^{11}$ and Y$^{12}$ are independently of each other hydrogen, or a C$_1$-C$_{12}$alkyl group, especially —C(CH$_3$)$_2$ C(CH$_3$)$_2$—, or —C(CH$_3$)$_2$CH$_2$C(CH$_3$)$_2$—, —CH$_2$C(CH$_3$)$_2$ CH$_2$—, and Y$^{13}$ and Y$^{14}$ are independently of each other hydrogen, or a C$_1$-C$_{12}$alkyl group; a, b, c, p, q, Ar$^1$, Ar$^2$, Ar$^3$, Y, Y$^{15}$, Y$^{16}$, Y$^{17}$, A$^3$, A$^4$ and A$^5$ are as defined above.

The compound of formula XX is preferably a compound of formula $A^{1''}$-Y-$A^3$-$Y^{15}$-$A^{2''}$ (XXa). The compounds of the formula XX, especially XXa are intermediates in the production of polymers.

Accordingly, the present invention is also directed to polymers comprising repeating units of formula -$A^{1'}$-Y-$A^3$-$Y^{15}$⎯[$A^4$-$Y^{16}$]$_p$⎯[$A^5$-$Y^{15}$]$_q$$A^{2''}$-(X), wherein
$A^{1''}$ and $A^{2''}$ are independently of each other a group of formula ⎯[$Ar^1$]$_a$⎯[$Ar^2$]$_b$⎯[$Ar^3$]$_c$—, wherein a, b, c, p, q, Ar$^1$, Ar$^2$, Ar$^3$, Y, Y$^{15}$, Y$^{16}$, Y$^{17}$, A$^3$, A$^4$ and A$^5$ are as defined above. The polymers of the present invention may be used in the production of semiconductor devices. Accordingly, the present invention is also directed to semiconductor devices comprising a polymer of the present invention.

Advantageously, the compound of formula III, or an organic semiconductor material, layer or component, comprising the compound of formula III can be used in organic photovoltaics (solar cells) and photodiodes, or in an organic field effect transistor (OFET).

A mixture containing the compound of formula III results in a semi-conducting layer comprising the compound of formula III (typically 0.1% to 99.9999% by weight, more specifically 1% to 99.9999% by weight, even more specifically 5% to 99.9999% by weight, especially 20 to 85% by weight) and at least another material. The other material can be, but is not restricted to another compound of formula III, a polymer of the present invention, a semiconducting polymer, a non-conductive polymer, organic small molecules, carbon nanotubes, a fullerene derivative, inorganic particles (quantum dots, quantum rods, quantum tripods, $TiO_2$, ZnO etc.), conductive particles (Au, Ag etc.), insulator materials like the ones described for the gate dielectric (PET, PS etc.).

Accordingly, the present invention also relates to an organic semiconductor material, layer or component, comprising a compound of formula III and to a semiconductor device, comprising a compound of formula III and/or an organic semiconductor material, layer or component.

The semiconductor is preferably an organic photovoltaic (PV) device (solar cell), a photodiode, or an organic field effect transistor. The structure and the components of the OFET device has been described in more detail above.

Accordingly, the invention provides organic photovoltaic (PV) devices (solar cells) comprising a compound of the formula III.

The structure of organic photovoltaic devices (solar cells) is, for example, described in C. Deibel et al. Rep. Prog. Phys. 73 (2010) 096401 and Christoph Brabec, Energy Environ. Sci 2. (2009) 347-303.

The PV device comprise in this order:
(a) a cathode (electrode),
(b) optionally a transition layer, such as an alkali halogenide, especially lithium fluoride,
(c) a photoactive layer,
(d) optionally a smoothing layer,
(e) an anode (electrode),
(f) a substrate.

The photoactive layer comprises the compounds of the formula III. Preferably, the photoactive layer is made of a compound of the formula III, as an electron donor and an acceptor material, like a fullerene, particularly a functionalized fullerene PCBM, as an electron acceptor. As stated above, the photoactive layer may also contain a polymeric binder. The ratio of the small molecules of formula III to the polymeric binder can vary from 5 to 95 percent. Preferably, the polymeric binder is a semicristalline polymer such as polystyrene (PS), high-density polyethylene (HDPE), polypropylene (PP) and polymethylmethacrylate (PMMA).

The fullerenes useful in this invention may have a broad range of sizes (number of carbon atoms per molecule). The term fullerene as used herein includes various cage-like molecules of pure carbon, including Buckminsterfullerene ($C_{60}$) and the related "spherical" fullerenes as well as carbon nanotubes. Fullerenes may be selected from those known in the art ranging from, for example, $C_{20}$-$C_{1000}$. Preferably, the fullerene is selected from the range of $C_{60}$ to $C_{96}$. Most preferably the fullerene is $C_{60}$ or $C_{70}$, such as [60]PCBM, or [70]PCBM. It is also permissible to utilize chemically modified fullerenes, provided that the modified fullerene retains acceptor-type and electron mobility characteristics. The acceptor material can also be a material selected from the group consisting of another compounds of formula III, or any semi-conducting polymer, such as, for example, a polymer of formula I, provided that the polymers retain acceptor-type and electron mobility characteristics, organic small molecules, carbon nanotubes, inorganic particles (quantum dots, quantum rods, quantum tripods, $TiO_2$, ZnO etc.).

The photoactive layer is made of a compound of the formula III, as an electron donor and a fullerene, particularly functionalized fullerene PCBM, as an electron acceptor. These two components are mixed with a solvent and applied as a solution onto the smoothing layer by, for example, the spin-coating method, the drop casting method, the Langmuir-Blodgett ("LB") method, the ink jet printing method and the dripping method. A squeegee or printing method could also be used to coat larger surfaces with such a photoactive layer. Instead of toluene, which is typical, a dispersion agent such as chlorobenzene is preferably used as a solvent. Among these methods, the vacuum deposition method, the spin-coating method, the ink jet printing method and the casting method are particularly preferred in view of ease of operation and cost.

In the case of forming the layer by using the spin-coating method, the casting method and ink jet printing method, the coating can be carried out using a solution and/or dispersion prepared by dissolving, or dispersing the composition in a concentration of from 0.01 to 90% by weight in an appropriate organic solvent such as benzene, toluene, xylene, tetrahydrofurane, methyttetrahydrofurane, N,N-dimethylformamide, acetone, acetonitrile, anisole, dichloromethane, dimethylsulfoxide, chlorobenzene, 1,2-dichlorobenzene and mixtures thereof.

The photovoltaic (PV) device can also consist of multiple junction solar cells that are processed on top of each other in order to absorb more of the solar spectrum. Such structures are, for example, described in App. Phys. Let. 90, 143512 (2007), Adv. Funct. Mater. 16, 1897-1903 (2006) and WO2004/112161.

A so called 'tandem solar cell' comprise in this order
(a) a cathode (electrode),
(b) optionally a transition layer, such as an alkali halogenide, especially lithium fluoride,
(c) a photoactive layer,
(d) optionally a smoothing layer,
(e) a middle electrode (such as Au, Al, ZnO, $TiO_2$ etc.)
(f) optionally an extra electrode to match the energy level,
(g) optionally a transition layer, such as an alkali halogenide, especially lithium fluoride,
(h) a photoactive layer,
(i) optionally a smoothing layer,
(j) an anode (electrode),
(k) a substrate.

The PV device can also be processed on a fiber as described, for example, in US20070079867 and US 20060013549.

Due to their excellent self-organising properties the materials or films comprising the compounds of the formula III can also be used alone or together with other materials in or as alignment layers in LCD or OLED devices, as described for example in US2003/0021913.

An OFET device according to the present invention preferably comprises:
a source electrode,
a drain electrode,
a gate electrode,
a semiconducting layer,
one or more gate insulator layers, and
optionally a substrate, wherein the semiconductor layer comprises a compound of formula III.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

Preferably the OFET comprises an insulator having a first side and a second side, a gate electrode located on the first side of the insulator, a layer comprising a compound of formula III located on the second side of the insulator, and a drain electrode and a source electrode located on the polymer layer.

The following examples are included for illustrative purposes only and do not limit the scope of the claims. Unless otherwise stated, all parts and percentages are by weight. Weight-average molecular weight (Mw) and polydispersity (Mw/Mn=PD) are determined by Heat Temperature Gel Permeation Chromatography (HT-GPC) [Apparatus: GPC PL 220 from Polymer laboratories (Church Stretton, UK; now Varian) yielding the responses from refractive index (RI), Chromatographic conditions: Column: 3 "PLgel Olexis" column from Polymer Laboratories (Church Stretton, UK); with an average particle size of 13 im (dimensions 300×8 mm I.D.) Mobile phase: 1,2,4-trichlorobenzene purified by vacuum distillation and stabilised by butyihydroxytoluene (BHT, 200 mg/l), Chromatographic temperature: 150° C.; Mobile phase flow: 1 ml/min; Solute concentration: about 1 mg/ml; Injection volume: 200 il; Detection: RI, Procedure of molecular weight calibration: Relative calibration is done by use of a set of 10 polystyrene calibration standards obtained from Polymer Laboratories (Church Stretton, UK) spanning the molecular weight range from 1'930'000 Da-5'050 Da, i. e., PS 1'930'000, PS 1'460'000, PS 1'075'000, PS 560'000, PS 330'000, PS 96'000, PS 52'000, PS 30'300, PS 10'100, PS 5'050 Da. A polynomic calibration is used to calculate the molecular weight.

All polymer structures given in the examples below are idealized representations of the polymer products obtained via the polymerization procedures described. If more than two components are copolymerized with each other sequences in the polymers can be either alternating or random depending on the polymerisation conditions.

EXAMPLES

Example 1

Synthesis of Compound 6 (B-1)

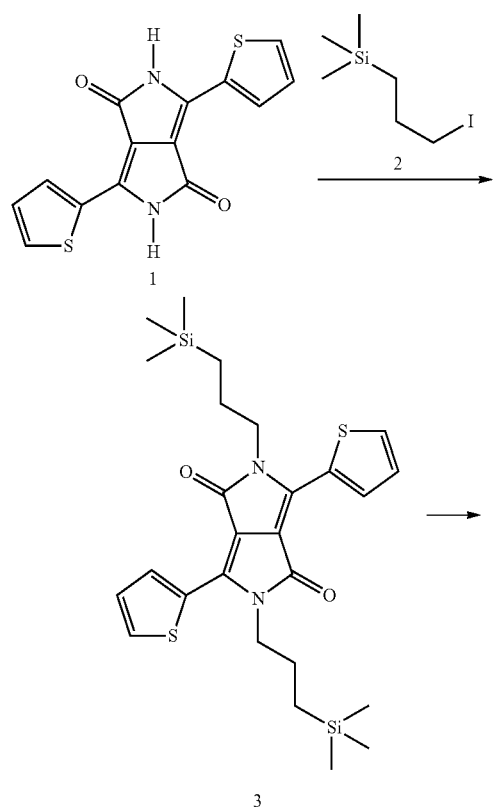

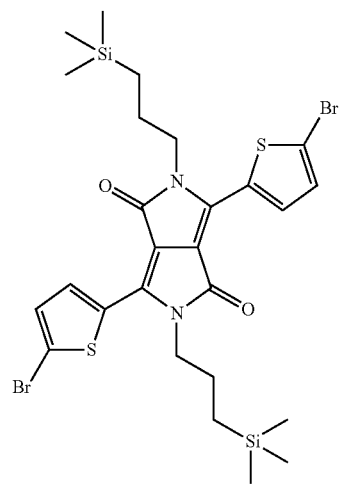

a) 10 g of compound 1 [850583-75-4] and 18.43 g of potassium carbonate are dispersed in 100 ml of dry dimethylformamide. The mixture is heated to 100° C. for two hours and then 17.76 g of compound 2 [18135-48-3] are added and the reaction mixture is stirred for another hour at 100° C. The reaction mixture is cooled to room temperature and then poured on water. The product is extracted with chloroform. The organic phase is dried over MgSO$_4$ and the solvent is evaporated. The product is purified over silica gel by chromatography to give compound 3. $^1$H-NMR data (ppm, CDCl$_3$): 8.96 2H d, 7.65 2H d, 7.31 2H dxd, 4.07 4H t, 1.81-1.70 4H m, 0.62 4H m, 0.01 18H s. 12 g of compound 3 and 7.99 g of N-bromosuccinimide (NBS) are added to 240 ml of chloroform. The mixture is cooled to −15° C. and then 0.074 g of 60% perchloric acid in water are added and the reaction mixture is stirred for 40 minutes at −15° C. Then the chloroform solution is washed with water, dried over MgSO$_4$ and then the solvent is evaporated. The product is recrystallized from dichloromethane and then from isopropanol to give a compound of formula 4. $^1$H-NMR data (ppm, CDCl$_3$): 8.69 2H d, 7.24 2H d, 3.97 4H t, 1.76-1.65 4H m, 0.60 4H m, 0.01 18H s.

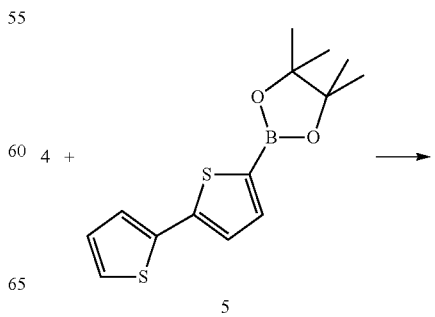

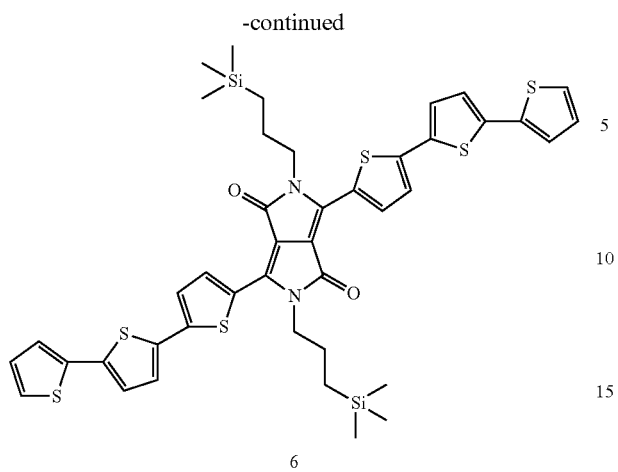

6

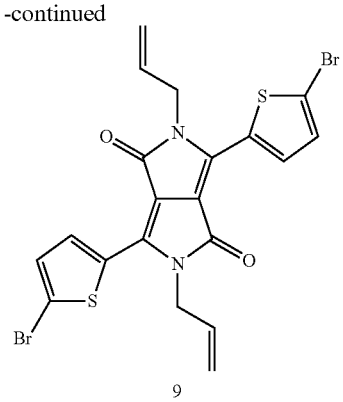

9 b) 1 g of compound 4, 0.89 g of compound 5 [479719-88-5], 0.8 mg of Pd(II)acetate and 4.9 mg of 2-(di-tert-butylphosphine)-1-phenylindole are added into a reactor under Argon. Then 12 ml of degassed tetrahydrofuran are added under argon and the mixture is heated to 60° C. Then 367 mg of lithiumhydroxide-monohydrate are added and the reaction mixture is heated for two hours under reflux. The mixture is poured on methanol and is filtered. The filter cake is then purified by chromatography over silica gel to give a compound of formula 6. $^1$H-NMR data (ppm, CDCl$_3$): 8.97 2H d, 7.32 2H d, 7.28-7.22 6H m, 7.14 2H d, 7.06 2H dxd, 4.09 4H t, 1.88-1.72 4H m, 0.66 4H m, 0.03 18H s.

Example 2

Synthesis of Compound 11 (I-1)

a) 5 g of compound 1 [850583-75-4] and 7.04 g of potassium carbonate are dispersed in 50 ml of dry dimethylformamide. The mixture is heated to 65° C. and then 6.04 g of allylbromide 7 [106-95-6] are added and the reaction mixture is stirred over night at 65° C. The reaction mixture is cooled to room temperature and then poured on water. The product is extracted with dichloromethane. The organic phase is dried over MgSO$_4$ and the solvent is evaporated. The product is purified by recrystallization to give a compound of formula 8. $^1$H-NMR data (ppm, CDCl$_3$): 8.80 2H d, 7.65 2H d, 7.27 2H dxd, 6.07-5.98 2H m, 5.25 2H s, 5.21 2H d, 4.77-4.75 4H m. Compound 8 and two equivalents of N-bromo-succinimide (NBS) are added to chloroform. The mixture is cooled to −15° C. and then a drop of 60% perchloric acid in water is added and the reaction mixture is stirred for 2 hours at −15° C. Then the chloroform solution is washed with water, dried over MgSO$_4$ and then the solvent is evaporated. The product is purified by recrystallization to give a compound of formula 9.

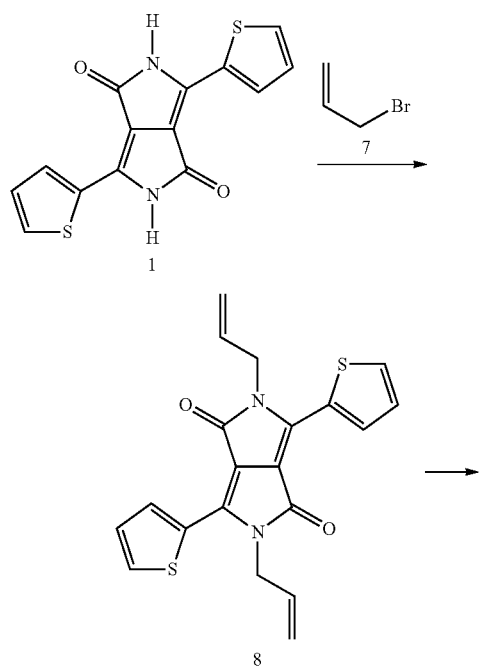

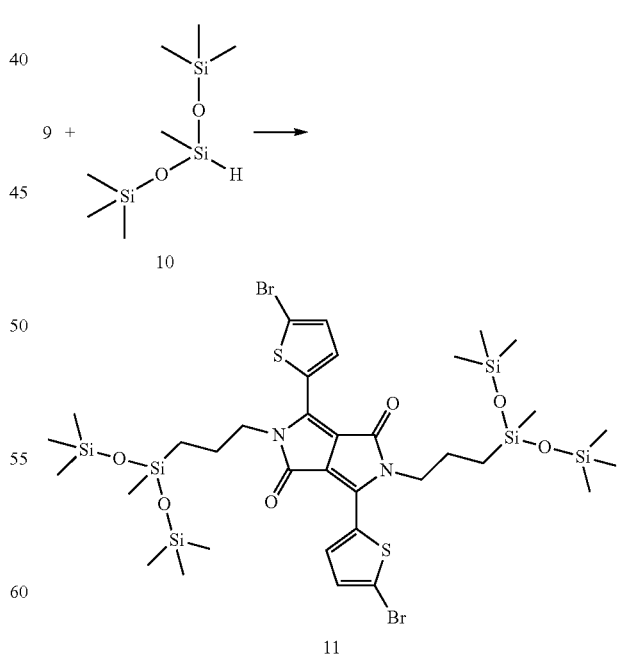

b) Compound 9 and two equivalents of 1,1,1,3,5,5,5-heptamethyltrisiloxane 10 are added to toluene. Then Karstedt catalyst is added and the mixture is stirred at 50° C. The solvent is evaporated under reduced pressure and the product is purified by chromatography over silica gel to give a compound of formula 11.

Alternatively compound 11 can be obtained from compound 12 by bromination with NBS.

Example 3

Synthesis of Compound 12 (B-3)

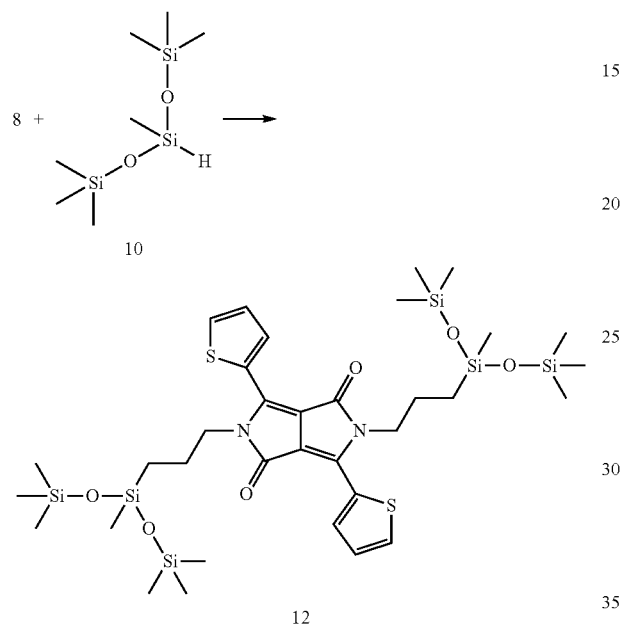

Compound 8 and two equivalents of 1,1,1,3,5,5,5-heptamethyltrisiloxane 10 are added to toluene. Then Karstedt catalyst (compound of platinum(0) and divinyltetramethyldisiloxane) is added and the mixture is stirred at 50° C. The solvent is evaporated under reduced pressure and the product is purified by chromatography over silica gel to give a compound of formula 12. $^1$H-NMR data (ppm, CDCl$_3$): 8.92 2H d, 7.62 2H d, 7.28 2H dxd, 4.06 4H t, 1.77 4H txt, 0.59 4H t, 0.07 36H s, 0.05 6H s.

Example 4

Synthesis of Compound 16 (I-6)

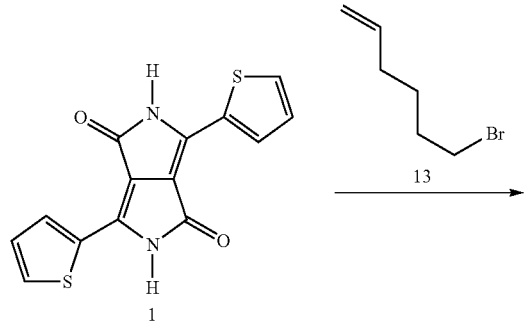

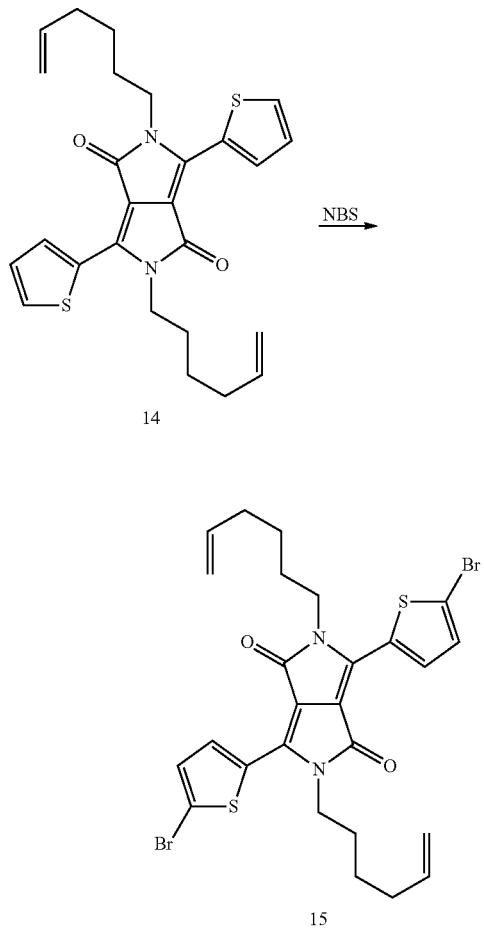

a) Compound 15 is synthesized in analogy to compound 9.

15 ⟶

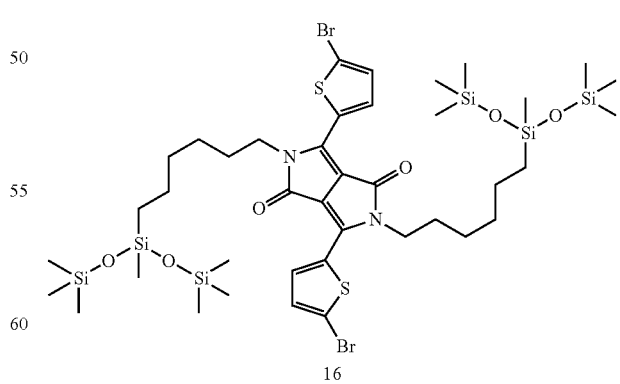

b) Compound 16 is synthesized in analogy to compound 11.

Alternatively compound 16 can be obtained from compound 17 by bromination with NBS.

Example 5
Synthesis of Compound 17 (B-5)
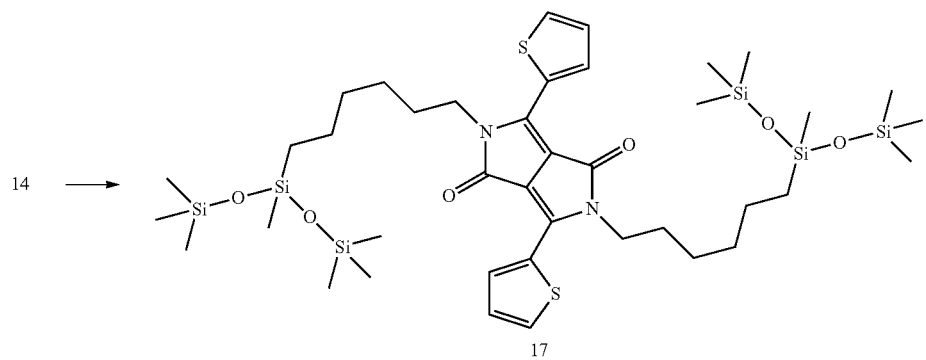
Compound 17 is synthesized in analogy to compound 12.
Example 6
Synthesis of Polymer 19 (P-6)
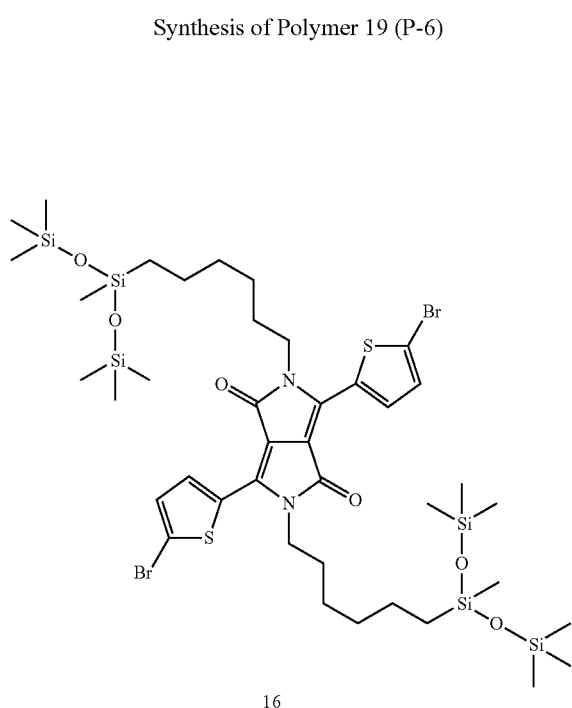
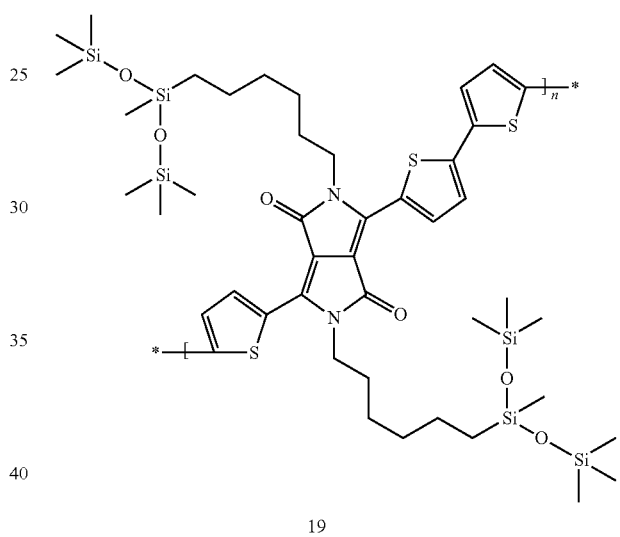
Polymer 19 is obtained by reaction of compound 16 with one equivalent of compound 18 [145483-63-2] under Stille coupling reaction conditions.
Example 7
Synthesis of Polymer 26 (P-7)
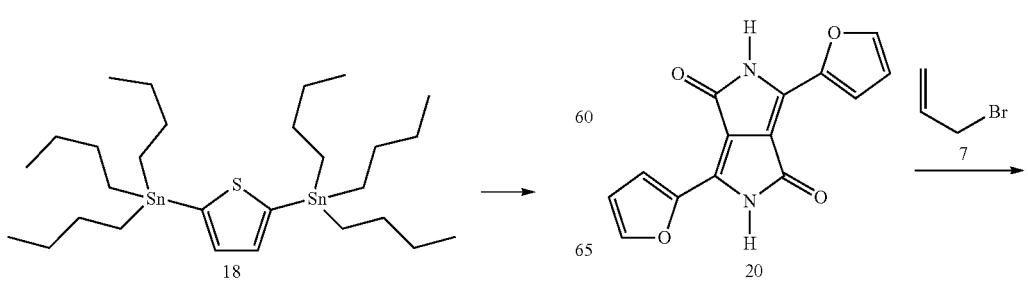

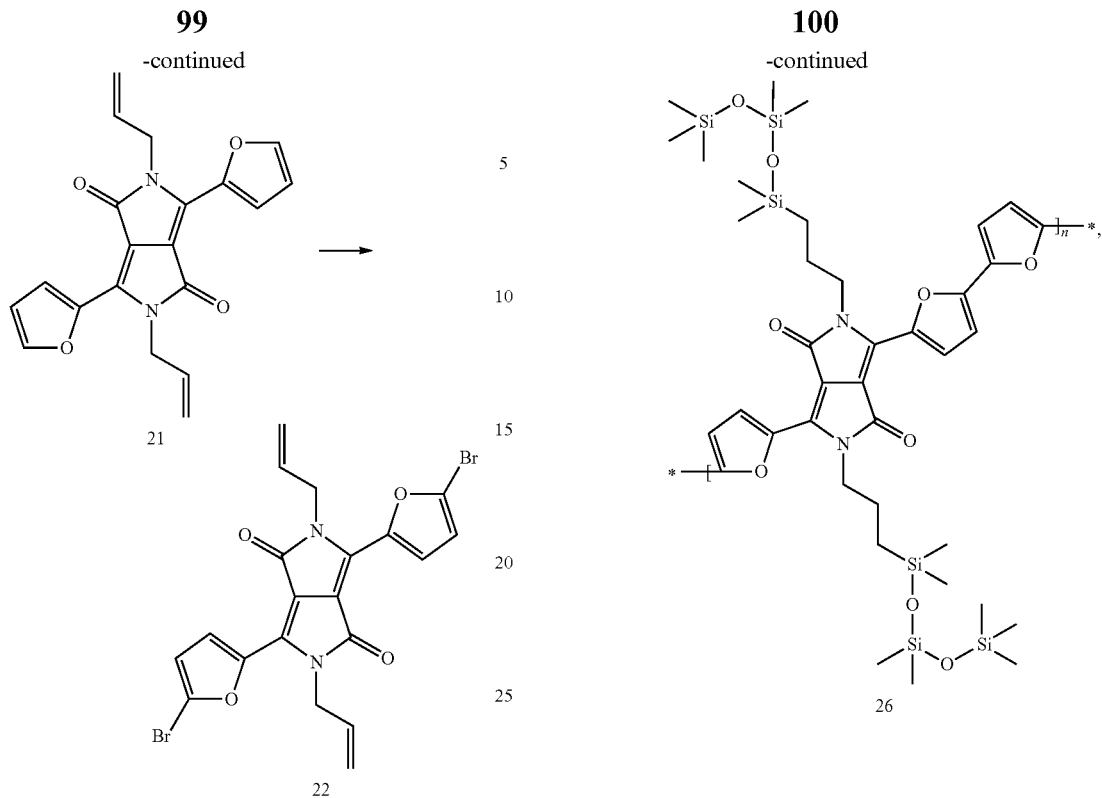
a) Compound 22 is synthesized starting from compound 20 [88949-34-2] in analogy to compound 9 in Example 2.
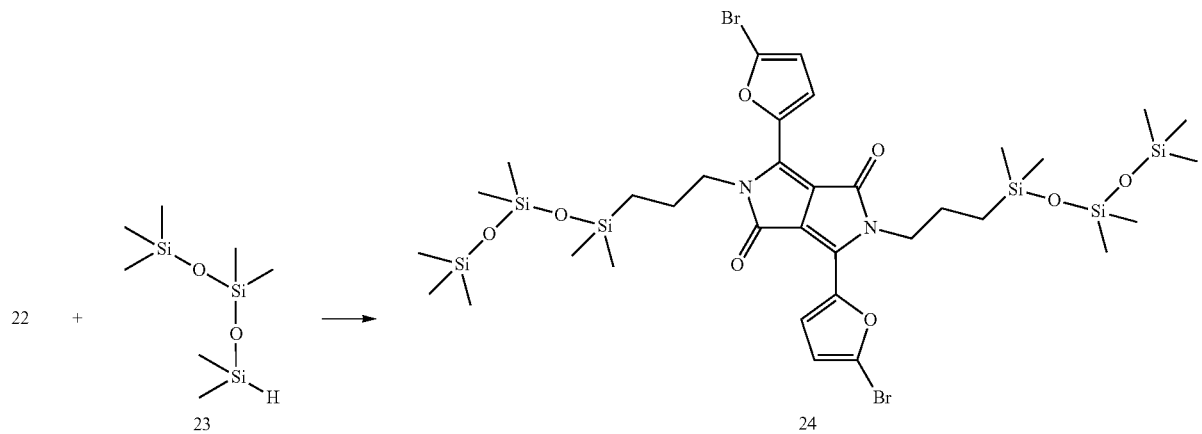
b) Compound 24 is synthesized starting from compound 22 and compound 23 [2895-07-0] in analogy to compound 11 in Example 2.
c) Compound 26 is synthesized starting from compound 24 and compound 25 [476004-83-8] in analogy to compound 12 in Example 8 of WO2011/144566.
Example 8
Synthesis of Compound 31 (I-9)
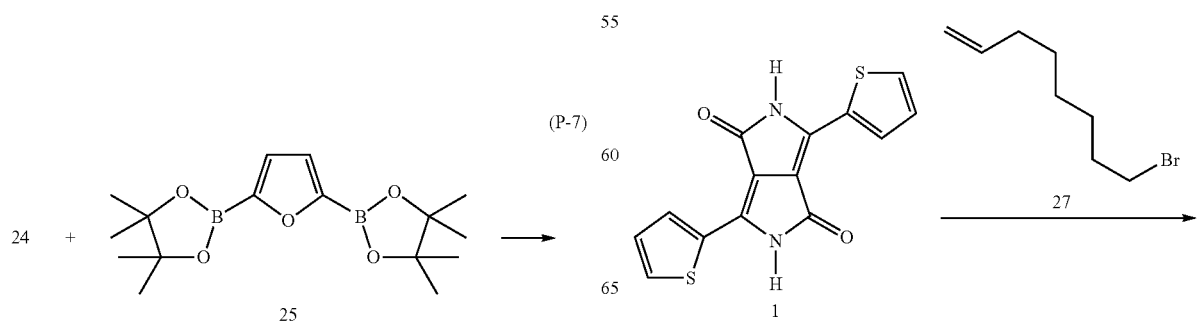

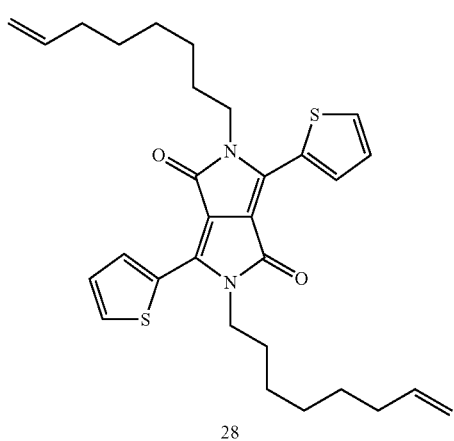

28

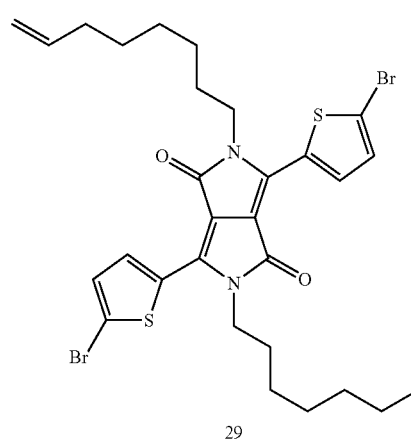

29 a) Compound 28 is obtained from compound 1 and 8-bromo-1-octene 27 in analogy to compound 8 and is purified by column chromatography. $^1$H-NMR data (ppm, CDCl$_3$): 8.93 2H d, 7.65 2H d, 7.30 2H dxd, 5.88-5.74 2H m, 5.04-4.92 4H m, 4.09 4H t, 2.05 4H txt, 1.75 4H txt, 1.44-1.22 12H m.

b) Compound 29 is obtained from compound 28 in analogy to compound 9 and is purified by column chromatography. $^1$H-NMR data (ppm, CDCb): 8.68 2H d, 7.26 2H d, 5.88-5.75 2H m, 5.05-4.93 4H m, 4.03 4H t, 2.05 4H txt, 1.72 4H txt, 1.46-1.27 12H m.

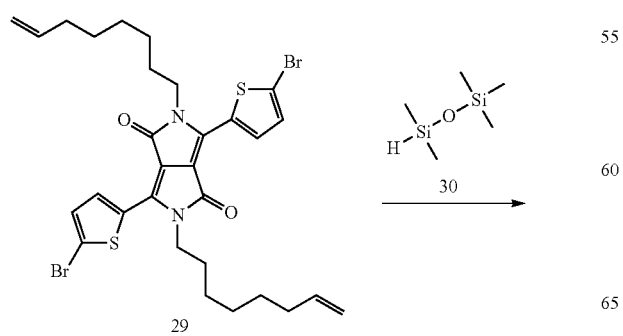

29

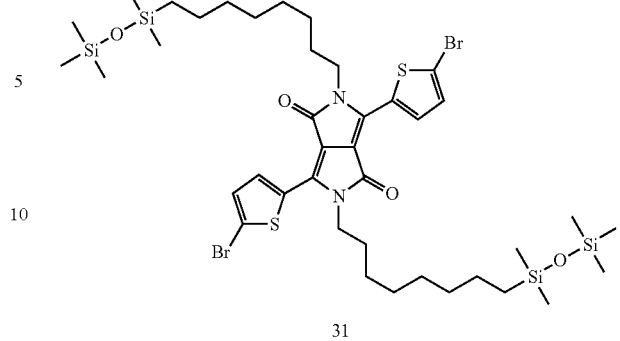

31 c) 3.6 g of compound 29 and 3.15 g of pentamethyldisiloxane 30 are added to 40 ml toluene under argon. Then 5 mmol Karstedt catalyst in toluene is added (20 drops) and the mixture is stirred at reflux overnight. The solvent is evaporated under reduced pressure and the product is purified by chromatography over silica gel to give a compound of formula 31. $^1$H-NMR data (ppm, CDCb): 8.69 2H d, 7.25 2H d, 4.00 4H t, 1.74 4H txt, 1.50-1.25 20H m, 0.51 4H t, 0.07 18H s, 0.05 12H s.

Example 9

Synthesis of Compound 32 (I-8)

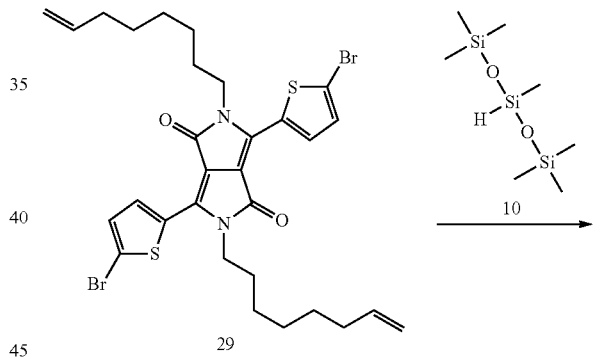

32

Compound 32 is obtained from compound 29 and 1,1,1,3,5,5,5-heptamethyltrisiloxane 10 in analogy to compound 31.

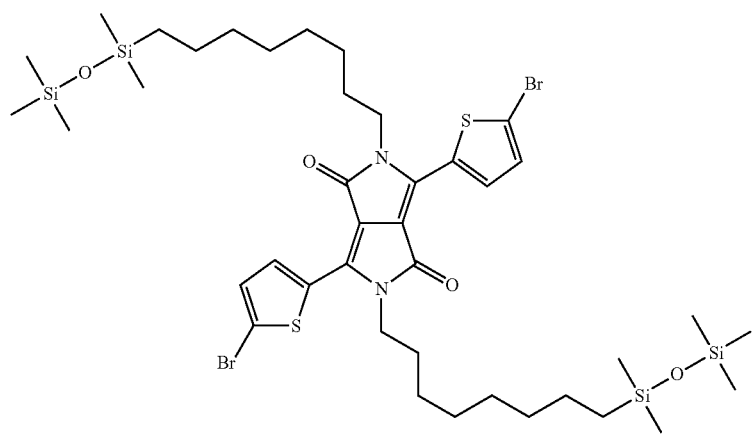

31

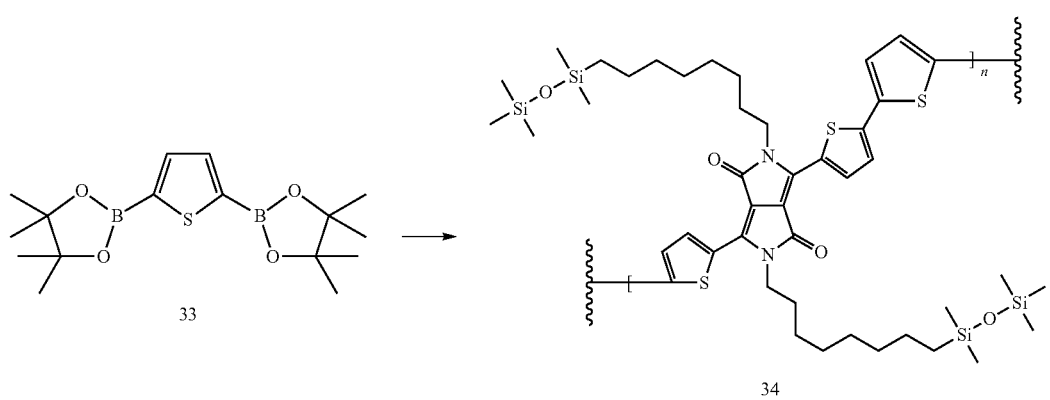

33

34

Example 10

Synthesis of Polymer 34 (P-10)

400 mg of compound 31 and 137.8 mg of thiophene-diboronicacidpinacolester 33 are dissolved together with 3.7 mg palladium(II)acetate and 22.1 mg of 2-(di-tert-butylphosphino)-1-phenylindole [740815-37-6] in 25 ml of degassed tetrahydrofurane under argon. The whole mixture is refluxed for 30 minutes and then 103.2 mg of LiOH-monohydrate is added. The reaction mixture is then refluxed 1.5 hours under argon. The reaction mixture is poured on water, precipitated and filtered. The crude polymer is then dissolved in chloroform and the organic phase is refluxed together with a 1% water solution of NaCN during 1 hour. The phases are separated and the organic phase is still washed 3 times with water. Then the polymer is precipitated out of the chloroform solution with methanol. The crude polymer is then fractionated by Soxhlet extraction with heptane, tetrahydrofurane and chloroform. The chloroform fraction contained 230 mg of the desired polymer. Mw 7'900, polydispersity 1.17 (measured by high temperature GPC at 150° C. with trichlorobenzene).

Example 11

Synthesis of Polymer 35 (P-8)

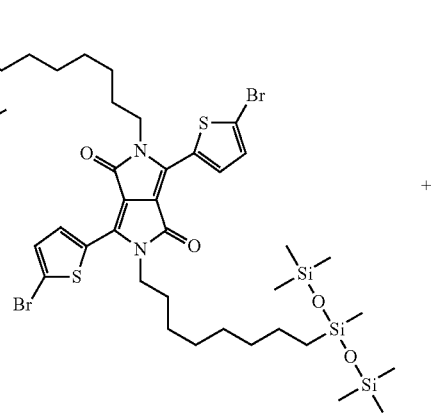

32

105
-continued
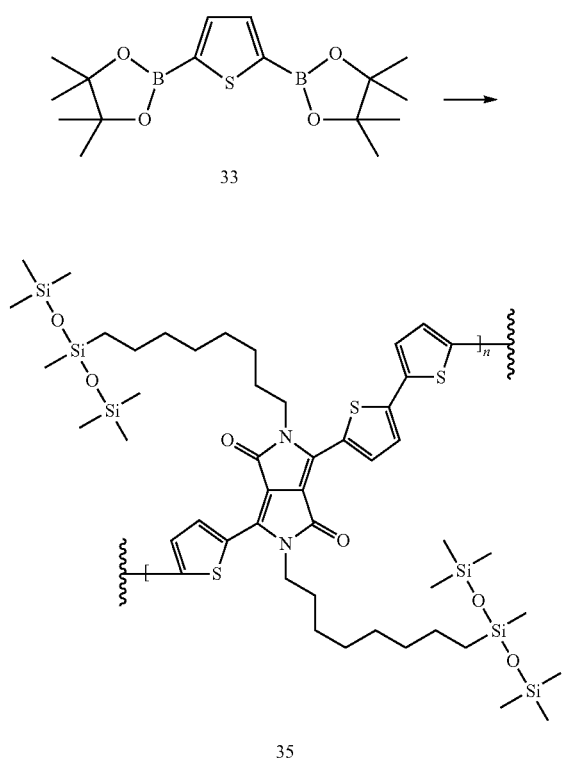
Compound 35 is obtained from compound 32 and compound 33 in analogy to compound 34.
106
Example 12
Synthesis of Compound 36 (B-20)
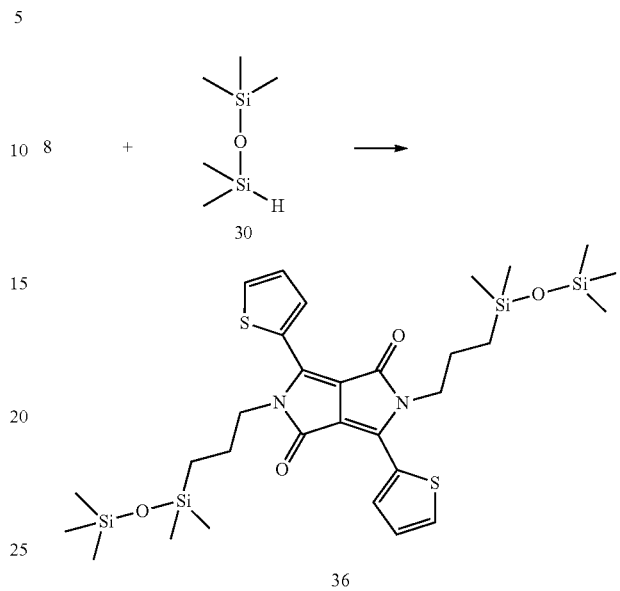
Compound 36 is obtained in analogy to compound 12 from compound 8 and pentamethyldisiloxane 30. $^1$H-NMR data (ppm, CDCl$_3$): $^1$H-NMR data (ppm, CDCl$_3$): 8.93 2H d, 7.64 2H d, 7.30 2H dxd, 4.08 4H t, 1.79 4H txt, 0.63 4H t, 0.09 18H s, 0.07 12H s.
Example 13
Synthesis of Compound 37 (I-10)
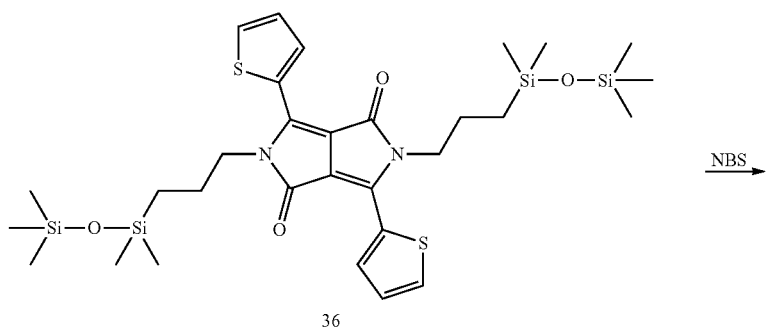
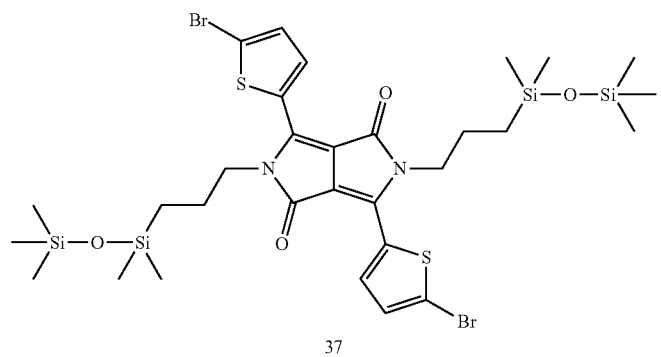

1 g of compound 36 is dissolved in 10 ml of chloroform. Then 550 mg of N-bromosuccinimid (NBS) are added and the reaction mixture is stirred at room temperature overnight. The solvent is evaporated under reduced pressure and the product is chromatographed over silica gel to get compound 37. $^1$H-NMR data (ppm, CDCl$_3$): $^1$H-NMR data (ppm, CDCl$_3$): 8.69 2H d, 7.26 2H d, 3.98 4H t, 1.75 4H txt, 0.63 4H t, 0.09 18H s, 0.07 12H s;

Example 14

Synthesis of Compound 41 (B-18)

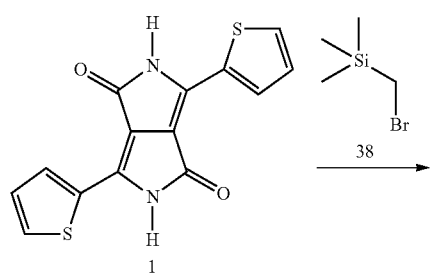

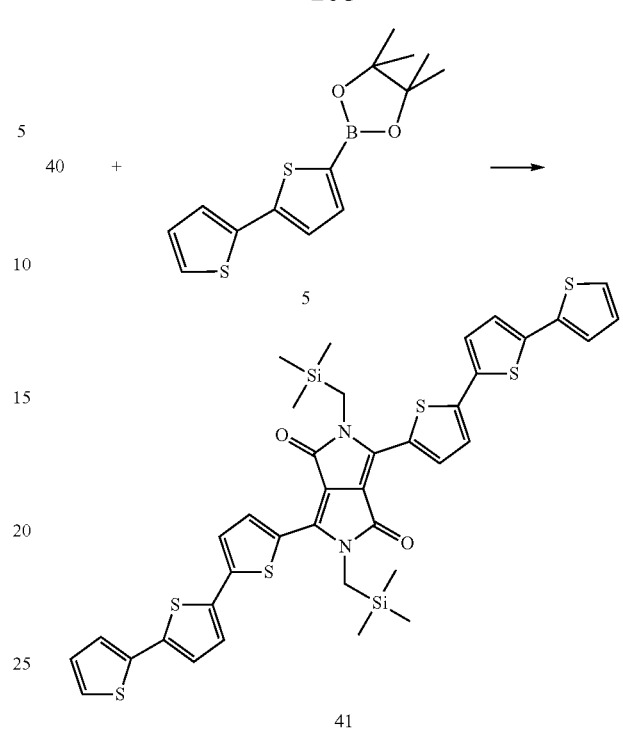

c) Compound 41 is obtained from compound 40 and [479719-88-5]5 in analogy to compound 6. $^1$H-NMR data (ppm, CDCb): 8.93 2H d, 7.33 2H d, 7.31-7.24 6H m, 7.15 2H d, 7.07 2H dxd, 3.78 4H s, 0.15 18H s.

Example 15

Synthesis of Compound 45 (B-21)

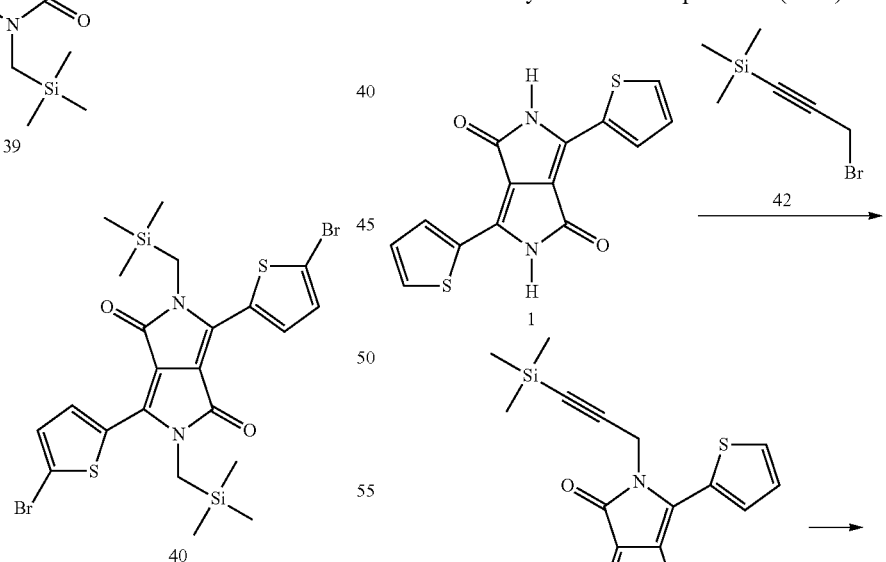

a) Compound 39 is obtained from compound 1 and bromo-methyl-trimethylsilane 38 in analogy to compound 3. $^1$H-NMR data (ppm, CDCb): 8.88 2H d, 7.62 2H d, 7.30 2H dxd, 3.76 4H s, 0.09 18H s.

b) Compound 40 is obtained from compound 39 in analogy to compound 4. $^1$H-NMR data (ppm, CDCb): 8.64 2H d, 7.25 2H d, 3.64 4H s, 0.11 18H s.

-continued

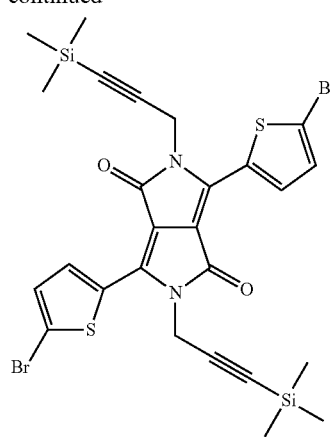

44 a) Compound 43 is obtained from compound 1 and bromo-methyl-trimethylsilane 42 in analogy to compound 3. $^1$H-NMR data (ppm, CDCl$_3$): 8.74 2H d, 7.72 2H d, 7.31 2H dxd, 4.86 4H s, 0.11 18H s.

b) Compound 44 is obtained from compound 43 in analogy to compound 4. $^1$H-NMR data (ppm, CDCl$_3$): 8.46 2H d, 7.25 2H d, 4.77 4H s, 0.13 18H s.

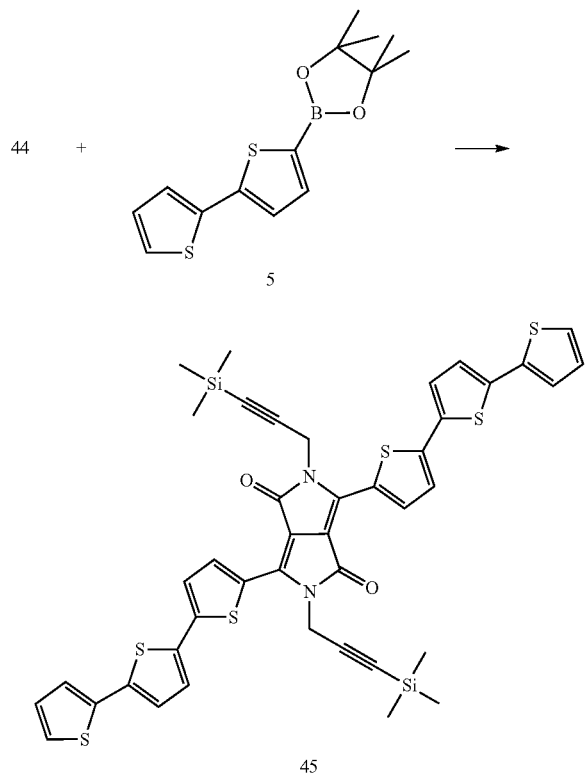

45 c) Compound 45 is obtained from compound 44 and [479719-88-5]5 in analogy to compound 6. $^1$H-NMR data (ppm, CDCl$_3$): 8.73 2H d, 7.34 2H d, 7.31-7.24 6H m, 7.16 2H d, 7.09 2H dxd, 4.88 4H s, 0.15 18H s.

Application Example 1

Application of the Semiconducting Compound 6

The semiconductor thin film is prepared by spin-coating the compound of the formula 6 obtained in example 1 in a 0.5% (w/w) solution in chloroform. The spin coating is accomplished at a spinning speed of 3000 rpm (rounds per minute) for about 20 seconds in ambient conditions. The devices are evaluated as deposited and after being annealed at 100° C. for 15 minutes.

Transistor Performance

The transistor behavior is measured on an automated transistor prober (TP-10, CSEM Zü-rich) and showed clear transistor behavior.

Application Example 2

Photovoltaic Application of the Semiconducting Compound 6

The solar cell has the following structure: Al electrode/LiF layer/organic layer, including compound of the invention/ [poly(3,4-ethylenedioxy-thiophene) (PEDOT)/poly(styrene-sulfonic acid) (PSS)]/ITO electrode/glass substrate. The solar cells are made by spin coating a layer of the PEDOT-PSS on a pre-patterned ITO on glass substrate. Then a 1:1 mixture of the compound of formula 6 (1% by weight): [70]PCBM (a substituted C$_{70}$ fullerene) is spin coated (organic layer). LiF and Al are sublimed under high vacuum through a shadow-mask.

Solar Cell Performance

The solar cell is measured under a solar light simulator. Then with the External Quantum Efficiency (EQE) graph the current is estimated under AM1.5 conditions.

Application Example 1

(Bottom-Gate Bottom Contact (BGBC) Field Effect Transistor (FET))

Semiconductor Film Deposition:

Siliconwafers (Si n−(425±40 µm)) with a 230 nm thick SiO$_2$ dielectric and patterned indium tin oxide (15 nm)/gold (30 nm) contacts (L=20, 10, 5, 2.5 µm, W=0.01 m; Fraunhofer IPMS (Dresden)) are prepared by standard cleaning by washing with acetone and i-propanol followed by oxygen plasma treatment for 30 minutes.

The substrates are transferred in a glove box. An octyl-trichlorsilane (OTS) monolayer is grown on the dielectric surface by putting the substrates in a 50 mM solution of octyltri-chlorosilane (OTS) in trichloroethylene for 1 h. After monolayer growth, the substrates are washed with toluene to remove physisorbed silane.

The semiconductor P-10 is dissolved in CHCb in a concentration 0.75% by weight at 80° C. and spin-coated at 1500 rpms for 60 s onto the substrates.

Application Example 4

Top Gate Bottom Contact (TGBC) FET

Substrate Preparation:

For TGBC FETs PET substrates with lithographically patterned 50 nm gold (Au) contacts covered with photoresist are used. Substrates are prepared by standard cleaning in acetone and ethanol and dried at 60° C. for 30 min.

Transistor Preparation:

The semiconductor P-10 is dissolved in trichloroethylene (0.75 wt %) at 80° C. for 4 h., filtered through a 0.45μ filter, spun to achieve a 50 nm layer and dried for 30 s at 80° C. Immediately after 500 nm layer of dielectric (CYTOP) has been spin-coated and dried for 2 minutes at 80° C. 120 nm gold is evaporated through a shadow mask as gate contact.

BGBC and TGBC OFET Measurement:

OFET transfer and output characteristics are measured on an Agilent 4155C semiconductor parameter analyzer. The devices are annealed in a glovebox at 150° C. for 15 minutes before the measurements are done in a glove box under a nitrogen atmosphere at room temperature. For p-type transistors the gate voltage ($V_g$) varies from 10 to −30 V and at drain voltage ($V_d$) equal to −3 and −30V for the transfer characterisation. For the output characterization $V_d$ is varied from 0 to −30V at $V_g$=0, −10, −20, −30 V.

The results of BGBC and TGBC FET measurements are reported in the Table below:

| Appl. Example | Semi-conductor | Solvent | Mobility, cm²/Vs | On/off |
|---|---|---|---|---|
| 3 | P-10 | CHCl₃ | 1.40E−01 | 3.80E+06 |
| 4 | P-10 | CH₃CCl₃ | 0.11 | 3.00E+04 |

The invention claimed is:
1. A polymer comprising a repeating unit of the formula

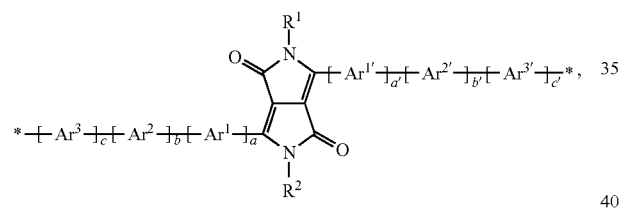

(I)

wherein
a is 0, 1, 2, or 3, a' is 0, 1, 2, or 3; b is 0, 1, 2, or 3; b' is 0, 1, 2, or 3; c is 0, 1, 2, or 3; c' is 0, 1, 2, or 3;
$R^1$ and $R^2$ may be the same or different and are selected from the group consisting of a $C_1$-$C_{100}$alkyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —NR$^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$,
a $C_2$-$C_{100}$alkenyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —NR$^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$,
a $C_3$-$C_{100}$alkinyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —NR$^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$,
a $C_3$-$C_{12}$cycloalkyl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —NR$^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$,
a $C_6$-$C_{24}$aryl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$;
a $C_2$-$C_{20}$heteroaryl group, which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and
—CO—$C_1$-$C_{18}$alkyl, —CO—$C_5$-$C_{12}$cycloalkyl, —COO—$C_1$-$C_{18}$alkyl which can optionally be substituted one or more times with $C_1$-$C_{12}$alkyl, $C_1$-$C_{12}$alkoxy, halogen, $C_5$-$C_{12}$cycloalkyl, nitro, cyano, vinyl, allyl, $C_6$-$C_{24}$aryl, $C_2$-$C_{20}$heteroaryl, or $E^{Si}$; and/or can optionally be interrupted by —O—, —S—, —NR$^{39}$—, —COO—, —CO—, —OCO—, $C_6$-$C_{24}$arylene, $C_2$-$C_{20}$heteroarylene, $C_3$-$C_{12}$cycloalkylene, or $D^{Si}$; wherein
$E^{Si}$ is —SiR$^{161}$R$^{162}$R$^{163}$ or —O—SiR$^{161}$R$^{162}$R$^{163}$,
$D^{Si}$ is —SiR$^{161}$R$^{162}$—, —SiR$^{161}$R$^{162}$—(O—SiR$^{161}$R$^{162}$)$_d$— or —O—SiR$^{161}$R$^{162}$—,
$R^{161}$, $R^{162}$ and $R^{163}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, —O—SiR$^{164}$R$^{165}$R$^{166}$, —(O—SiR$^{164}$R$^{165}$)$_d$—R$^{166}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;
$R^{164}$, $R^{165}$ and $R^{166}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, —O—SiR$^{169}$R$^{170}$R$^{171}$, —(O—SiR$^{169}$R$^{170}$)$_d$—R$^{171}$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;
$R^{169}$, $R^{170}$ and $R^{171}$ are independently of each other hydrogen, $C_1$-$C_{25}$alkyl, $C_3$-$C_{12}$cycloalkyl, which might optionally be substituted with $C_1$-$C_4$alkyl, $C_1$-$C_{25}$haloalkyl, $C_2$-$C_{25}$alkenyl, —O—Si(CH$_3$)$_3$, $C_1$-$C_{25}$alkoxy, $C_3$-$C_{24}$(hetero)aryloxy, NR$^{167}$R$^{168}$, halogen, $C_1$-$C_{25}$acyloxy, phenyl, phenyl which is substituted 1 to 3 times by $C_1$-$C_{24}$alkyl, halogen, cyano or $C_1$-$C_{25}$alkoxy;
$R^{167}$ and $R^{168}$ are independently of each other hydrogen, $C_6$-$C_{18}$aryl, $C_6$-$C_{18}$aryl which is substituted by $C_1$-$C_{18}$alkyl, or $C_1$-$C_{18}$alkoxy, or $C_1$-$C_{25}$alkyl, which may optionally be interrupted by one or more oxygen or sulphur atoms, or $C_7$-$C_{25}$arylalkyl;
d is an integer from 1 to 50;
$R^{39}$ is hydrogen, $C_1$-$C_{18}$alkyl, $C_1$-$C_{18}$haloalkyl, $C_7$-$C_{25}$arylalkyl, or $C_1$-$C_{18}$alkanoyl,
Ar$^1$, Ar$^{1'}$, Ar$^2$, Ar$^{2'}$, Ar$^3$ and Ar$^{3'}$ are independently of each other

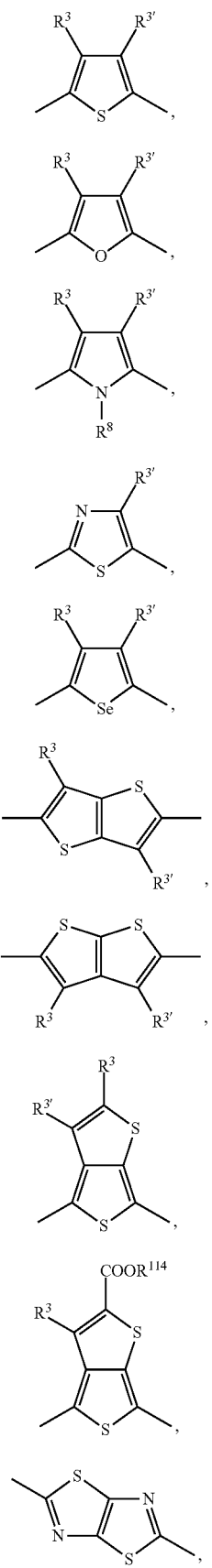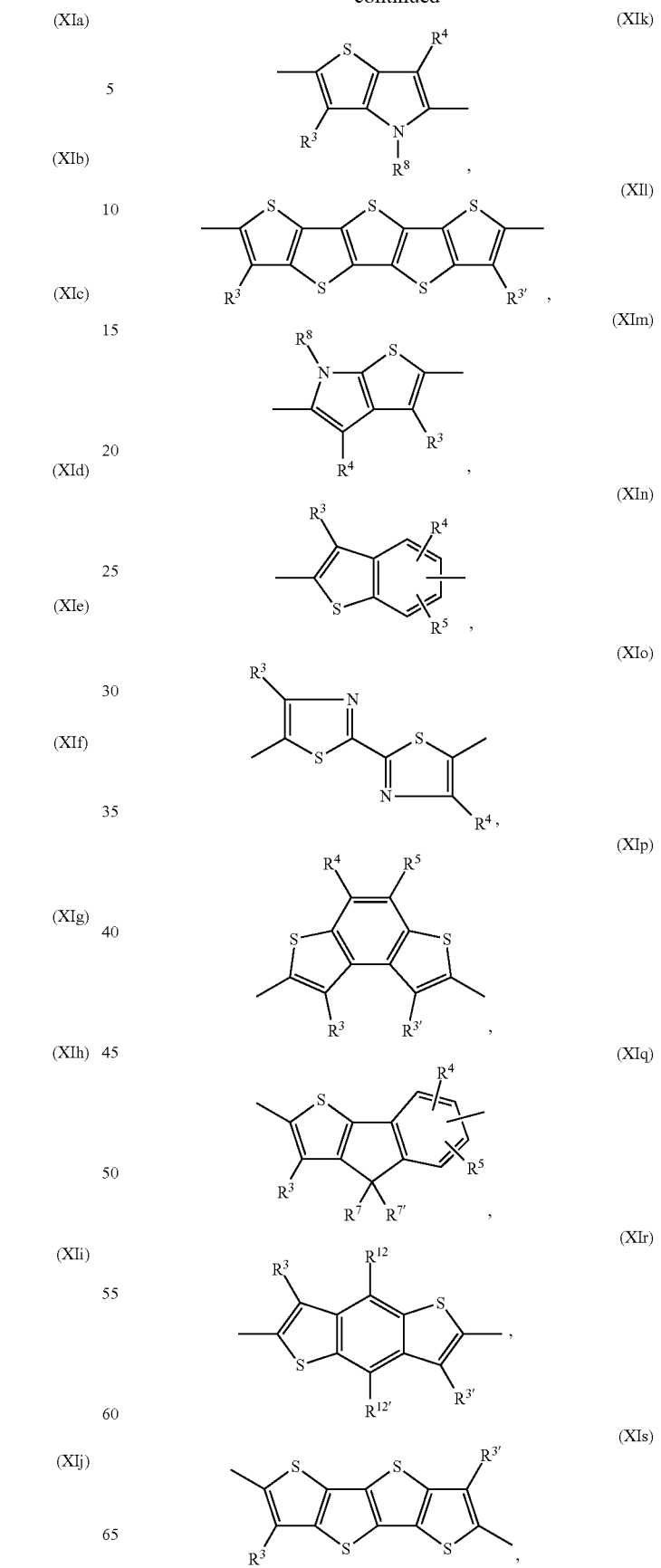

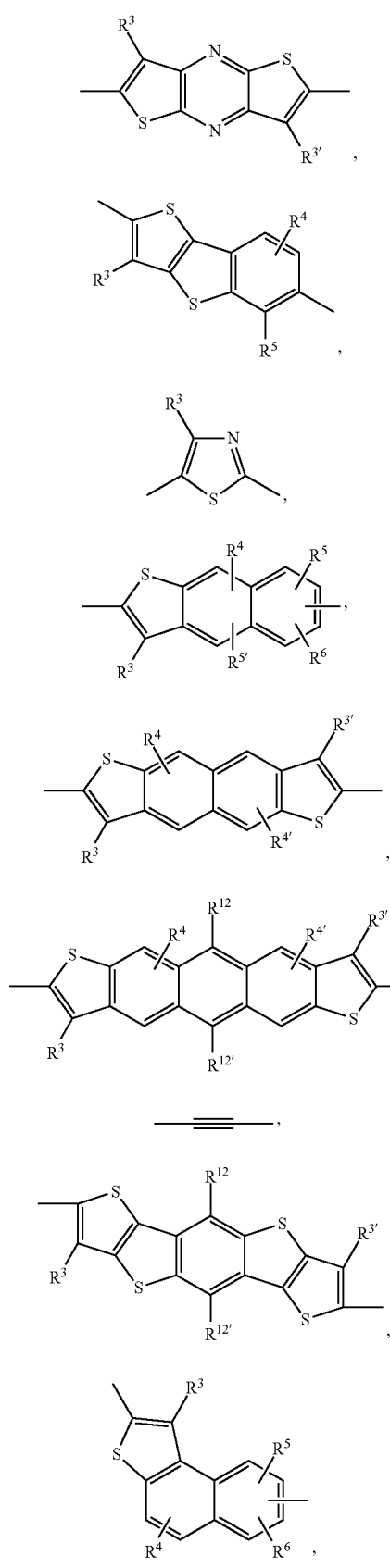
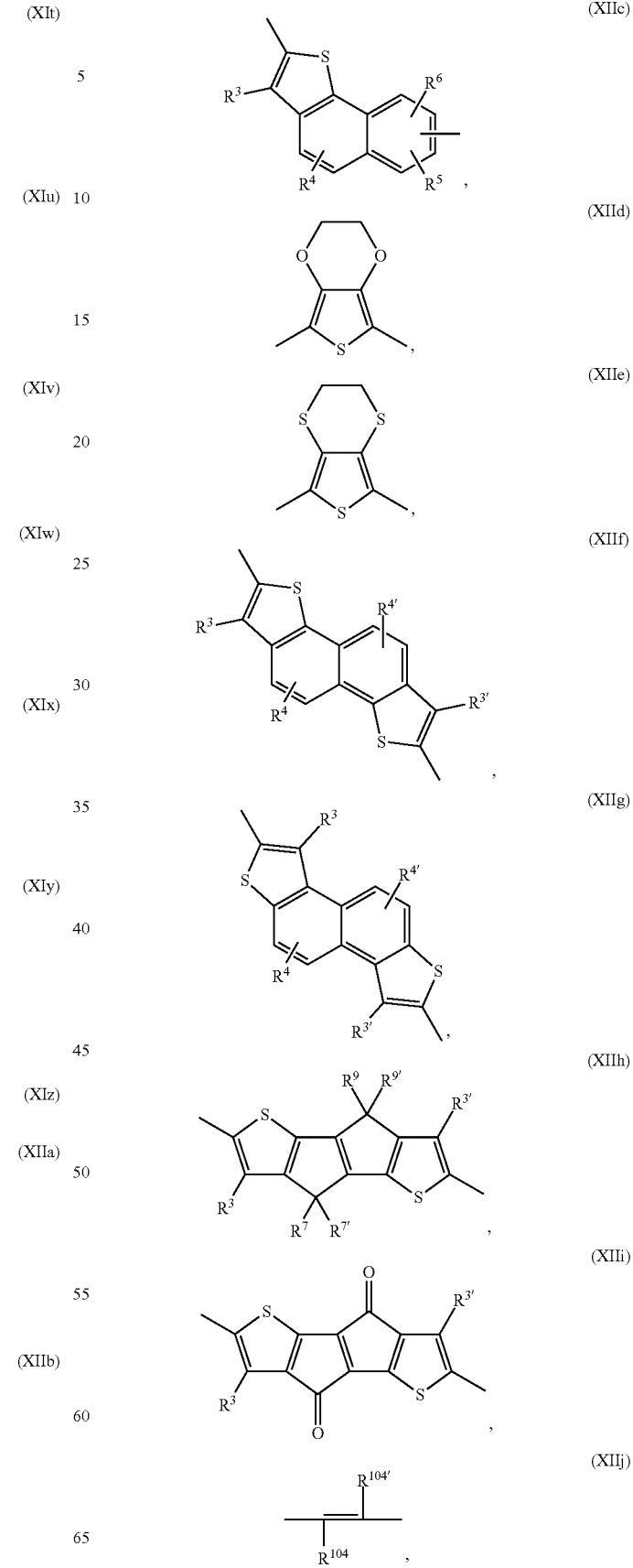

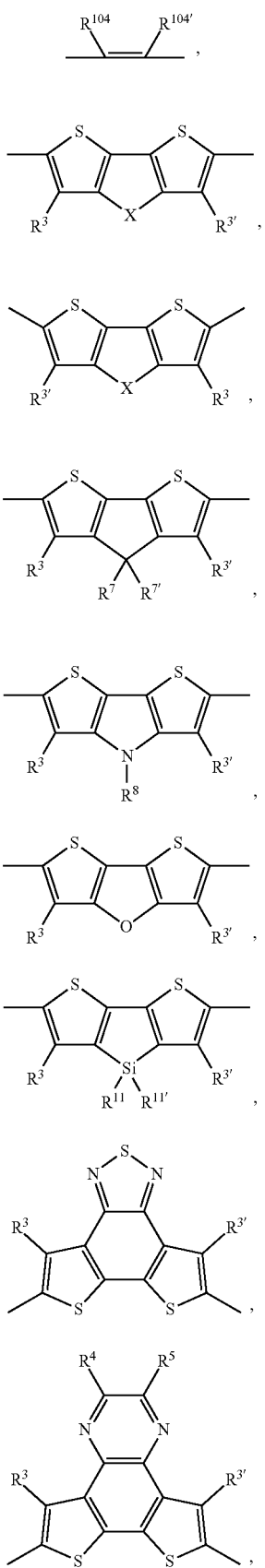
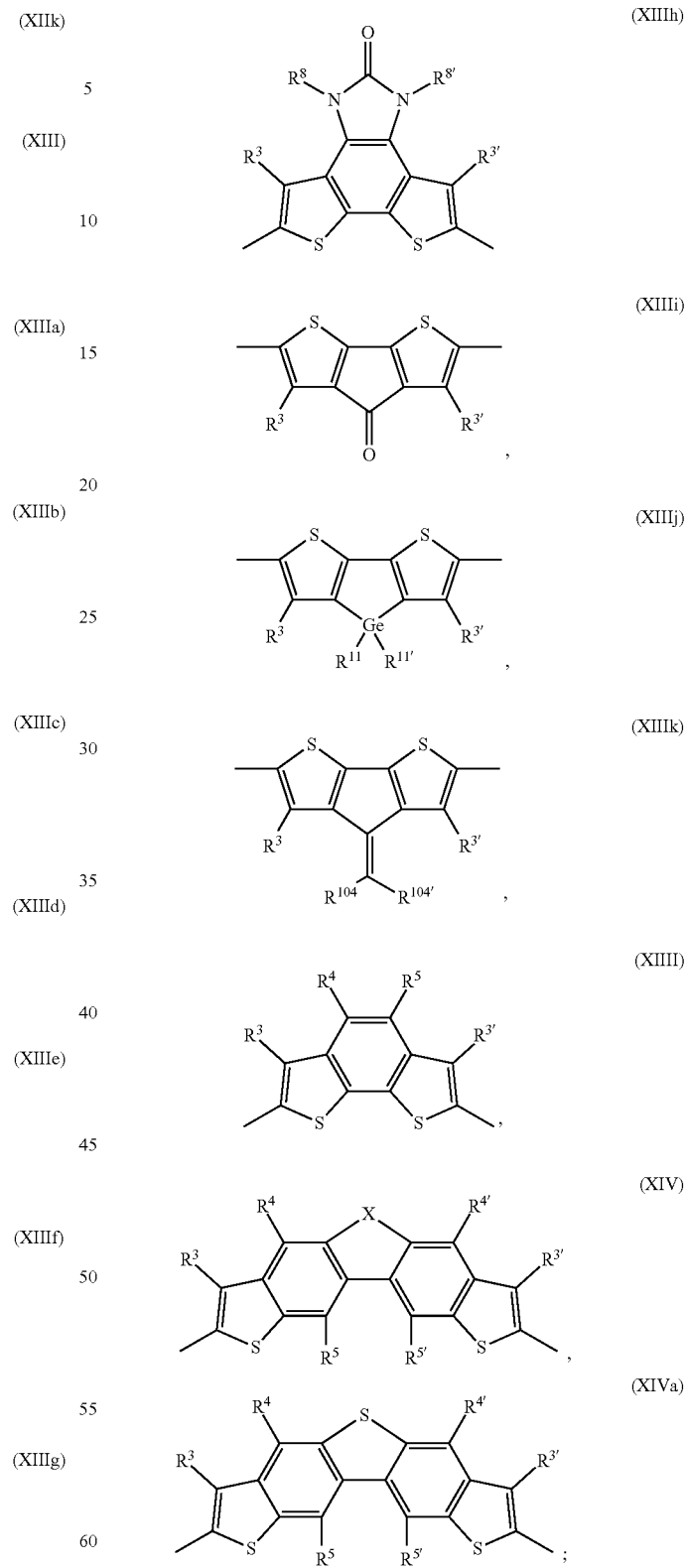
wherein
X is —O—, —S—, —NR$^8$—, —Si(R$^{11}$)(R$^{11'}$)—, —Ge(R$^{11}$)(R$^{11'}$)—, —C(R$^7$)(R$^{7'}$)—, —C(=O)—, —C(=CR$^{104}$R$^{104'}$)—,

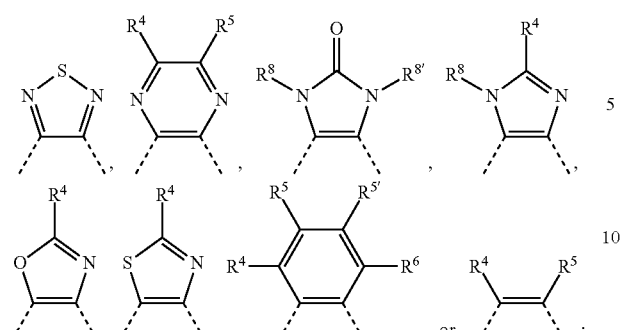

R³ and R³' are independently of each other hydrogen, halogen, $E^{Si}$, halogenated $C_1$-$C_{25}$alkyl, cyano, $C_1$-$C_{25}$alkyl, which may optionally be interrupted by one or more oxygen or sulphur atoms, $C_7$-$C_{25}$arylalkyl, $C_1$-$C_{25}$alkyl substituted with one or more $E^{Si}$, or $C_1$-$C_{25}$alkoxy;

R⁴, R⁴', R⁵, R⁵', R⁶, and R⁶' are independently of each other hydrogen, halogen, $E^{Si}$, halogenated $C_1$-$C_{25}$alkyl, cyano, $C_1$-$C_{25}$alkyl, which may optionally be interrupted by one or more oxygen or sulphur atoms, $C_7$-$C_{25}$arylalkyl, $C_1$-$C_{25}$alkyl substituted with one or more $E^{Si}$, or $C_1$-$C_{25}$alkoxy;

R⁷, R⁷', R⁹ and R⁹' are independently of each other hydrogen, $C_1$-$C_{25}$alkyl, which may optionally be interrupted by one, or more oxygen, or sulphur atoms, $C_1$-$C_{25}$alkyl substituted with one or more $E^{Si}$, or $C_7$-$C_{25}$arylalkyl, or R⁷ and R⁷', or R⁹ and R⁹' are together =CR¹⁰⁴R¹⁰⁴';

R⁸ and R⁸' are independently of each other hydrogen, $C_6$-$C_{18}$aryl; $C_6$-$C_{18}$aryl which is substituted by $C_1$-$C_{18}$alkyl, or $C_1$-$C_{18}$alkoxy, $C_1$-$C_{25}$alkyl, which may optionally be interrupted by one or more oxygen or sulphur atoms, $C_1$-$C_{25}$alkyl substituted with one or more $E^{Si}$, or $C_7$-$C_{25}$arylalkyl, R¹¹ and R¹¹' are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

R¹² and R¹²' are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or —≡—R¹³, wherein R¹³ is a $C_1$-$C_{10}$alkyl group, or a tri($C_1$-$C_8$alkyl)silyl group;

Ar¹, Ar¹', Ar², Ar²', Ar³ and Ar³' are independently of each other (XVa)
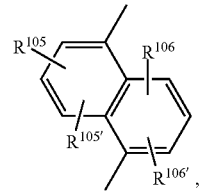

(XVb)
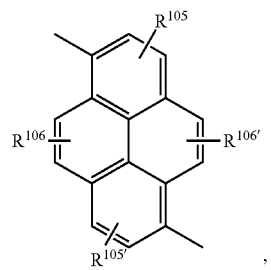

(XVc)
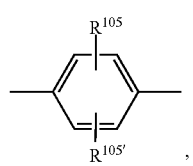

(XVd)
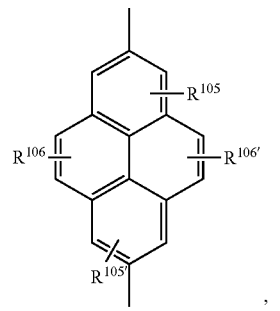

(XVe)
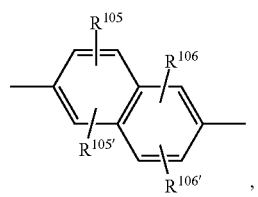

(XVf)
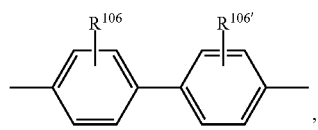

(XVg)
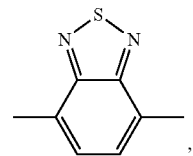

(XVh)
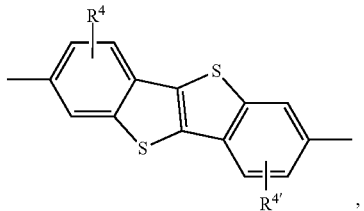

(XVI)
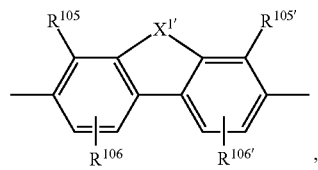

-continued

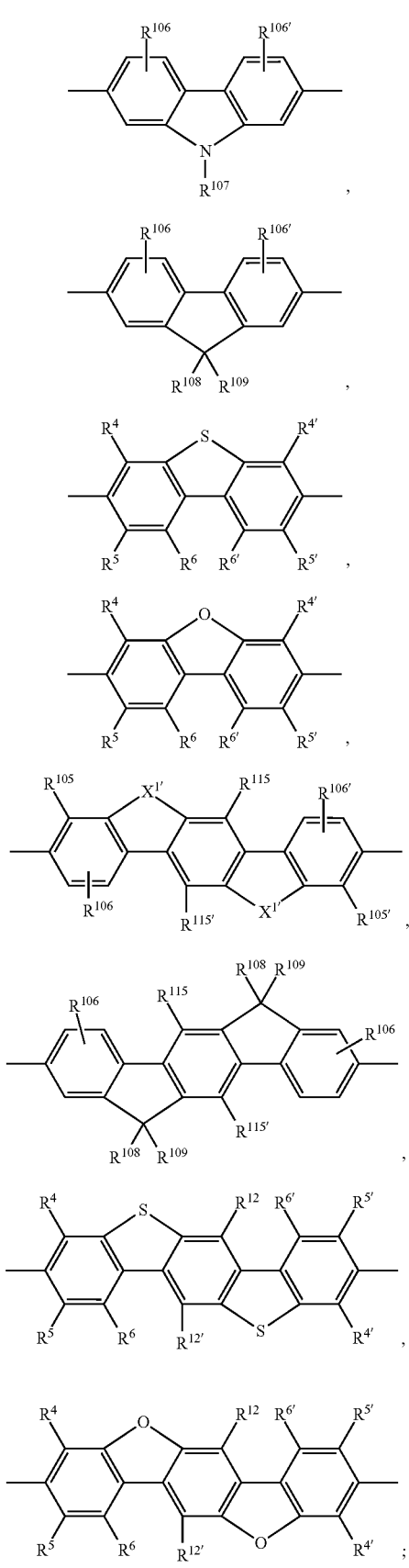

(XVIa)
(XVIb)
(XVIc)
(XVId)
(XVII)
(XVIIa)
(XVIIb)
(XVIIc)

wherein
$X^{1'}$ is S, O, $NR^{107}$—, —$Si(R^{117})(R^{117'})$—, —$Ge(R^{117})(R^{117'})$—, —$C(R^{108})(R^{109})$—, —C(=O)—, —$C(=CR^{104}R^{104'})$—,

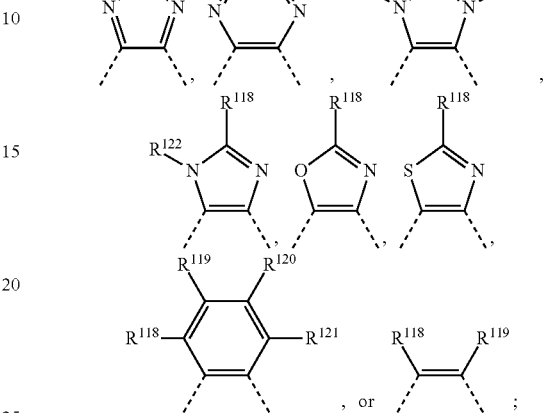

$R^{104}$ and $R^{104'}$ are independently of each other hydrogen, cyano, $COOR^{103}$, a $C_1$-$C_{25}$alkyl group, a $C_6$-$C_{24}$aryl or $C_2$-$C_{20}$heteroaryl;

$R^{103}$ is $C_1$-$C_{25}$alkyl, $C_1$-$C_{25}$alkyl, which may optionally be interrupted by one or more oxygen or sulphur atoms, or is $C_7$-$C_{25}$arylalkyl;

$R^{105}$, $R^{105'}$, $R^{106}$ and $R^{106'}$ are independently of each other hydrogen, halogen, cyano, $C_1$-$C_{25}$alkyl, which may optionally be interrupted by one or more oxygen or sulphur atoms, $C_7$-$C_{25}$arylalkyl, or $C_1$-$C_{18}$alkoxy, $R^{107}$ is hydrogen, $C_7$-$C_{25}$arylalkyl, $C_6$-$C_{18}$aryl, $C_6$-$C_{18}$aryl which is substituted by $C_1$-$C_{18}$alkyl, or $C_1$-$C_{18}$alkoxy, $C_1$-$C_{18}$perfluoroalkyl, $C_1$-$C_{25}$alkyl, which may be interrupted by —O—, or —S—; or —$COOR^{103}$;

$R^{108}$ and $R^{109}$ are independently of each other H, $C_1$-$C_{25}$alkyl, $C_1$-$C_{25}$alkyl which is substituted by E and/or interrupted by D, $C_7$-$C_{25}$arylalkyl, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, or $R^{108}$ and $R^{109}$ together form a group of formula =$CR^{110}R^{111}$, wherein $R^{110}$ and $R^{111}$ are independently of each other H, $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, or $C_2$-$C_{20}$heteroaryl, or $C_2$-$C_{20}$heteroaryl which is substituted by G, or $R^{108}$ and $R^{109}$ together form a five or six membered ring, which optionally can be substituted by $C_1$-$C_{18}$alkyl, $C_1$-$C_{18}$alkyl which is substituted by E and/or interrupted by D, $C_6$-$C_{24}$aryl, $C_6$-$C_{24}$aryl which is substituted by G, $C_2$-$C_{20}$heteroaryl, $C_2$-$C_{20}$heteroaryl which is substituted by G, $C_2$-$C_{18}$alkenyl, $C_2$-$C_{18}$alkynyl, $C_1$-$C_{18}$alkoxy, $C_1$-$C_{18}$alkoxy which is substituted by E and/or interrupted by D, or $C_7$-$C_{25}$aralkyl, D is —CO—, —COO—, —S—, —O—, or —$NR^{112}$—, E is $C_1$-$C_8$thioalkoxy, $C_1$-$C_8$alkoxy, CN, —$NR^{112}R^{113}$, —$CONR^{112}R^{113}$, or halogen, G is E, or $C_1$-$C_{18}$alkyl, and $R^{112}$ and $R^{113}$ are independently of each other H, $C_6$-$C_{18}$aryl, $C_6$-$C_{18}$aryl which is substituted by $C_1$-$C_{18}$alkyl or $C_1$-$C_{18}$alkoxy, $C_1$-$C_{18}$alkyl, or $C_1$-$C_{18}$alkyl which is interrupted by —O—, $R^{114}$ is $C_1$-$C_{25}$alkyl, which may optionally be interrupted by one, or more oxygen, or sulphur atoms, $R^{115}$ and $R^{115'}$ are independently of each other hydrogen, halogen, cyano, $C_1$-$C_{25}$alkyl, which may optionally be interrupted by one, or more oxygen, or sulphur atoms, $C_1$-$C_{25}$alkoxy, $C_7$-$C_{25}$arylalkyl, or —≡—$R^{116}$, wherein $R^{116}$ is a $C_1$-$C_{10}$alkyl group, or a tri($C_1$-$C_8$alkyl) silyl group;

$R^{117}$ and $R^{117'}$ are independently of each other $C_1$-$C_{25}$alkyl group, $C_7$-$C_{25}$arylalkyl, or a phenyl group, which can be substituted one to three times with $C_1$-$C_8$alkyl and/or $C_1$-$C_8$alkoxy;

$R^{118}$, $R^{119}$, $R^{120}$ and $R^{121}$ are independently of each other hydrogen, halogen, halogenated $C_1$-$C_{25}$alkyl, cyano, $C_1$-$C_{25}$alkyl, which may optionally be interrupted by one or more oxygen or sulphur atoms, $C_7$-$C_{25}$arylalkyl, or $C_1$-$C_{25}$alkoxy;

$R^{122}$ and $R^{122'}$ are independently of each other hydrogen, $C_6$-$C_{18}$aryl, $C_6$-$C_{18}$aryl which is substituted by $C_1$-$C_{18}$alkyl, or $C_1$-$C_{18}$alkoxy, or $C_1$-$C_{25}$alkyl, which may optionally be interrupted by one or more oxygen or sulphur atoms, or $C_7$-$C_{25}$arylalkyl, with the proviso that at least one of the groups $R^1$, $R^2$, $R^3$, $R^{3'}$, $R^4$, $R^{4'}$, $R^5$, $R^{5'}$, $R^6$, $R^{6'}$, $R^7$, $R^{7'}$, $R^8$, $R^{8'}$, $R^9$ and $R^{9'}$ comprise $E^{Si}$ and/or $D^{Si}$;

and wherein the polymer comprises at least one unit of the formula Ia to Ie,

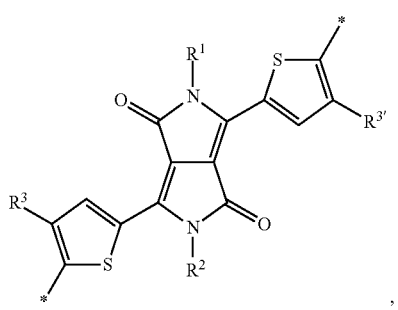
(Ia)

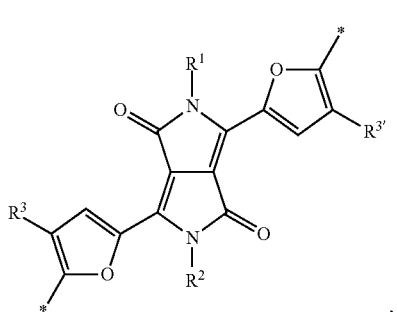
(Ib)

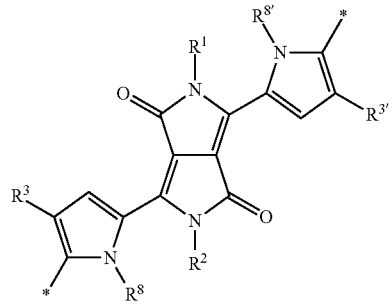
(Ic)

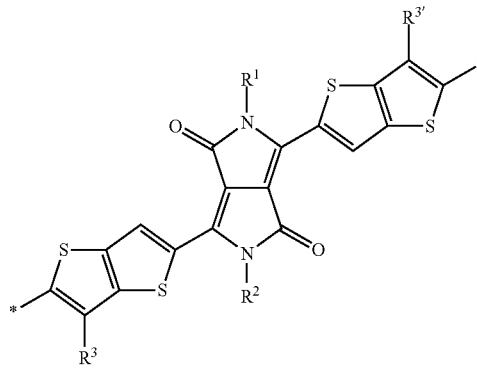
(Id)

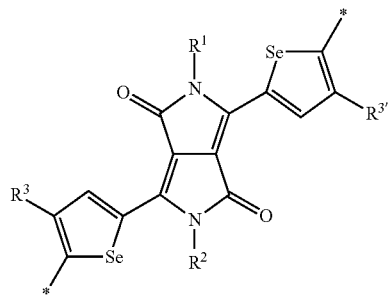
(Ie)

wherein $R^1$ and $R^2$ may be the same or different and are selected from $C_1$-$C_8$alkyl which is substituted with $E^{Si}$, $E^{Si}$ is —$SiR^{161}R^{162}R^{163}$;

$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl, $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;

$R^{164}$, $R^{165}$, $R^{166}$ are independently of each other $C_1$-$C_8$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;

$R^{169}$, $R^{170}$, $R^{171}$ are independently of each other $C_1$-$C_8$alkyl, $C_1$-$C_8$haloalkyl, $C_2$-$C_8$alkenyl, —O—Si($CH_3$)$_3$, or phenyl;

d is an integer from 1 to 10;

$R^3$ and $R^{3'}$ are independently of each other hydrogen, or $C_1$-$C_{25}$alkyl; and $R^8$ and $R^{8'}$ are independently of each other hydrogen, or $C_1$-$C_{25}$alkyl.

2. A polymer comprising a repeating unit of the formula

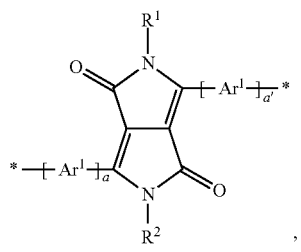
(I')

wherein
R$^1$ and R$^2$ may be the same or different and are selected from C$_1$-C$_{25}$alkyl, which is substituted one or more times with E$^{Si}$ and/or interrupted one or more times with D$^{Si}$, C$_1$-C$_{25}$haloalkyl, which is substituted one or more times with E$^{Si}$ and/or interrupted one or more times with D$^{Si}$, C$_7$-C$_{25}$arylalkyl, which is substituted one or more times with E$^{Si}$ and/or interrupted one or more times with D$^{Si}$, C$_2$-C$_{25}$alkenyl, which is substituted one or more times with E$^{Si}$ and/or interrupted one or more times with D$^{Si}$, C$_2$-C$_{25}$haloalkenyl, which is substituted one or more times with E$^{Si}$ and/or interrupted one or more times with D$^{Si}$, C$_5$-C$_{12}$cycloalkyl, which is substituted one or more times with E$^{Si}$ and/or interrupted one or more times with D$^{Si}$, phenyl, or naphthyl which are substituted one or more times with E$^{Si}$, and a is 1, 2, or 3,
a' is 1, 2, or 3,
wherein
E$^{Si}$ is —SiR$^{161}$R$^{162}$R$^{163}$ or —O—SiR$^{161}$R$^{162}$R$^{163}$,
D$^{Si}$ is —SiR$^{161}$R$^{162}$—, —SiR$^{161}$R$^{162}$—(O—SiR$^{161}$R$^{162}$)$_d$— or —O—SiR$^{161}$R$^{162}$—,
R$^{161}$, R$^{162}$ and R$^{163}$ are independently of each other hydrogen, C$_1$-C$_{25}$alkyl, C$_3$-C$_{12}$cycloalkyl, which might optionally be substituted with C$_1$-C$_4$alkyl, C$_1$-C$_{25}$haloalkyl, C$_2$-C$_{25}$alkenyl, —O—SiR$^{164}$R$^{165}$R$^{166}$, —(O—SiR$^{164}$R$^{165}$)$_d$—R$^{166}$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl which is substituted 1 to 3 times by C$_1$-C$_{24}$alkyl, halogen, cyano or C$_1$-C$_{25}$alkoxy;
R$^{164}$, R$^{165}$ and R$^{166}$ are independently of each other hydrogen, C$_1$-C$_{25}$alkyl, C$_3$-C$_{12}$cycloalkyl, which might optionally be substituted with C$_1$-C$_4$alkyl, C$_1$-C$_{25}$haloalkyl, C$_2$-C$_{25}$alkenyl, —O—SiR$^{169}$R$^{170}$R$^{171}$, —(O—SiR$^{169}$R$^{170}$)$_d$—R$^{171}$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl which is substituted 1 to 3 times by C$_1$-C$_{24}$alkyl, halogen, cyano or C$_1$-C$_{25}$alkoxy;
R$^{169}$, R$^{170}$ and R$^{171}$ are independently of each other hydrogen, C$_1$-C$_{25}$alkyl, C$_3$-C$_{12}$cycloalkyl, which might optionally be substituted with C$_1$-C$_4$alkyl, C$_1$-C$_{25}$haloalkyl, C$_2$-C$_{25}$alkenyl, —O—Si(CH$_3$)$_3$, C$_1$-C$_{25}$alkoxy, C$_3$-C$_{24}$(hetero)aryloxy, NR$^{167}$R$^{168}$, halogen, C$_1$-C$_{25}$acyloxy, phenyl, phenyl which is substituted 1 to 3 times by C$_1$-C$_{24}$alkyl, halogen, cyano or C$_1$-C$_{25}$alkoxy;
R$^{167}$ and R$^{168}$ are independently of each other hydrogen, C$_6$-C$_{18}$aryl, C$_6$-C$_{18}$aryl which is substituted by C$_1$-C$_{18}$alkyl, or C$_1$-C$_{18}$alkoxy, or C$_1$-C$_{25}$alkyl, which may optionally be interrupted by one or more oxygen or sulphur atoms, or C$_7$-C$_{25}$arylalkyl; and d is an integer from 1 to 50;
Ar$^1$ and Ar$^{1'}$ are independently of each other

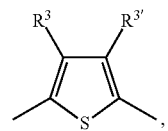
(XIa)

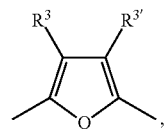
(XIb)

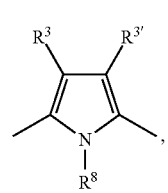
(XIc)

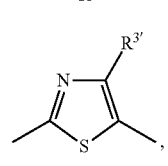
(XId)

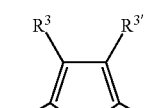
(XIe)

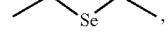
(XIf)

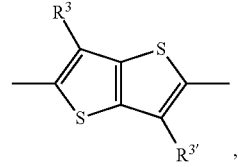
(XIg)

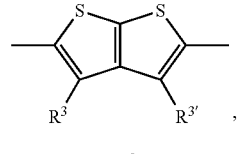
(XIh)

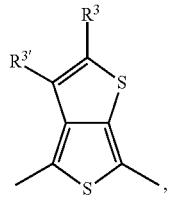
(XIi)

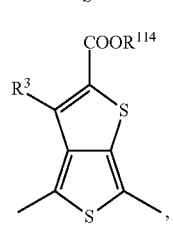

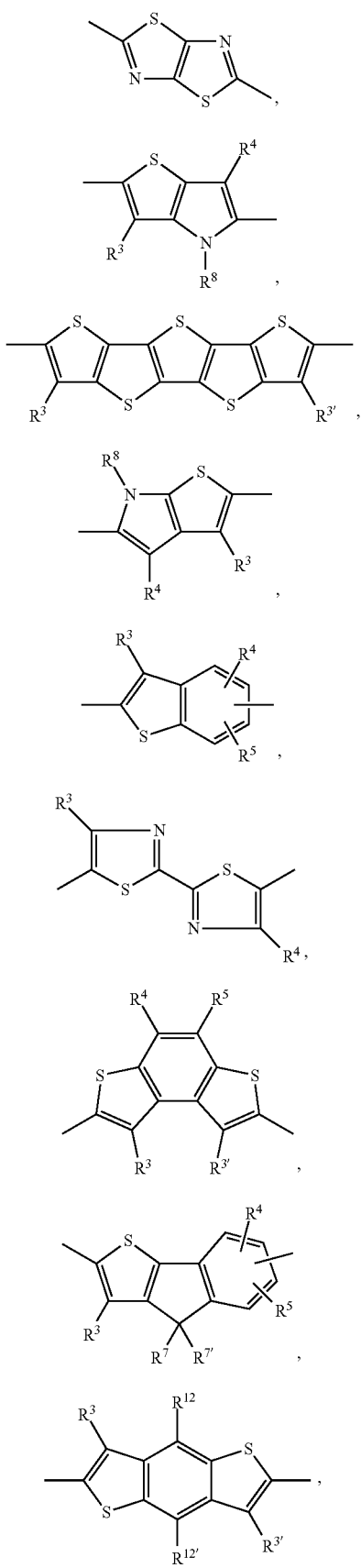
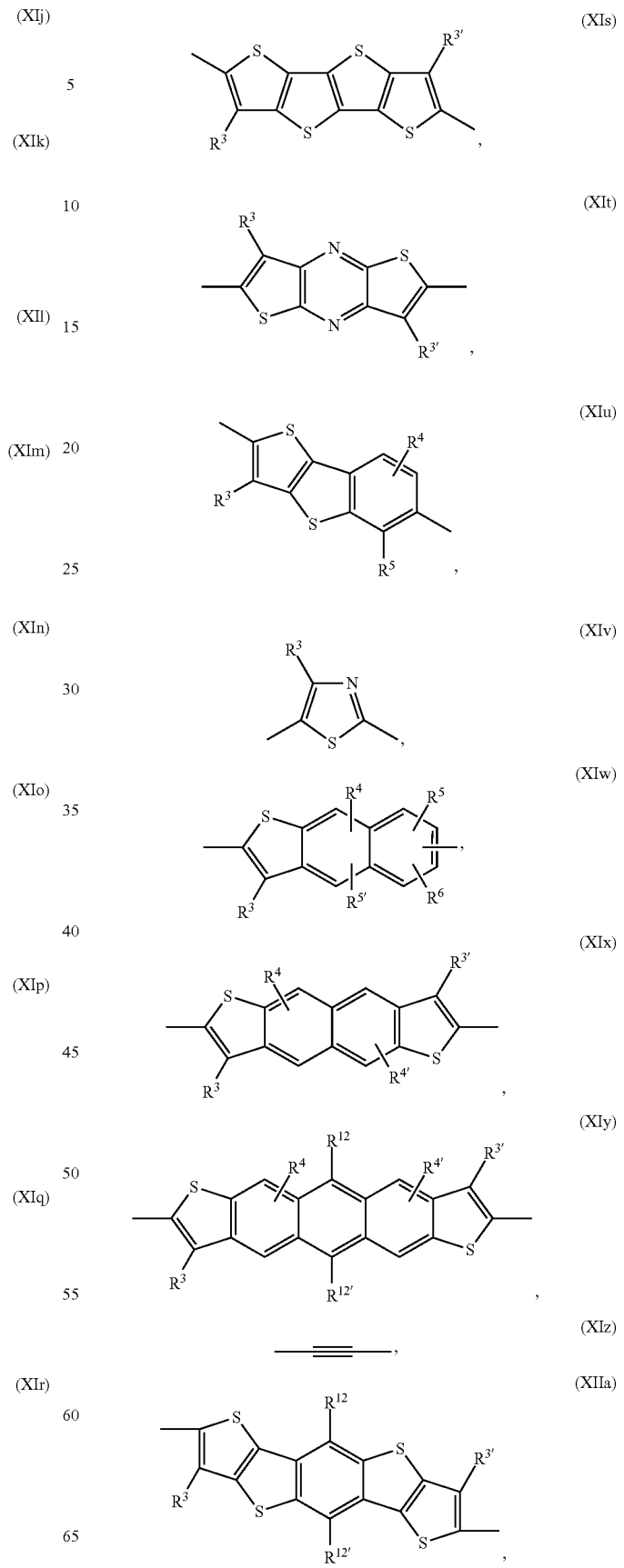

-continued
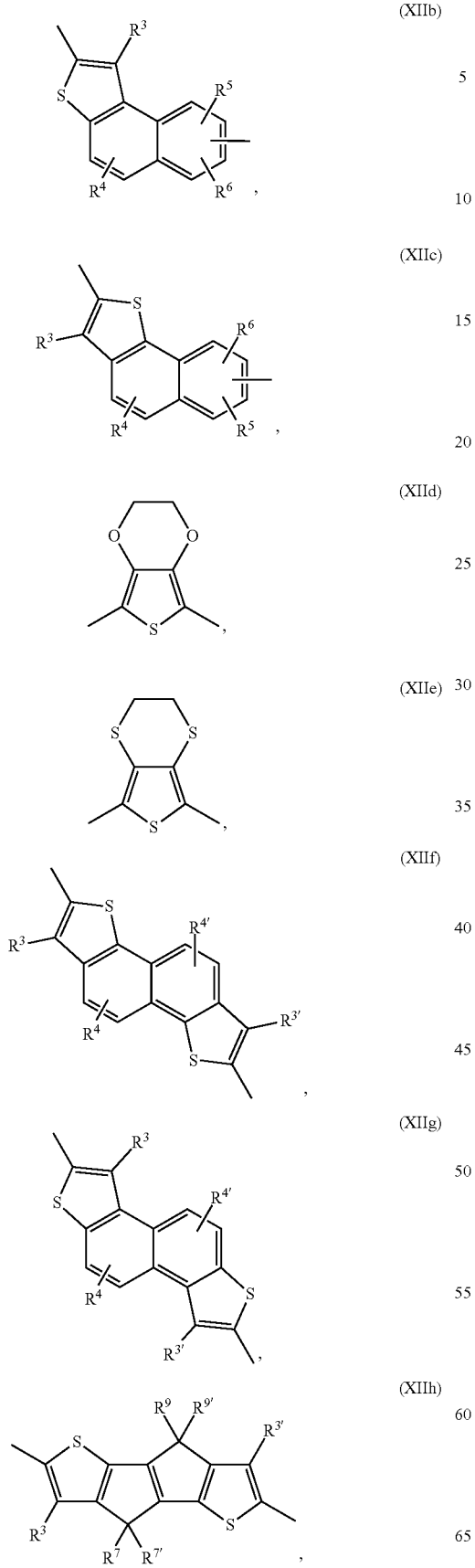
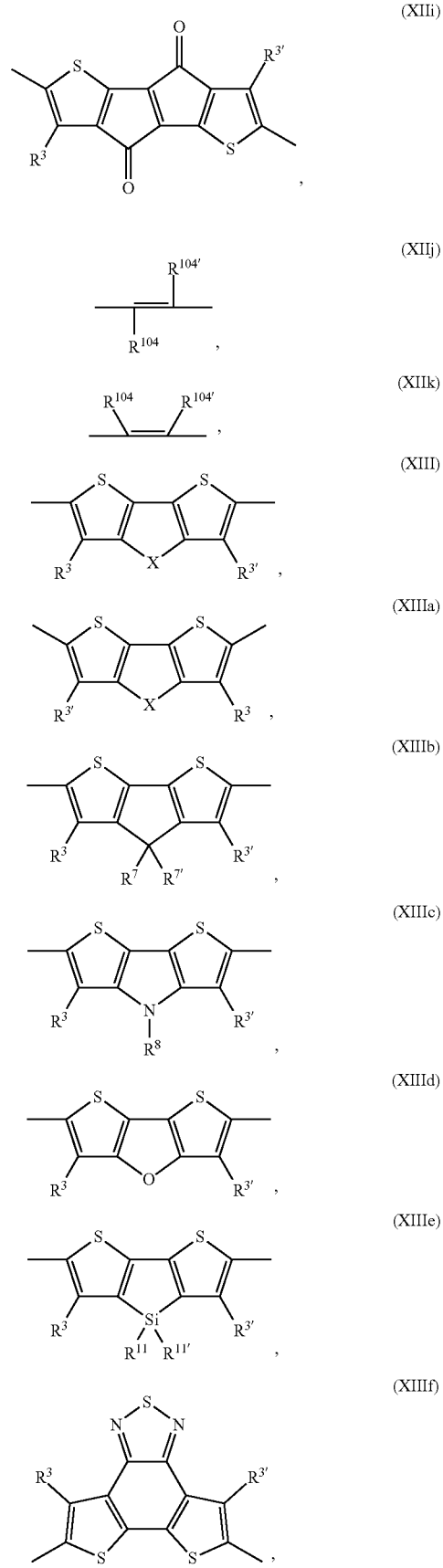

-continued

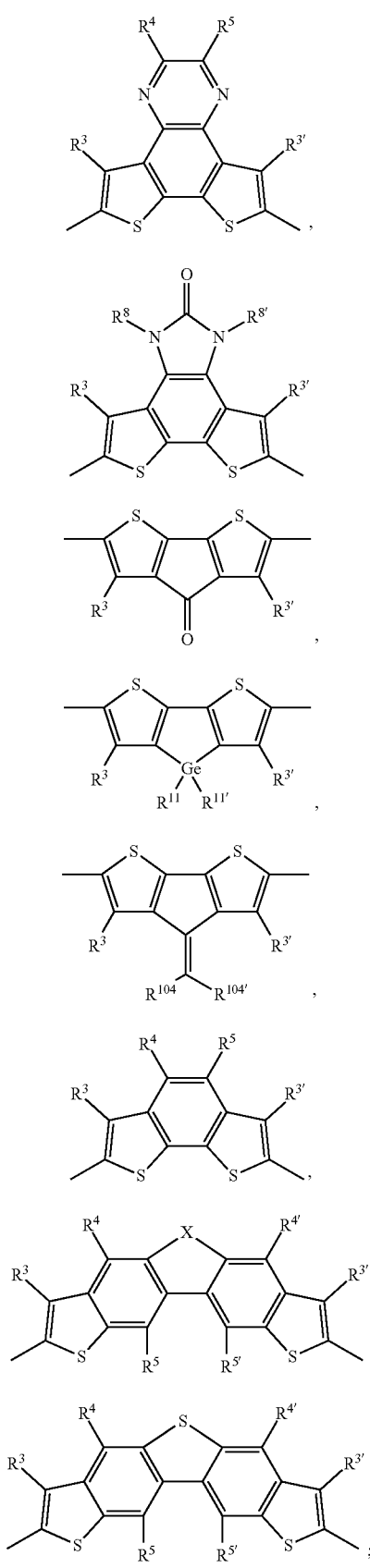

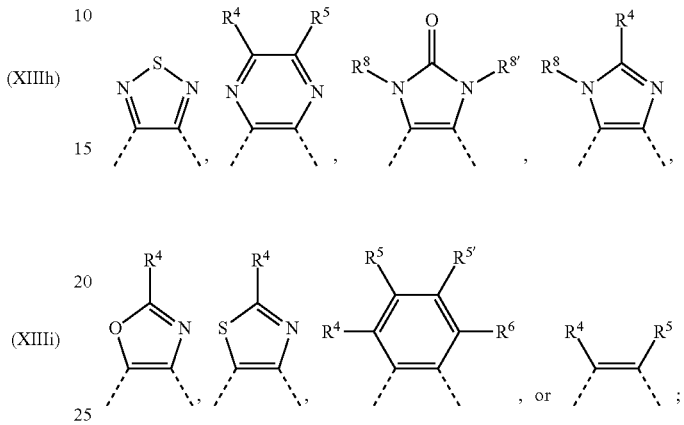

wherein

X is —O—, —S—, —NR$^8$—, —Si(R$^{11}$)(R$^{11'}$)—, —Ge(R$^{11}$)(R$^{11'}$)—, —C(R$^7$)(R$^{7'}$)—, —C(=O)—, —C(=CR$^{104}$R$^{104'}$)—,

R$^3$ and R$^{3'}$ are independently of each other hydrogen, halogen, E$^{Si}$, halogenated C$_1$-C$_{25}$alkyl, cyano, C$_1$-C$_{25}$alkyl, which may optionally be interrupted by one or more oxygen or sulphur atoms, C$_7$-C$_{25}$arylalkyl, C$_1$-C$_{25}$alkyl substituted with one or more E$^{Si}$, or C$_1$-C$_{25}$alkoxy;

R$^4$, R$^{4'}$, R$^5$, R$^{5'}$, R$^6$, and R$^{6'}$ are independently of each other hydrogen, halogen, E$^{Si}$, halogenated C$_1$-C$_{25}$alkyl, cyano, C$_1$-C$_{25}$alkyl, which optionally be interrupted by one or more oxygen or sulphur atoms, C$_7$-C$_{25}$arylalkyl, C$_1$-C$_{25}$alkyl substituted with one or more E$^{Si}$, or C$_1$-C$_{25}$alkoxy;

R$^7$, R$^{7'}$, R$^9$ and R$^{9'}$ are independently of each other hydrogen, C$_1$-C$_{25}$alkyl, which may optionally be interrupted by one, or more oxygen, or sulphur atoms, C$_1$-C$_{25}$alkyl substituted with one or more E$^{Si}$, or C$_7$-C$_{25}$arylalkyl, or R$^7$ and R$^{7'}$, or R$^9$ and R$^{9'}$ are together =CR$^{104}$R$^{104'}$;

R$^8$ and R$^{8'}$ are independently of each other hydrogen, C$_6$-C$_{18}$aryl; C$_6$-C$_{18}$aryl which is substituted by C$_1$-C$_{18}$alkyl, or C$_1$-C$_{18}$alkoxy, C$_1$-C$_{25}$alkyl, which may optionally be interrupted by one or more oxygen or sulphur atoms, C$_1$-C$_{25}$alkyl substituted with one or more E$^{Si}$, or C$_7$-C$_{25}$arylalkyl, R$^{11}$ and R$^{11'}$ are independently of each other C$_1$-C$_{25}$alkyl group, C$_7$-C$_{25}$arylalkyl, or a phenyl group, which can be substituted one to three times with C$_1$-C$_8$alkyl and/or C$_1$-C$_8$alkoxy;

R$^{12}$ and R$^{12'}$ are independently of each other hydrogen, halogen, cyano, C$_1$-C$_{25}$alkyl, which may optionally be interrupted by one, or more oxygen, or sulphur atoms, C$_1$-C$_{25}$alkoxy, C$_7$-C$_{25}$arylalkyl, or =R$^{13}$, wherein R$^{13}$ is a C$_1$-C$_{10}$alkyl group, or a tri(C$_1$-C$_8$alkyl)silyl group.

3. A polymer, which is a polymer of the formula Ia1 to Ia7,

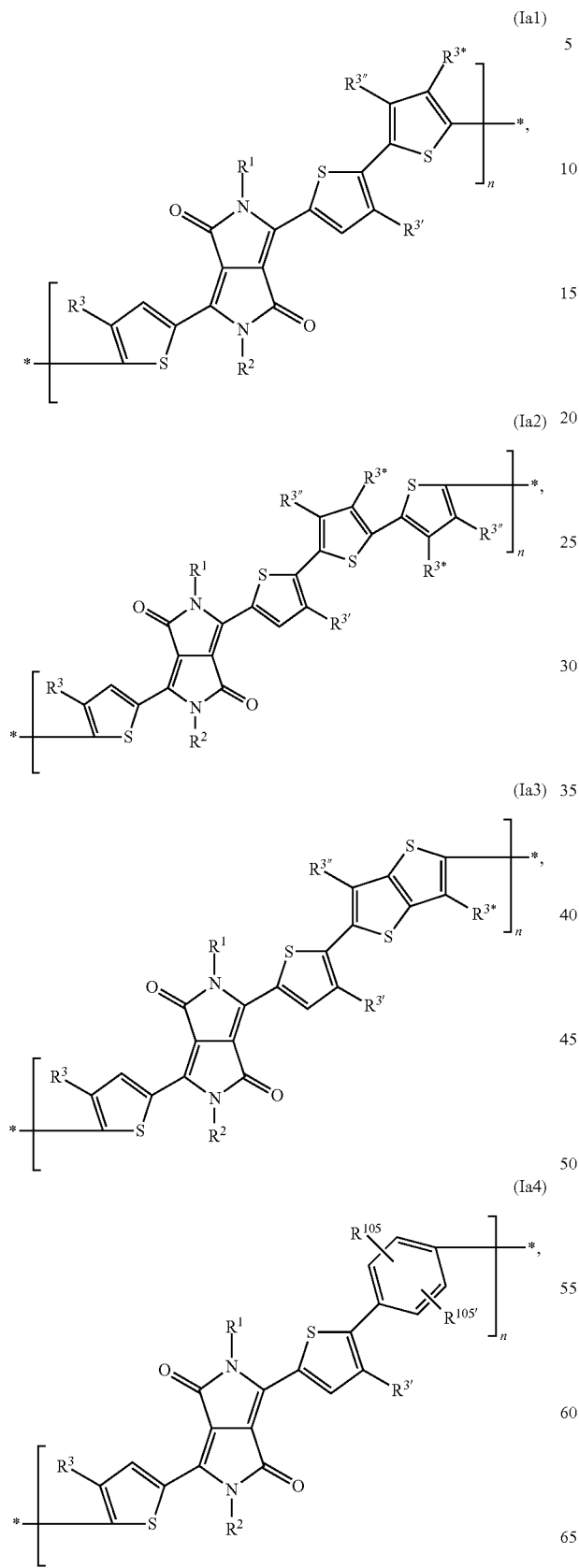

(Ia1) (Ia2) (Ia3) (Ia4)

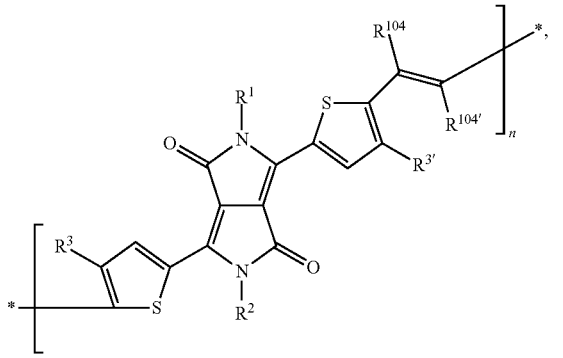

(Ia5)

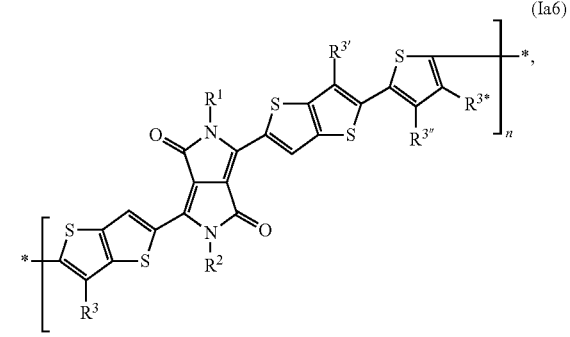

(Ia6)

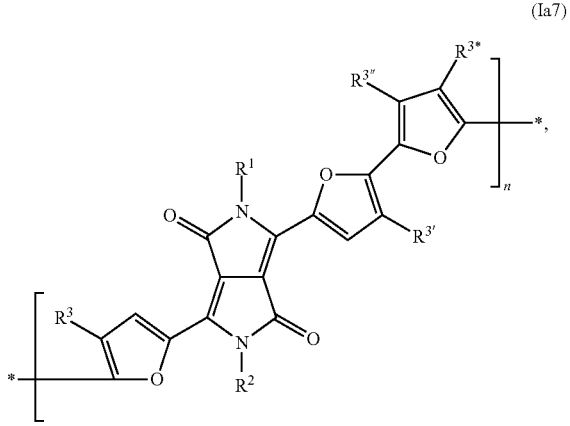

(Ia7)

wherein n is from 4 to 1000, $R^1$ and $R^2$ may be the same or different and are a $C_1$-$C_8$alkyl which is substituted with $E^{Si}$, $R^3$ and $R^{3'}$ are independently of each other hydrogen, halogen, cyano, $C_1$-$C_{25}$alkyl or $C_1$-$C_{25}$alkoxy;

$E^{Si}$ is —$SiR^{161}R^{162}R^{163}$;

$R^{161}$, $R^{162}$ and $R^{163}$ are independently of each other $C_1$-$C_8$alkyl, $C_5$-$C_6$cycloalkyl, which might optionally be substituted with $C_1$-$C_4$alkyl, $C_1$-$C_8$haloalkyl, $C_2$-$C_8$alkenyl, —O—$SiR^{164}R^{165}R^{166}$, —(O—$SiR^{164}R^{165})_d$—$R^{166}$, or phenyl;

$R^{164}$, $R^{165}$ and $R^{166}$ are independently of each other $C_1$-$C_5$alkyl, $C_1$-$C_8$haloalkyl, $C_2$-$C_8$alkenyl, —O—$SiR^{169}R^{170}R^{171}$, —(O—$SiR^{169}R^{170})_d$—$R^{171}$, or phenyl;

$R^{169}$, $R^{170}$ and $R^{171}$ are independently of each other $C_1$-$C_8$alkyl, $C_1$-$C_8$haloalkyl, $C_2$-$C_8$alkenyl, —O—Si$(CH_3)_3$, or phenyl;

d is an integer from 1 to 10;

$R^{3''}$ and $R^{3*}$ are independently of each other hydrogen, halogen, cyano, $C_1$-$C_{25}$alkyl or $C_1$-$C_{25}$alkoxy;

$R^{104}$ and $R^{104'}$ are independently of each other hydrogen, cyano, $COOR^{103}$, $C_1$-$C_{25}$alkyl, wherein $R^{103}$ is $C_1$-$C_8$alkyl; and $R^{105}$ and $R^{105'}$ are independently of each other hydrogen, halogen, cyano, $C_1$-$C_{25}$alkyl or $C_1$-$C_{25}$alkoxy.

4. An organic semiconductor material, layer or component, comprising the polymer according to claim 1.

5. An electronic device, comprising the polymer according to claim 1.

6. The electronic device according to claim 5, wherein said device is an organic photovoltaic device, a photodiode, or an organic field effect transistor.

7. A method for the preparation of an electronic device, said method comprises
applying a solution and/or dispersion of the polymer according to claim 1 in an organic solvent to a suitable substrate, and
removing the solvent.

8. An organic semiconductor material, layer or component, comprising the polymer according to claim 2.

9. An electronic device, comprising the polymer according to claim 2.

10. The electronic device according to claim 9, wherein said device is an organic photovoltaic device, a photodiode, or an organic field effect transistor.

11. A method for the preparation of an electronic device, said method comprises
applying a solution and/or dispersion of the polymer according to claim 2 in an organic solvent to a suitable substrate, and
removing the solvent.

12. An organic semiconductor material, layer or component, comprising the polymer according to claim 3.

13. An electronic device, comprising the polymer according to claim 3.

14. The electronic device according to claim 13, wherein said device is an organic photovoltaic device, a photodiode, or an organic field effect transistor.

15. A method for the preparation of an electronic device, said method comprises
applying a solution and/or dispersion of the polymer according to claim 3 in an organic solvent to a suitable substrate, and
removing the solvent.

16. The polymer according to claim 1, wherein $R^1$ and $R^2$ are $C_1$-$C_{25}$alkyl which is substituted one or more times with $E^{Si}$ and/or interrupted one or more times with $D^{Si}$.

17. The polymer according to claim 1, wherein $E^{Si}$ is $-SiR^{161}R^{162}R^{163}$, wherein $R^{161}$, $R^{162}$ and $R^{163}$ are independently of each other $C_1$-$C_{25}$alkyl, $C_1$-$C_{25}$haloalkyl, $C_2$-$C_{25}$alkenyl, $C_3$-$C_{12}$cycloalkyl, which might optionally be substituted with $C_1$-$C_4$alkyl; phenyl, $-O-SiR^{164}R^{165}R^{166}$, or $-(O-SiR^{164}R^{165})_d-R^{166}$, wherein $R^{164}$, $R^{165}$ and $R^{166}$ are independently of each other $C_1$-$C_8$alkyl, $C_1$-$C_8$haloalkyl, $C_2$-$C_8$alkenyl, or phenyl, and in case of a group $-(O-SiR^{164}R^{165})_d-R^{166}$ $R^{164}$ and $R^{165}$ are independently of each other $C_1$-$C_8$alkyl, $R^{166}$ is $C_1$-$C_8$alkyl, or phenyl and d is an integer of 2 to 5.

18. The polymer according to claim 1, wherein $D^{Si}$ is $-SiR^{161}R^{162}-$, wherein $R^{161}$ and $R^{162}$ are independently of each other $C_1$-$C_{25}$alkyl, $C_1$-$C_{25}$haloalkyl, $C_2$-$C_{25}$alkenyl, or phenyl, or $-SiR^{161}R^{162}-(O-SiR^{161}R^{162})_d-$, wherein d is 2 to 5 and $R^{161}$ and $R^{162}$ are $C_1$-$C_{25}$alkyl.

19. The polymer according to claim 1, wherein $Ar^1$ and $Ar^{1'}$ are independently of each other a group of formula XIa, XIb, XIc, XIe, XIf, XII, XIp, XIr, XIs, XIx, XIIf, XIIg, XIIIa, XIIId, or XIIIl.

20. The polymer according to claim 2, wherein $R^1$ and $R^2$ are $C_1$-$C_{25}$alkyl which is substituted one or more times with $E^{Si}$ and/or interrupted one or more times with $D^{Si}$.

21. The polymer according to claim 2, $E^{Si}$ is $-SiR^{161}R^{162}R^{163}$, wherein $R^{161}$, $R^{162}$ and $R^{163}$ are independently of each other $C_1$-$C_{25}$alkyl, $C_1$-$C_{25}$haloalkyl, $C_2$-$C_{25}$alkenyl, $C_3$-$C_{12}$cycloalkyl, which might optionally be substituted with $C_1$-$C_4$alkyl; phenyl, $-O-SiR^{164}R^{165}R^{166}$, or $-(O-SiR^{164}R^{165})_d-R^{166}$, wherein $R^{164}$, $R^{165}$ and $R^{166}$ are independently of each other $C_1$-$C_8$alkyl, $C_1$-$C_8$haloalkyl, $C_2$-$C_8$alkenyl, or phenyl, and in case of a group $-(O-SiR^{164}R^{165})_d-R^{166}$ $R^{164}$ and $R^{165}$ are independently of each other $C_1$-$C_8$alkyl, $R^{166}$ is $C_1$-$C_8$alkyl, or phenyl and d is an integer of 2 to 5.

22. The polymer according to claim 2, wherein $D^{Si}$ is $-SiR^{161}R^{162}-$, wherein $R^{161}$ and $R^{162}$ are independently of each other $C_1$-$C_{25}$alkyl, $C_1$-$C_{25}$haloalkyl, $C_2$-$C_{25}$alkenyl, or phenyl, or $-SiR^{161}R^{162}-(O-SiR^{161}R^{162})_d-$, wherein d is 2 to 5 and $R^{161}$ and $R^{162}$ are $C_1$-$C_{25}$alkyl.

23. The polymer according to claim 2, wherein $Ar^1$ and $Ar^{1'}$ are independently of each other a group of formula XIa, XIb, XIc, XIe, XIf, XII, XIp, XIr, XIs, XIx, XIIf, XIIg, XIIIa, XIIId, or XIIIl.

\* \* \* \* \*